United States Patent
Shahaf et al.

(10) Patent No.: US 11,471,618 B2
(45) Date of Patent: *Oct. 18, 2022

(54) ADJUSTABLE DOSING DELIVERY AND MULTI SECTIONED DRUG COMPARTMENT

(71) Applicant: SIPNOSE LTD., Yokne'am Ilit (IL)

(72) Inventors: Daniel Shahaf, M.P. Emek Ha-Yarden (IL); Iris Shichor, Zichron Yaakov (IL)

(73) Assignee: SIPNOSE LTD., Yokne'am Ilit (IL)

( * ) Notice: Subject to any disclaimer, the term of this patent is extended or adjusted under 35 U.S.C. 154(b) by 135 days.

This patent is subject to a terminal disclaimer.

(21) Appl. No.: 15/982,996

(22) Filed: May 17, 2018

(65) Prior Publication Data
US 2019/0015613 A1   Jan. 17, 2019

Related U.S. Application Data

(63) Continuation-in-part of application No. 14/733,143, filed on Jun. 8, 2015, now Pat. No. 11,116,914.
(Continued)

(51) Int. Cl.
*A61M 11/02* (2006.01)
*A61M 15/08* (2006.01)
(Continued)

(52) U.S. Cl.
CPC ........ *A61M 11/02* (2013.01); *A61M 15/0003* (2014.02); *A61M 15/003* (2014.02);
(Continued)

(58) Field of Classification Search
CPC .. A61M 11/00; A61M 11/001; A61M 11/006; A61M 11/007; A61M 11/008;
(Continued)

(56) References Cited

U.S. PATENT DOCUMENTS

| | | | |
|---|---|---|---|
| 462,990 A | 11/1891 | Oppenheimer | |
| 3,921,637 A | 11/1975 | Bennie et al. | |

(Continued)

FOREIGN PATENT DOCUMENTS

| | | |
|---|---|---|
| DE | 20 2013 105 715 U1 | 2/2014 |
| EP | 1 023 098 B1 | 9/2004 |

(Continued)

OTHER PUBLICATIONS

Damm et al., "Intranasal Volume and Olfactory Function", Chemical Senses, 2002, pp. 831-839, vol. 27, Oxford University Press.
(Continued)

*Primary Examiner* — Colin W Stuart
(74) *Attorney, Agent, or Firm* — Foley & Lardner LLP

(57) ABSTRACT

A device is provided for delivering a predetermined volume of at least one substance within a body cavity of a subject. The device contains a) a capsule for containing the predetermined volume of substances; b) a delivery end, having at least one orifice of diameter D, for placement in proximity to the body cavity; c) a valve mechanically connectable to the capsule, having at least two configurations: (i) an active configuration in which the valve enables delivery of the substances; and (ii) an inactive configuration, in which the valve prevents delivery of the substances from the capsule to the body cavity; and d) a fluid tight chamber configured to contain predetermined volume $V_{gas}$ of pressurized gas at a predetermined pressure, $P_{gas}$. The capsule further contains at least one mixing mechanism that mixes the substances and the pressurized gas after the valve is reconfigured to the active configuration.

84 Claims, 46 Drawing Sheets

Related U.S. Application Data

(60) Provisional application No. 62/117,986, filed on Feb. 19, 2015, provisional application No. 62/077,246, filed on Nov. 9, 2014, provisional application No. 62/526,386, filed on Jun. 29, 2017.

(51) Int. Cl.
  *A61M 15/00* (2006.01)
  *B05B 1/00* (2006.01)
  *A61M 11/00* (2006.01)

(52) U.S. Cl.
  CPC ...... *A61M 15/0008* (2014.02); *A61M 15/009* (2013.01); *A61M 15/0031* (2014.02); *A61M 15/0035* (2014.02); *A61M 15/0036* (2014.02); *A61M 15/0091* (2013.01); *A61M 15/0098* (2014.02); *A61M 15/08* (2013.01); *B05B 1/002* (2018.08); *A61M 11/001* (2014.02); *A61M 15/004* (2014.02); *A61M 15/0025* (2014.02); *A61M 15/0061* (2014.02); *A61M 15/0065* (2013.01); *A61M 15/0093* (2014.02); *A61M 2202/04* (2013.01); *A61M 2202/064* (2013.01); *A61M 2205/073* (2013.01); *A61M 2205/36* (2013.01); *A61M 2205/364* (2013.01); *A61M 2205/584* (2013.01); *A61M 2205/7509* (2013.01); *A61M 2205/7518* (2013.01); *A61M 2205/7545* (2013.01); *A61M 2205/8218* (2013.01); *A61M 2205/8225* (2013.01); *A61M 2206/16* (2013.01); *A61M 2209/02* (2013.01); *A61M 2209/045* (2013.01); *A61M 2210/065* (2013.01); *A61M 2210/0618* (2013.01); *A61M 2210/0625* (2013.01); *A61M 2210/0662* (2013.01); *A61M 2210/1089* (2013.01); *A61M 2210/1475* (2013.01)

(58) Field of Classification Search
  CPC ...... A61M 11/02; A61M 11/06; A61M 15/00; A61M 15/0001; A61M 15/002; A61M 15/0028; A61M 15/003; A61M 15/0003; A61M 15/0031; A61M 15/0043; A61M 15/0061; A61M 15/0063; A61M 15/0091; A61M 15/0993; A61M 15/0095; A61M 15/08; A61M 31/00; A61M 2202/04; A61M 2202/064; A61M 2205/073; A61M 2206/16; A61M 2209/02; A61M 2210/0618; A61M 2210/0625; A61M 2210/065; A61M 2210/0662
  See application file for complete search history.

(56) References Cited

U.S. PATENT DOCUMENTS

| | | | |
|---|---|---|---|
| 4,114,615 A | 9/1978 | Wetterlin | |
| 4,620,670 A | 11/1986 | Hughes | |
| 5,740,794 A | 4/1998 | Smith et al. | |
| 6,123,228 A | 9/2000 | Hippensteel | |
| 6,398,074 B1 | 6/2002 | Bruna et al. | |
| 7,497,390 B2 | 3/2009 | Beller | |
| 7,726,308 B1 | 6/2010 | Flora | |
| 7,802,569 B2 | 9/2010 | Yeates et al. | |
| 7,900,659 B2 | 3/2011 | Whitley et al. | |
| 2002/0023641 A1 | 2/2002 | Stadelhofer | |
| 2002/0092520 A1 | 7/2002 | Casper et al. | |
| 2003/0079743 A1 | 5/2003 | Genova et al. | |
| 2003/0187404 A1* | 10/2003 | Waldenburg | A61M 5/285 604/200 |
| 2003/0209455 A1 | 11/2003 | Pynson et al. | |
| 2005/0028812 A1 | 2/2005 | Djupesland | |
| 2006/0067911 A1 | 3/2006 | Nilsson et al. | |
| 2006/0107957 A1* | 5/2006 | Djupesland | A61M 11/00 128/206.11 |
| 2006/0151629 A1 | 7/2006 | Vedrine et al. | |
| 2006/0213514 A1* | 9/2006 | Price | A61M 15/0043 128/203.15 |
| 2007/0060868 A1 | 3/2007 | Tsutsui | |
| 2007/0125371 A1* | 6/2007 | Djupesland | A61M 15/00 128/200.14 |
| 2007/0151562 A1 | 7/2007 | Jones et al. | |
| 2007/0154407 A1* | 7/2007 | Peters | A61M 11/002 424/46 |
| 2008/0092887 A1 | 4/2008 | Hodson et al. | |
| 2008/0210229 A1 | 9/2008 | Corbacho | |
| 2009/0285849 A1 | 11/2009 | Barsanti et al. | |
| 2009/0314293 A1* | 12/2009 | Djupesland | A61M 11/00 128/203.18 |
| 2010/0282246 A1 | 11/2010 | Djupesland et al. | |
| 2011/0048414 A1 | 3/2011 | Hoekman et al. | |
| 2011/0088690 A1* | 4/2011 | Djupesland | A61M 11/006 128/200.23 |
| 2011/0168172 A1 | 7/2011 | Patton et al. | |
| 2011/0283996 A1* | 11/2011 | Abrams | A61M 15/0038 128/200.21 |
| 2012/0291779 A1 | 11/2012 | Haartsen et al. | |
| 2013/0096495 A1* | 4/2013 | Holmqvist | A61M 5/2066 604/89 |
| 2013/0180524 A1 | 7/2013 | Shahaf et al. | |
| 2013/0267864 A1 | 10/2013 | Addington et al. | |
| 2013/0299607 A1 | 11/2013 | Wilkerson et al. | |
| 2013/0345673 A1 | 12/2013 | Ferreri et al. | |
| 2014/0060532 A1 | 3/2014 | Hodges et al. | |
| 2015/0122257 A1 | 5/2015 | Winkler et al. | |
| 2015/0144129 A1* | 5/2015 | Djupesland | A61M 16/14 128/200.23 |
| 2015/0174343 A1 | 6/2015 | Muellinger et al. | |
| 2015/0209325 A1 | 7/2015 | Najarian et al. | |
| 2015/0297845 A1 | 10/2015 | Shahaf et al. | |
| 2016/0129205 A1 | 5/2016 | Shahaf et al. | |
| 2018/0072480 A1 | 3/2018 | Genosar | |
| 2018/0110922 A1 | 4/2018 | Dunki-Jacobs et al. | |
| 2019/0015613 A1 | 1/2019 | Shahaf et al. | |
| 2019/0060168 A1 | 2/2019 | Koska | |
| 2020/0197631 A1 | 6/2020 | Stedman et al. | |
| 2020/0289768 A1 | 9/2020 | Shahaf et al. | |
| 2020/0306463 A1 | 10/2020 | Shahaf et al. | |

FOREIGN PATENT DOCUMENTS

| | | | | |
|---|---|---|---|---|
| EP | 1 752 176 A1 | 2/2007 | | |
| EP | 2 030 645 A1 | 3/2009 | | |
| GB | 0 724 974 A | 2/1955 | | |
| GB | 2 415 376 A | 12/2005 | | |
| WO | WO-90/12567 A1 | 11/1990 | | |
| WO | WO-2012/029064 A1 | 3/2012 | | |
| WO | WO-2013128447 A1 * | 9/2013 | ........... | A61M 11/02 |
| WO | WO-2015/025324 A1 | 2/2015 | | |
| WO | WO-2016/199135 A1 | 12/2016 | | |
| WO | WO-2019/003216 A1 | 1/2019 | | |
| WO | WO-2019/079335 | 4/2019 | | |
| WO | WO-2019/220443 A1 | 11/2019 | | |

OTHER PUBLICATIONS

Derendorf et al., "Molecular and clinical pharmacology of intranasal corticosteroids: clinical and therapeutic implications", Allergy, 2008, pp. 1292-1300, vol. 63, 2008 Blackwell Munksgaard.

Doose et al., "Single-dose pharmacokinetics and effect of food on the bioavailability of topiramate, A novel antiepileptic drug", Journal of Clinical Pharmacology, 1996, pp. 884-891, vol. 36.

Ganger et al., "Tailoring Formulations for Intranasal Nose-to-Brain Delivery: A Review on Architecture, Physico-Chemical Characteristics and Mucociliary Clearance of the Nasal Olfactory Mucosa", Pharmaceutics, 2018, pp. 1-28, vol. 10, No. 116.

International Preliminary Reporton Patentability for International Application No. PCT/IL2014/050752, dated Feb. 23, 2016.

(56) References Cited

OTHER PUBLICATIONS

International Search Report & International Written Opinion of the International Searching Authority issued in International Application No. PCT/IL2014/050752, dated Dec. 18, 2014.

Khan et al., "Progress in brain targeting drug delivery system by nasal route", Journal of Controlled Release, 2017, pp. 364-389, vol. 268, Elsevier B.V.

Lammi et al., "Treatment with intranasal iloprost reduces disease manifestations in a murine model of previously established COPD", The American Journal of Physiology—Lung Cellular and Molecular Physiology, 2016, pages L630-L638, vol. 310, 2016 American Physiological Society.

Leombruni et al., "Treatment of obese patients with binge eating disorder using topiramate: a review", Neuropsychiatric Disease and Treatment, 2009, pp. 385-392, vol. 5, Dove Medical Press Ltd.

Massolt et al., "Appetite suppression through smelling of dark chocolate correlates with changes in ghrelin in young women", Regulatory Peptides, 2010, pp. 81-86, vol. 161, 2010 Elsevier B.V.

Puhakka et al., "The common cold: Effects of intranasal fluticasone propionate treatment", The Journal of Allergy and Clinical Immunology, 1998, pp. 726-731, vol. 101, No. 6, Part 1, Mosby, Inc.

Ramaekers et al., "Odors: appetizing or satiating? Development of appetite during odor exposure overtime", International Journal of Obesity, 2014, pp. 650-656, vol. 38, 2014 Macmillan Publishers Limited.

Scheibe et al., "Intranasal Administration of Drugs", Archives of Otolaryngology—Head & Neck Surgery, Jun. 2008, pp. 643-646, vol. 134, No. 6, 2008 American Medical Association.

Schiffman et al., "Taste and smell perception affect appetite and immunity in the elderly", European Journal of Clinical Nutrition, 2000, pp. S54-S63, Suppl 3, 2000 Macmillan Publishers Ltd.

Schriever et al., "Size of nostril opening as a measure of intranasal volume", Physiology & Behavior, 2013, pp. 3-5, vol. 110-111, 2012 Elsevier Inc.

Yeomans, "Olfactory influences on appetite and satiety in humans", Physiology and Behavior, 2006, pp. 1-14, vol. 89, No. 1.

\* cited by examiner

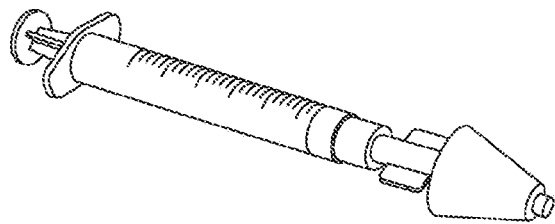
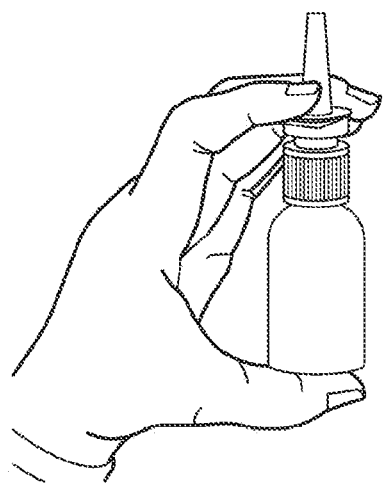
Prior Art
Fig. 1A
Prior Art
Fig. 1B
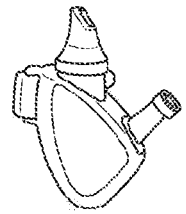
Prior Art
Fig. 1C
Prior Art
Fig. 1D

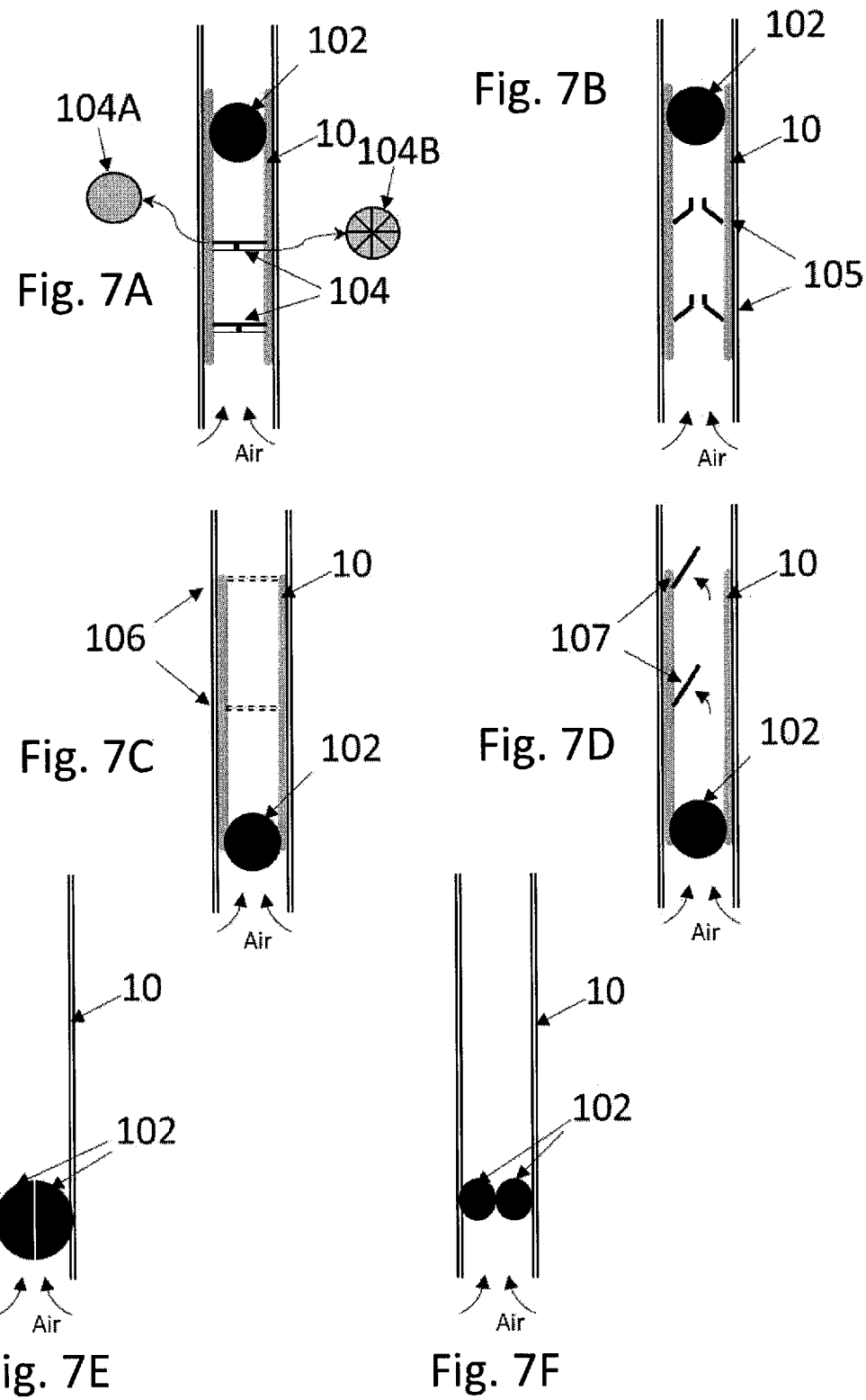

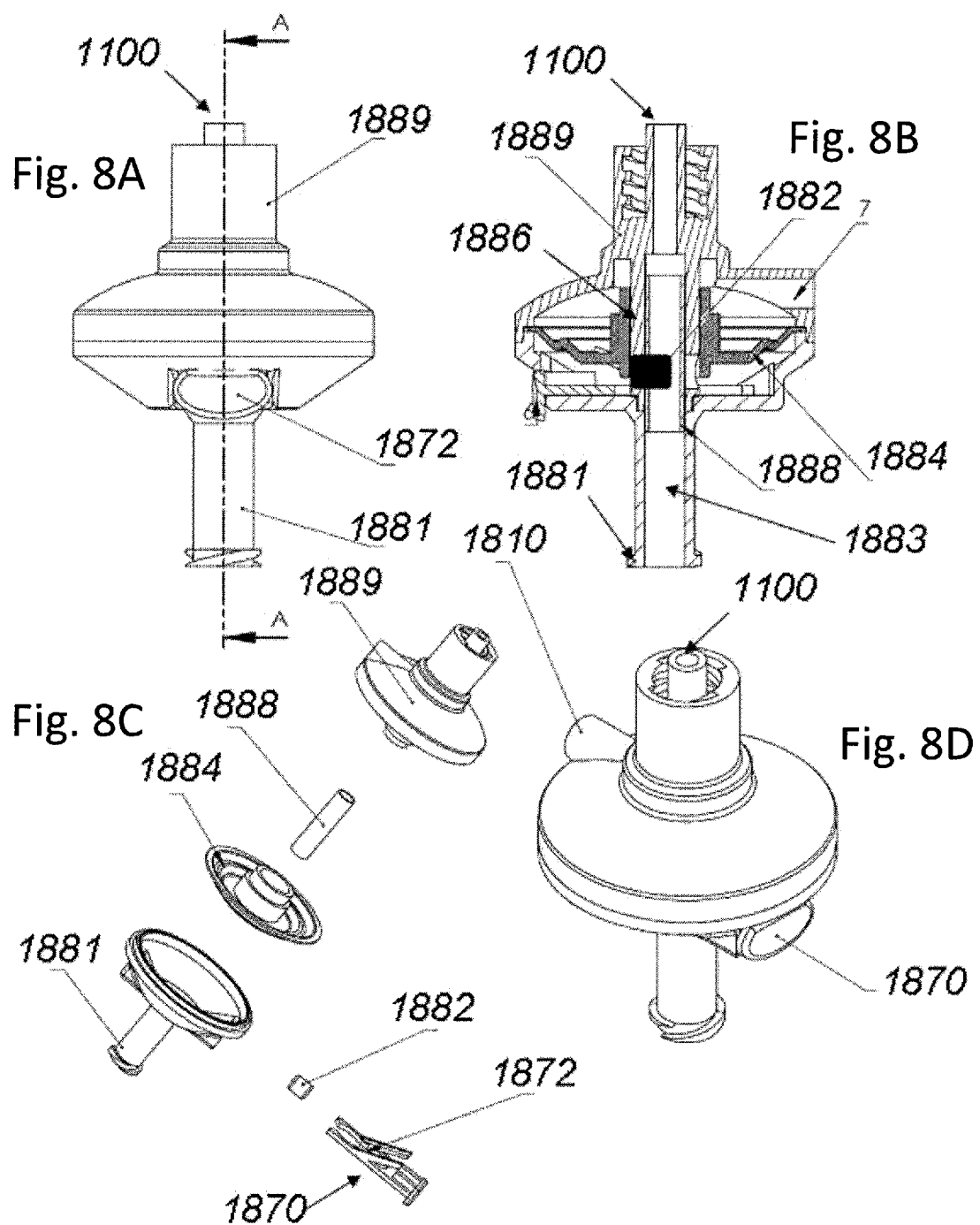

SECTION A-A

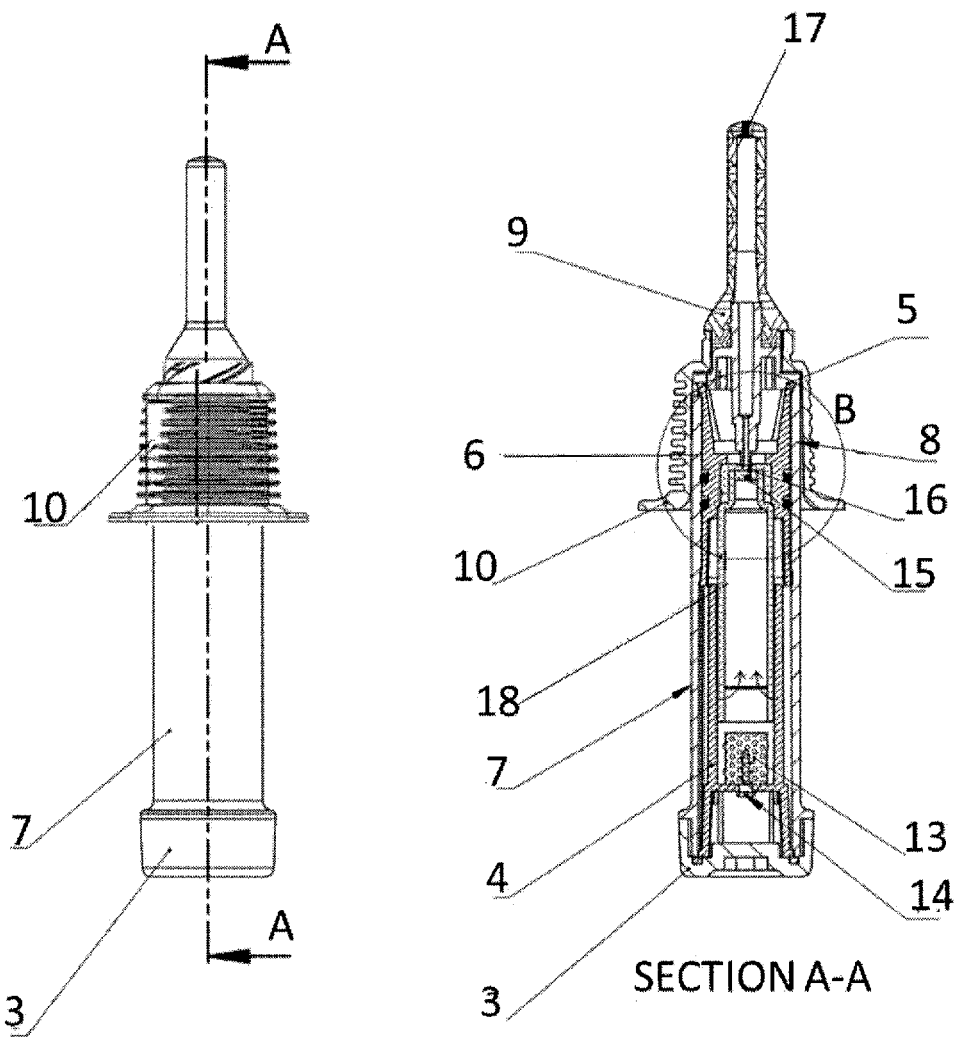
Fig. 14A
Fig. 14B
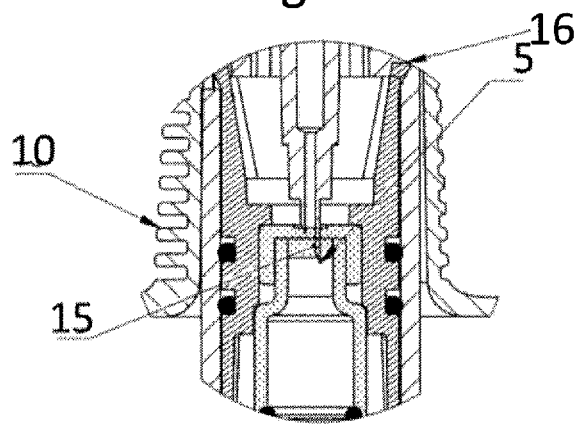
Fig. 14C
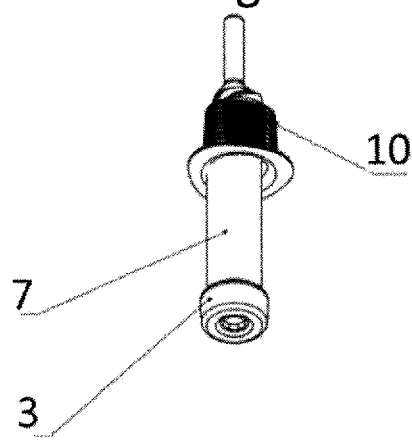
Fig. 14D

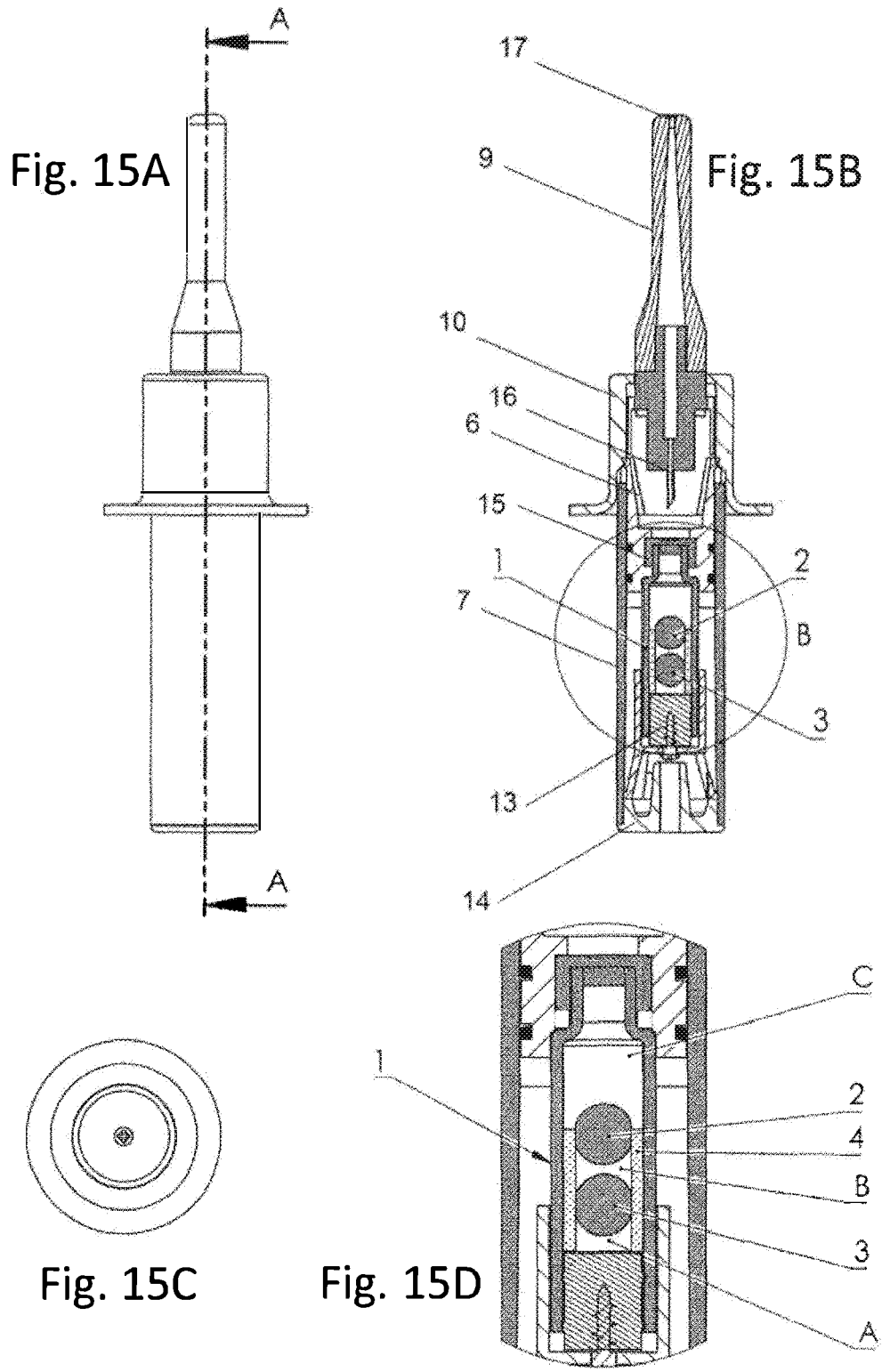

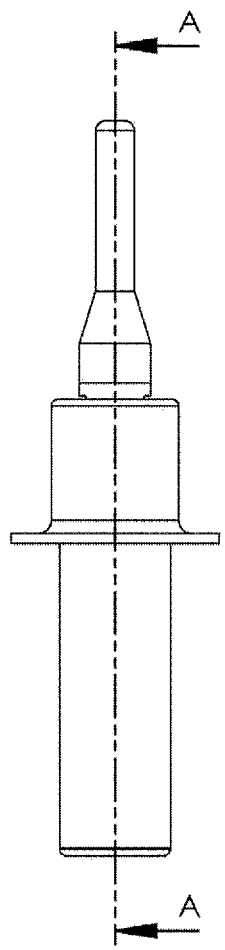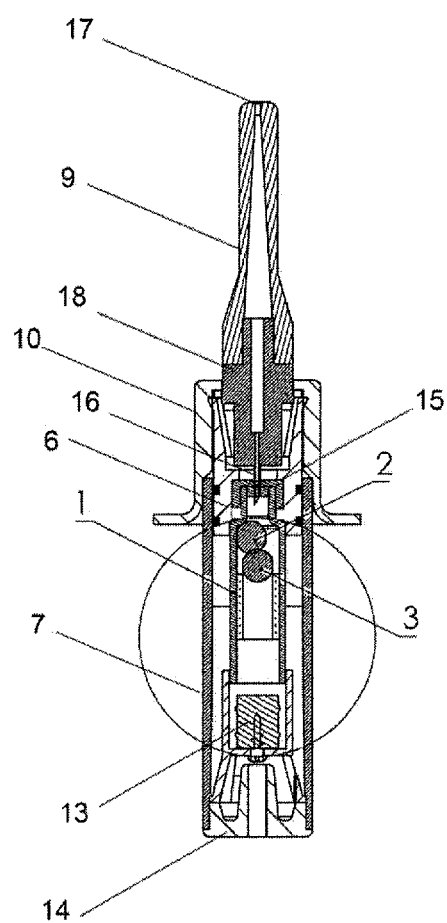
Fig. 16A  Fig. 16B
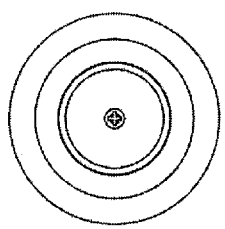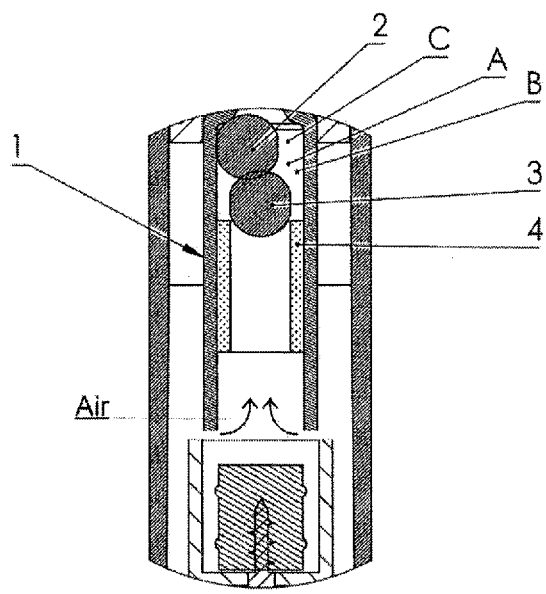
Fig. 16C  Fig. 16D

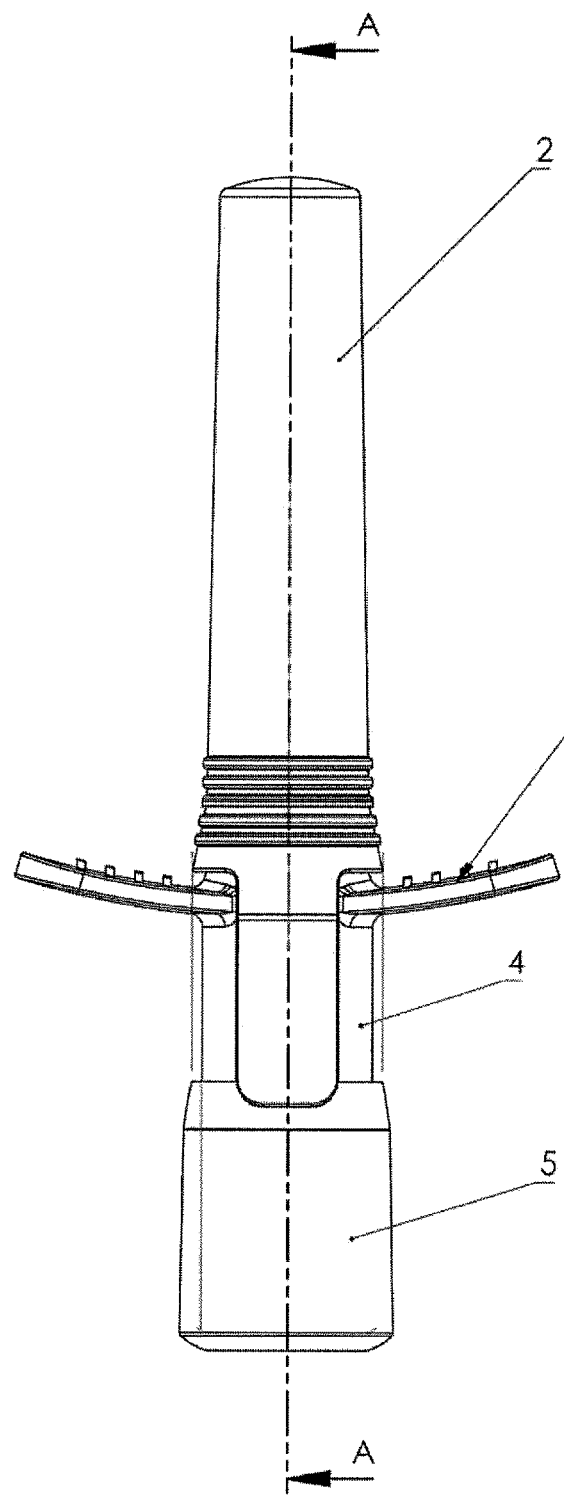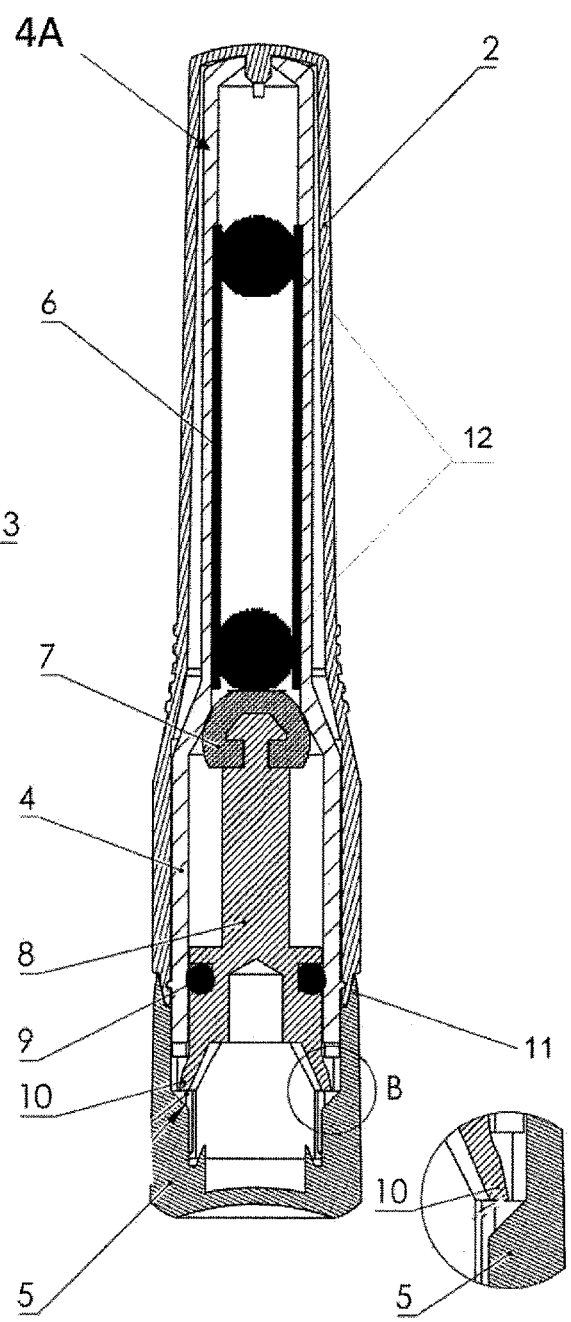
Fig. 19A
Fig. 19B SECTION A-A SCALE 2:1
Fig. 19C DETAIL B SCALE 4:1

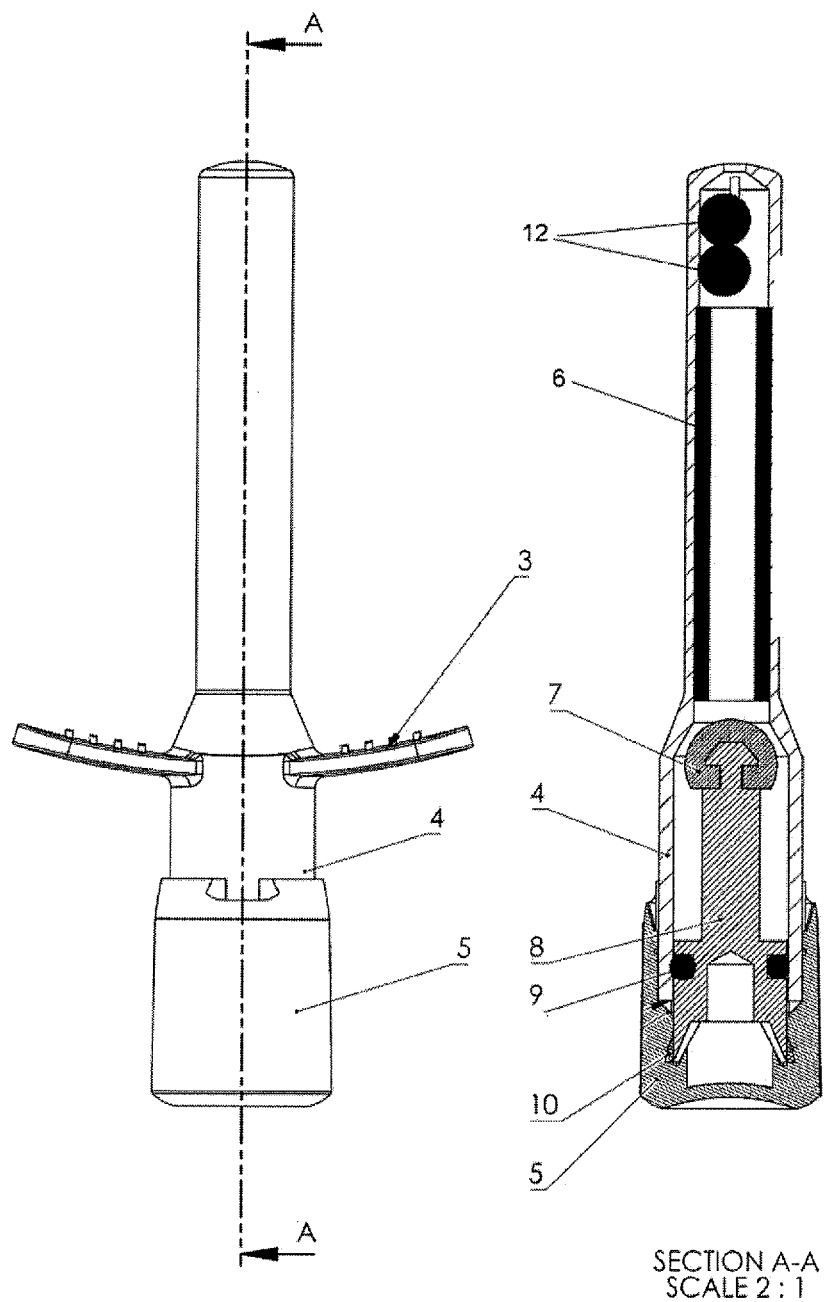

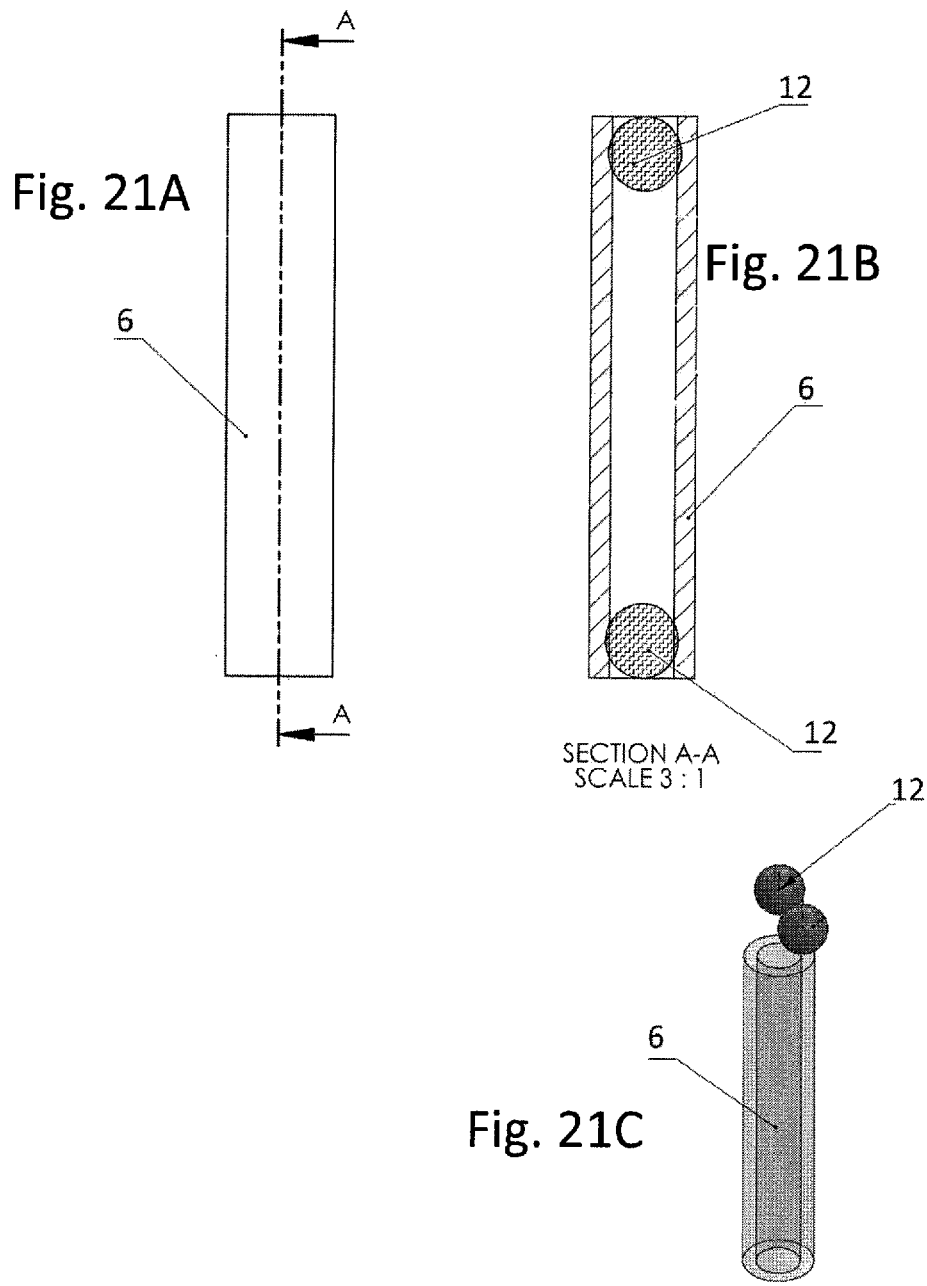

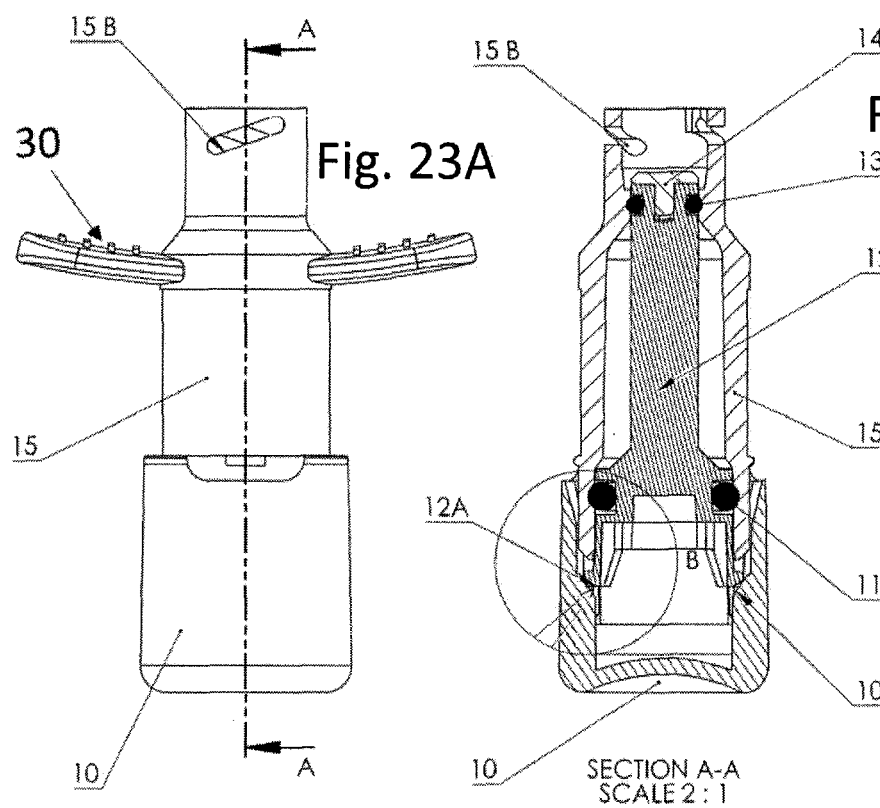
Fig. 23A
Fig. 23B
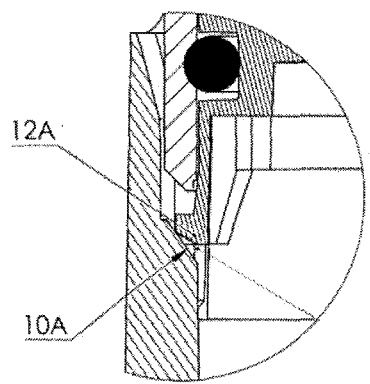
Fig. 23C
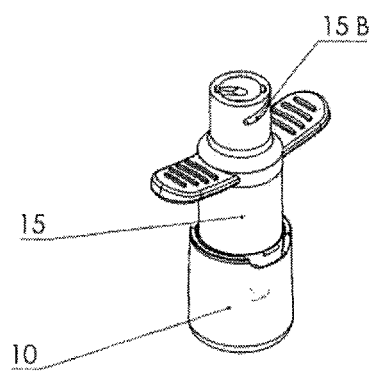
Fig. 23D

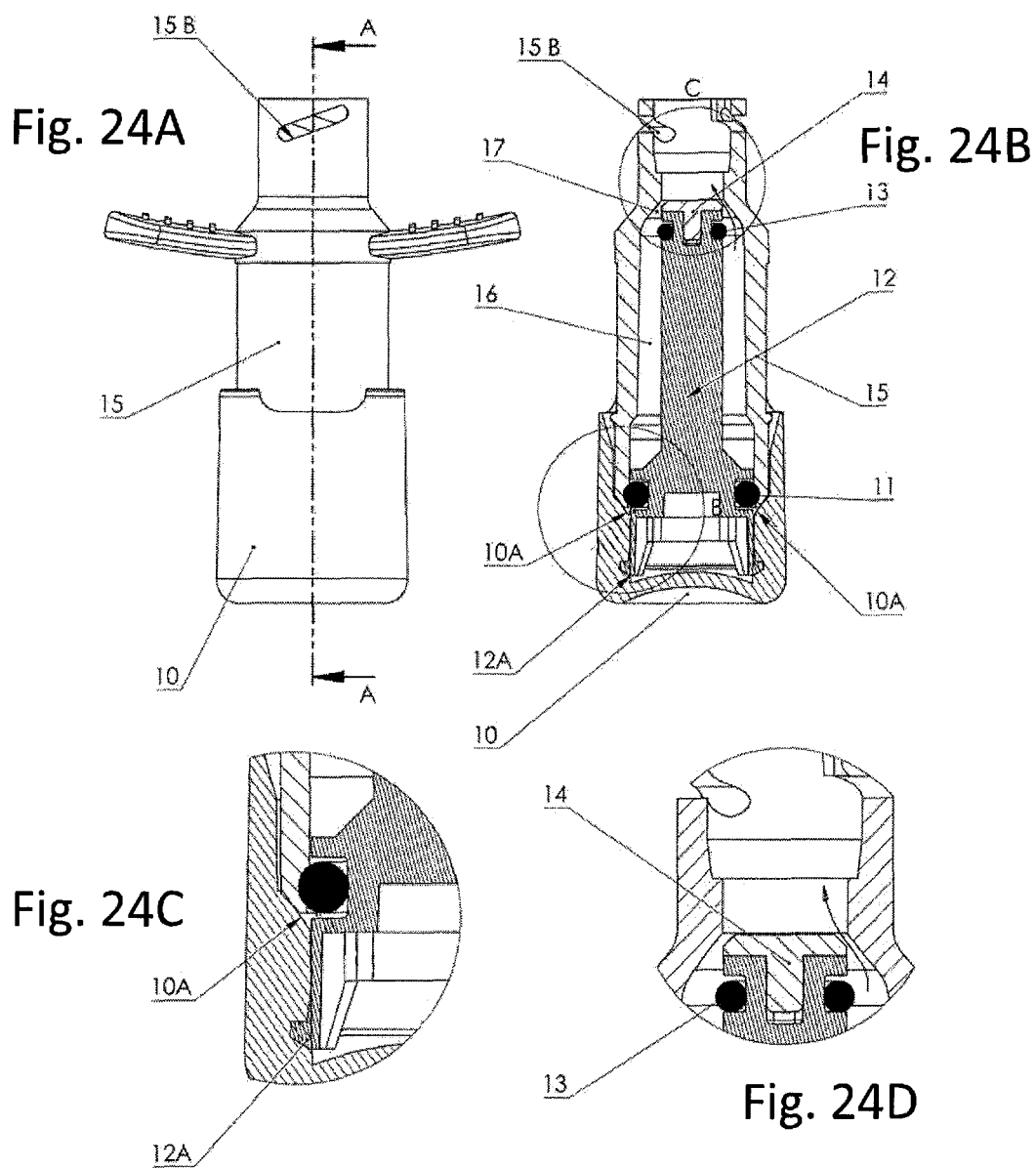

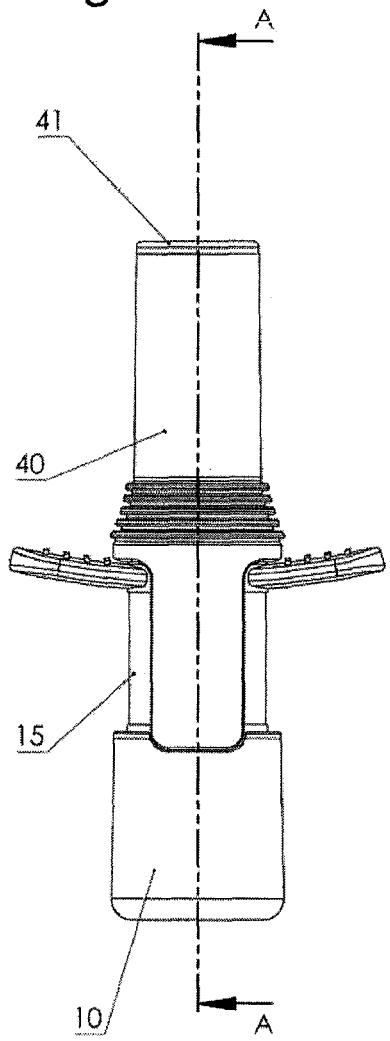
Fig. 28A
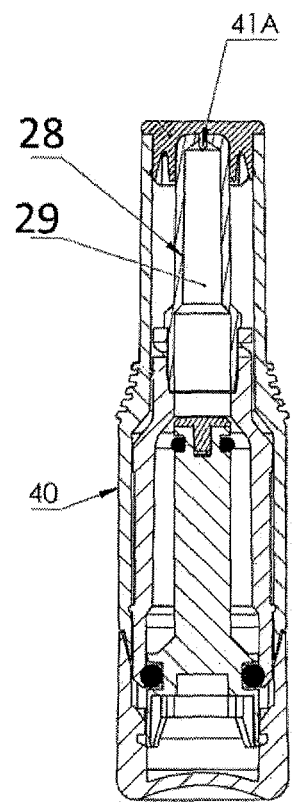
Fig. 28B
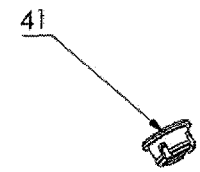
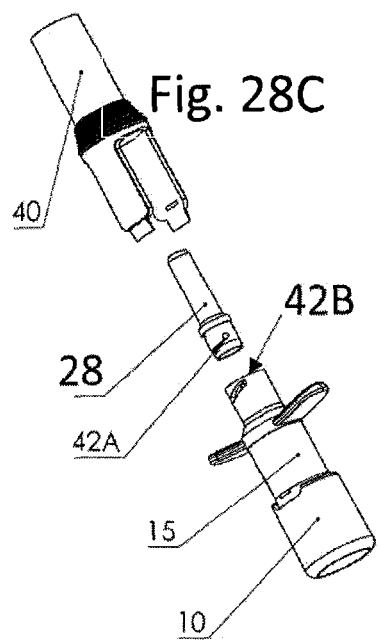
Fig. 28C
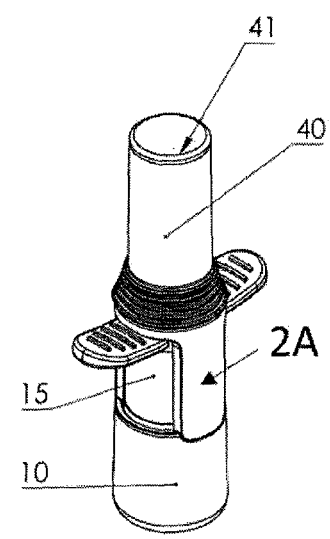
Fig. 28D

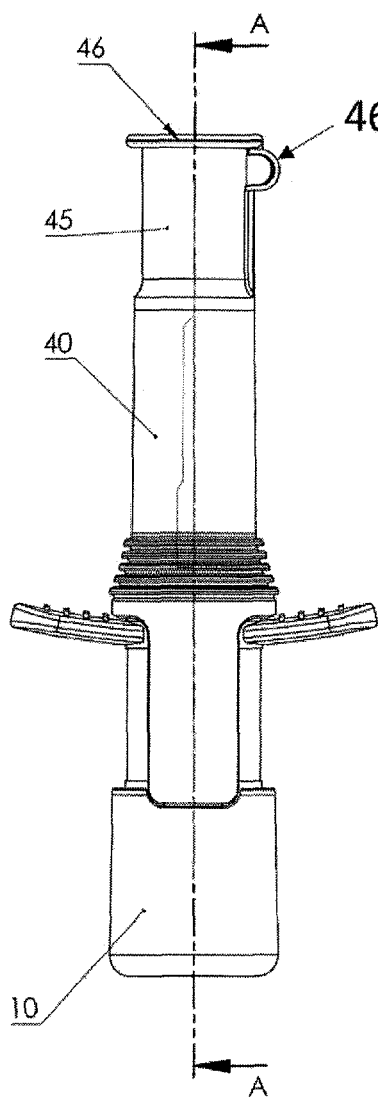
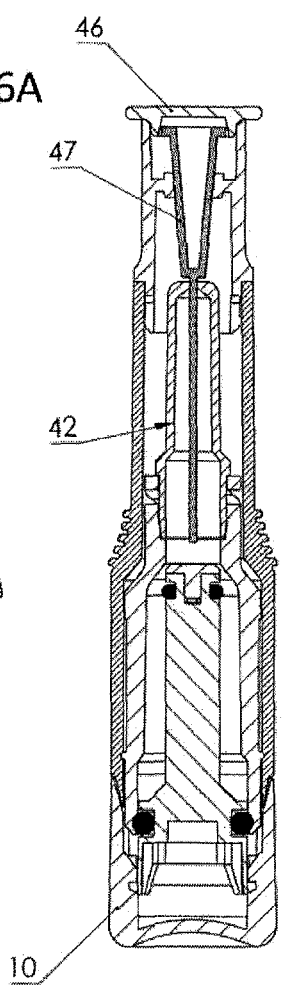
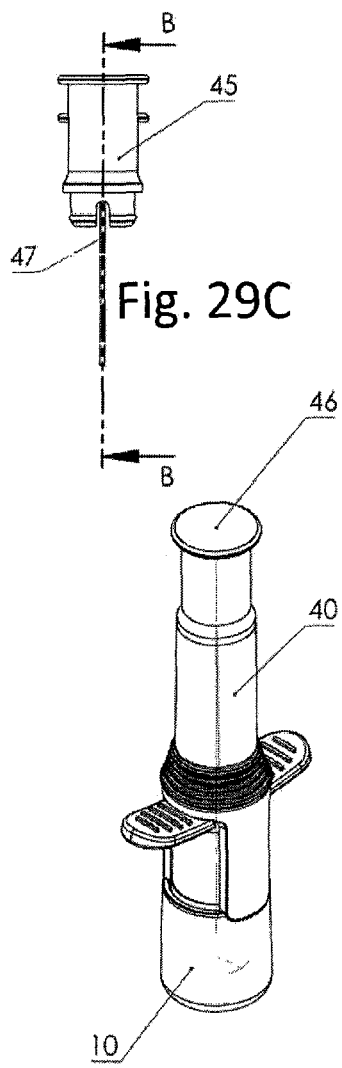
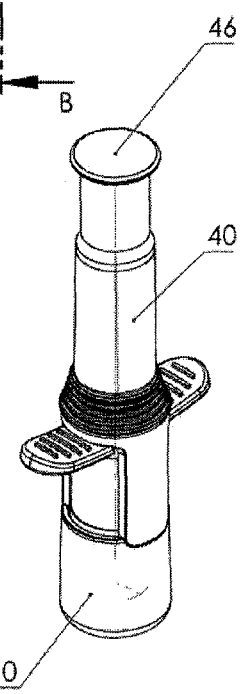
Fig. 29A　　　Fig. 29B　　　Fig. 29D

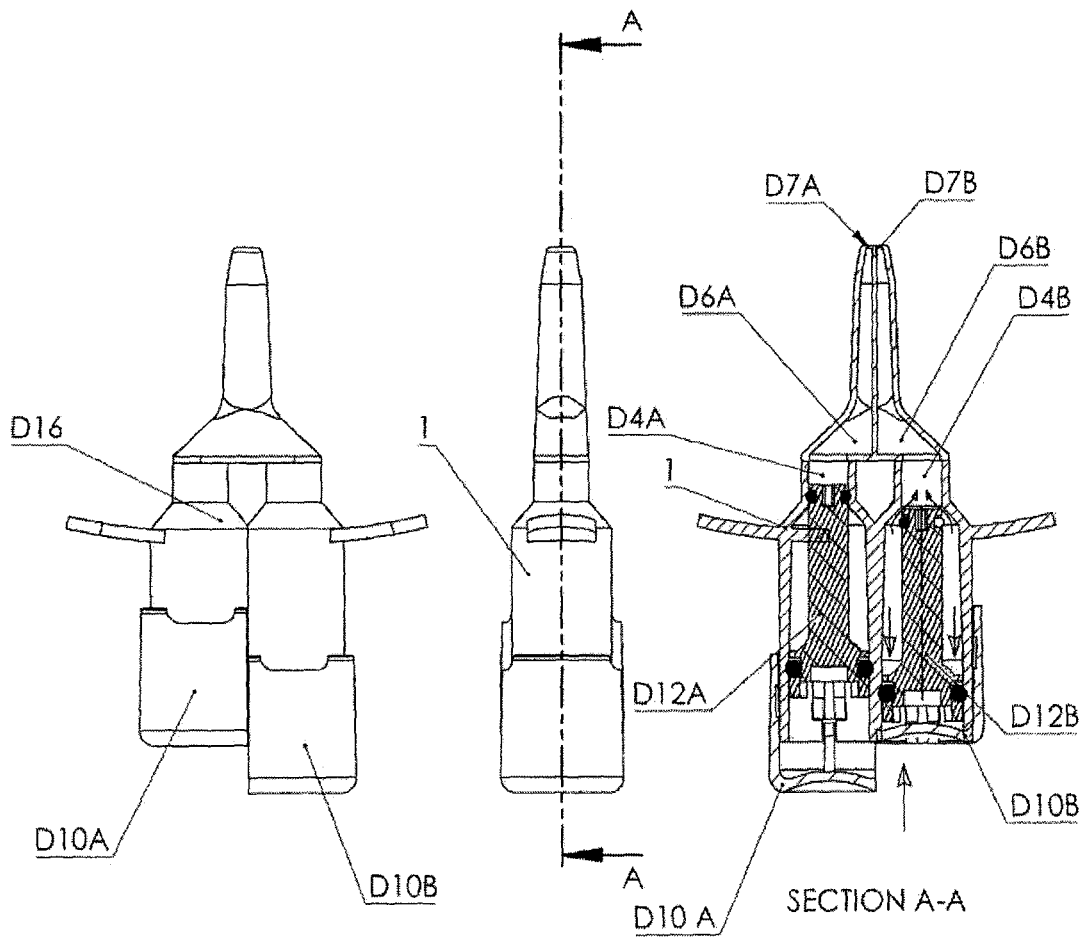
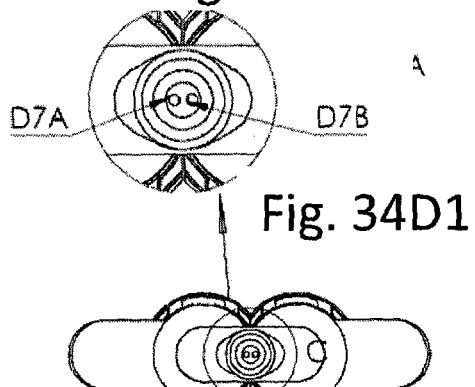
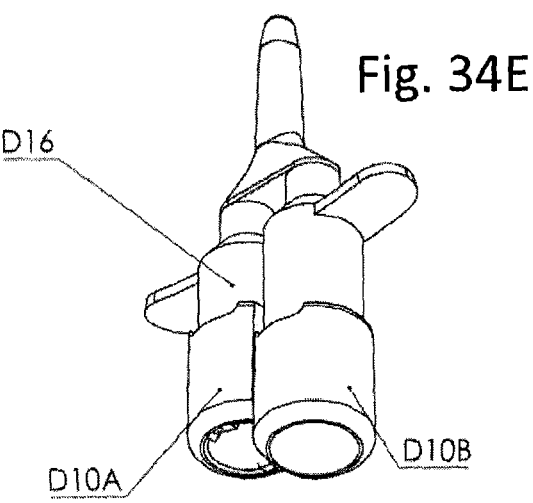
Fig. 34A    Fig. 34B    Fig. 34C
Fig. 34D1
Fig. 34D2
Fig. 34E

| Operating Conditions | Before Activation | After Activation |
|---|---|---|
| 1 | | |
| 2 | | |
| 3 | | |

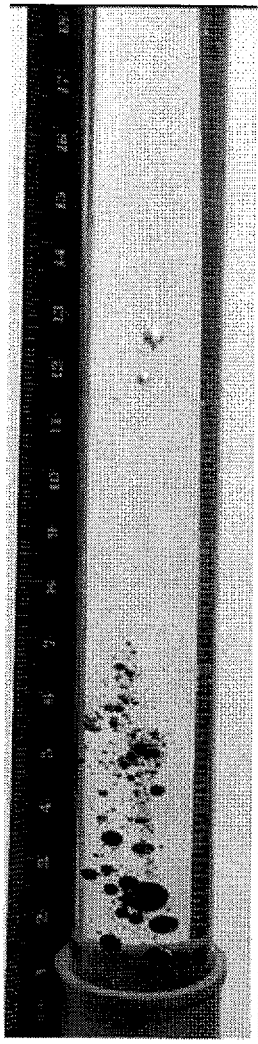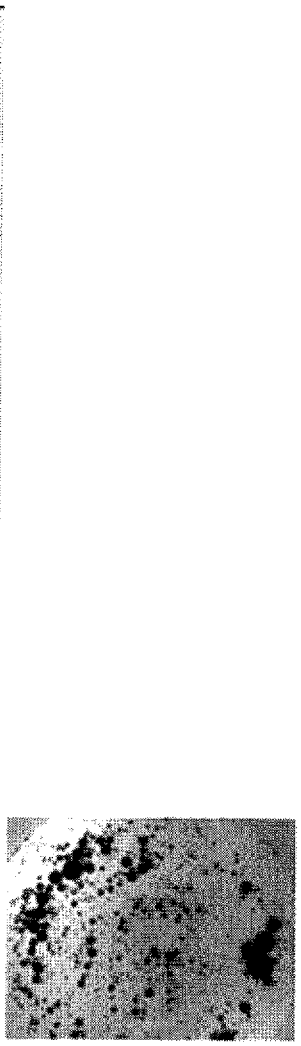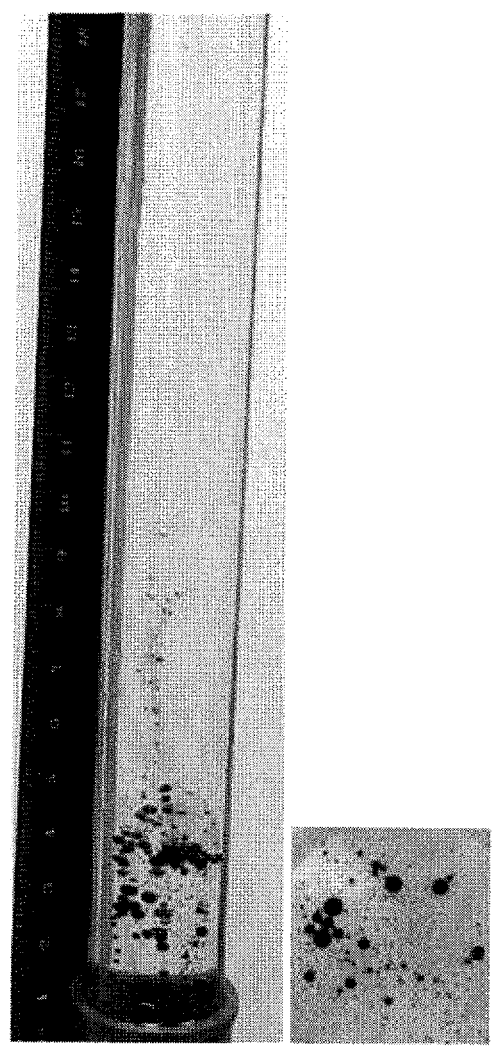
Fig. 37A    Fig. 37B        Fig. 37C    Fig. 37D

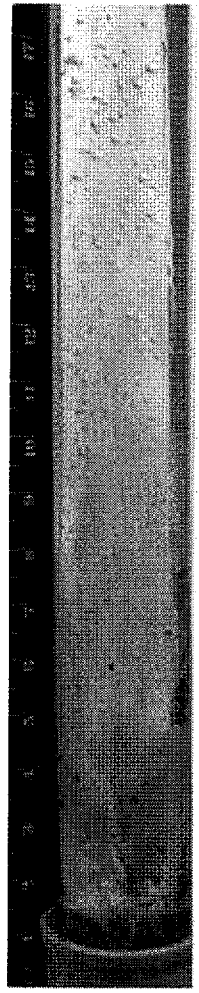
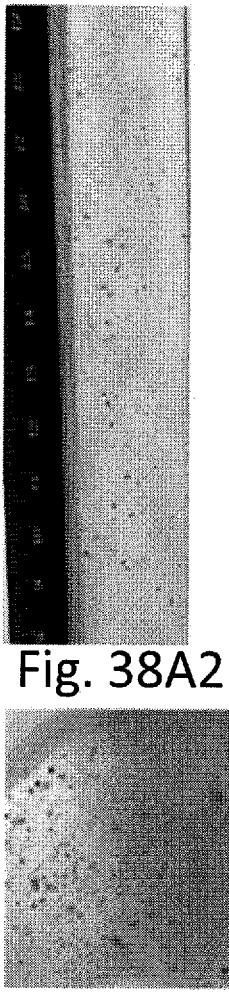
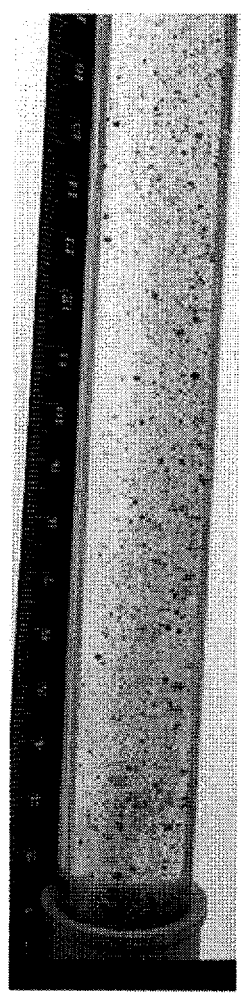
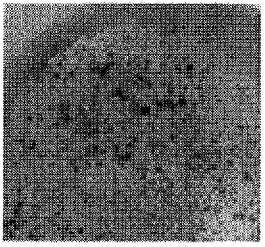
Fig. 38A2
Fig. 38A1   Fig. 38B        Fig. 38C   Fig. 38D

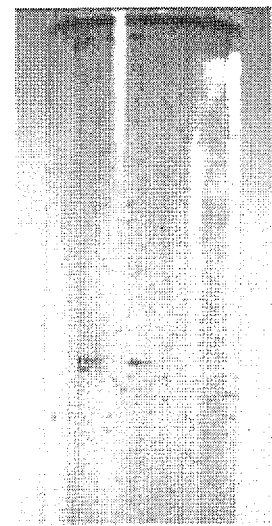
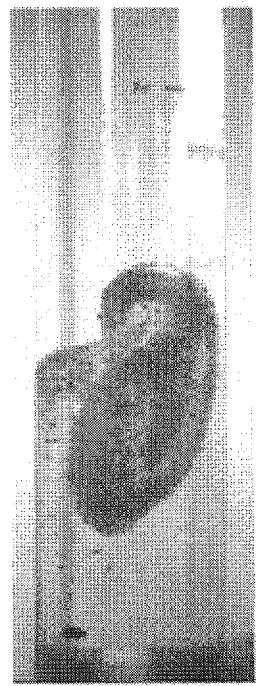 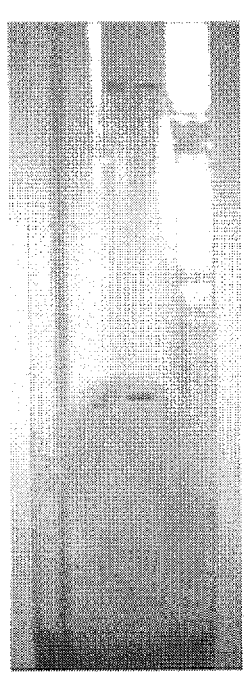 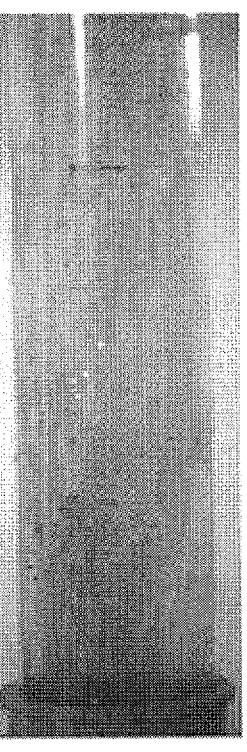
Fig. 40A    Fig. 40B    Fig. 40C

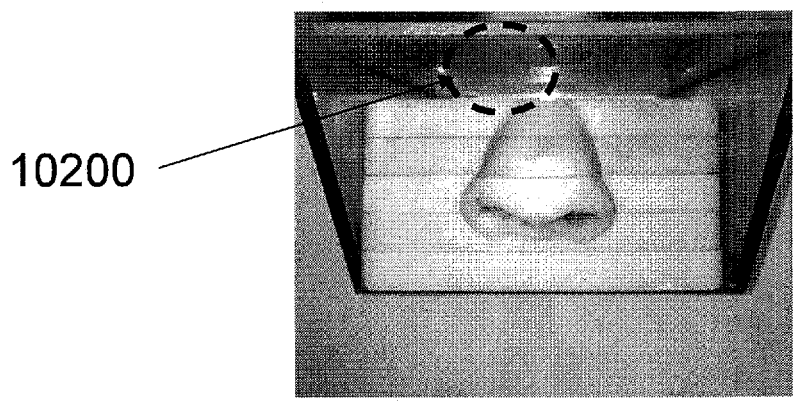
Fig. 43A
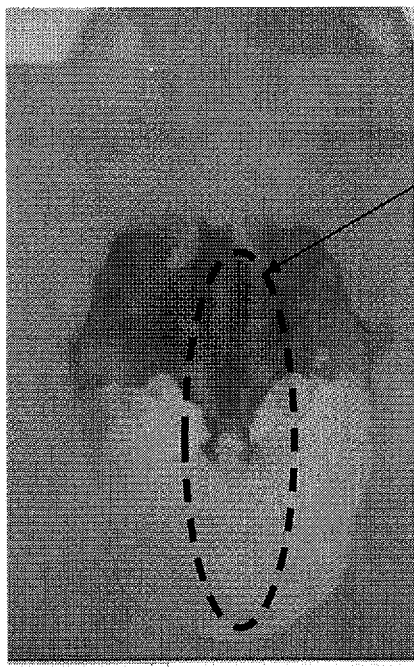 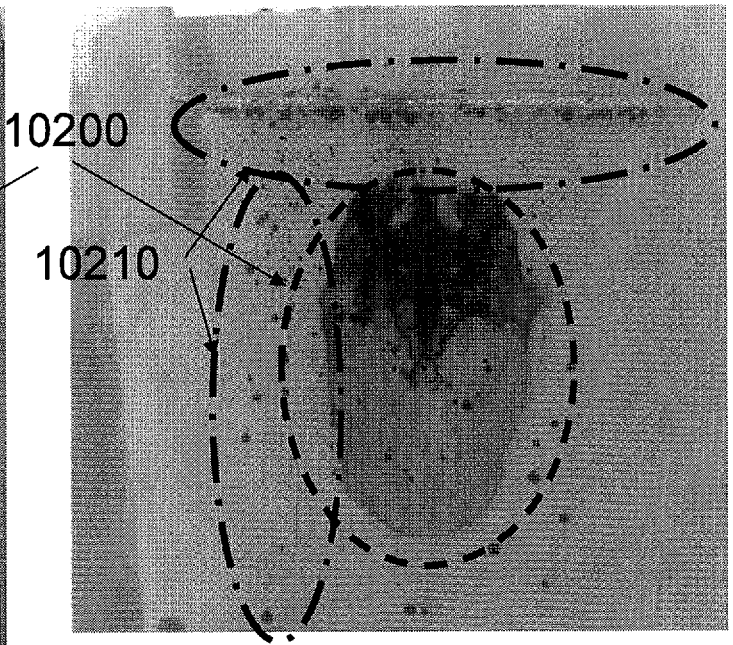
Fig. 43B                     Fig. 43C

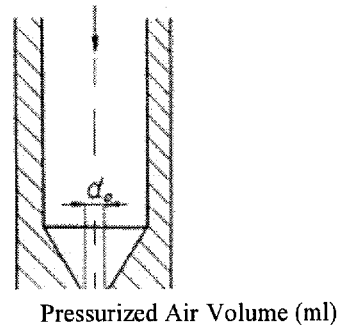
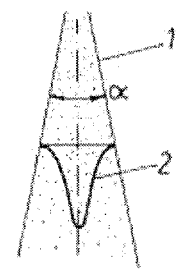
Fig. 44
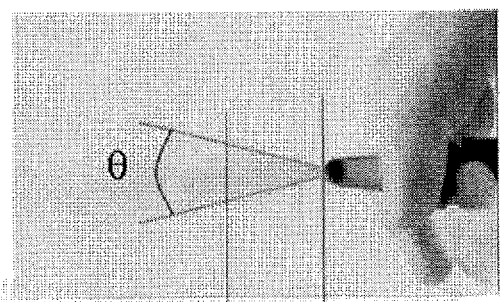 Fig. 45A  35°
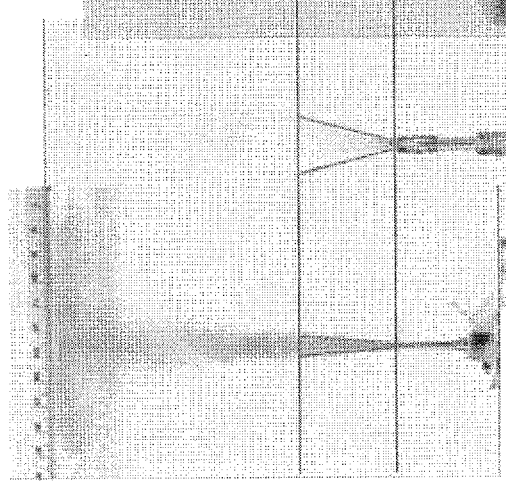 Fig. 45B  27°
Fig. 45C  8.7°

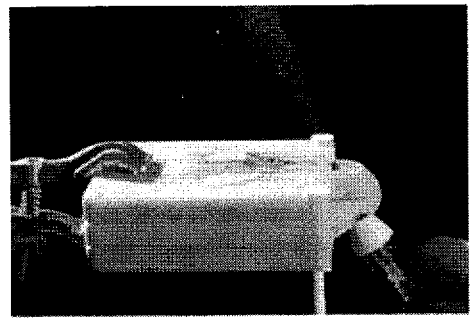 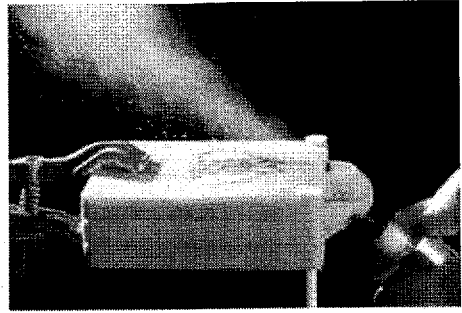
Fig. 46A   Fig. 46B
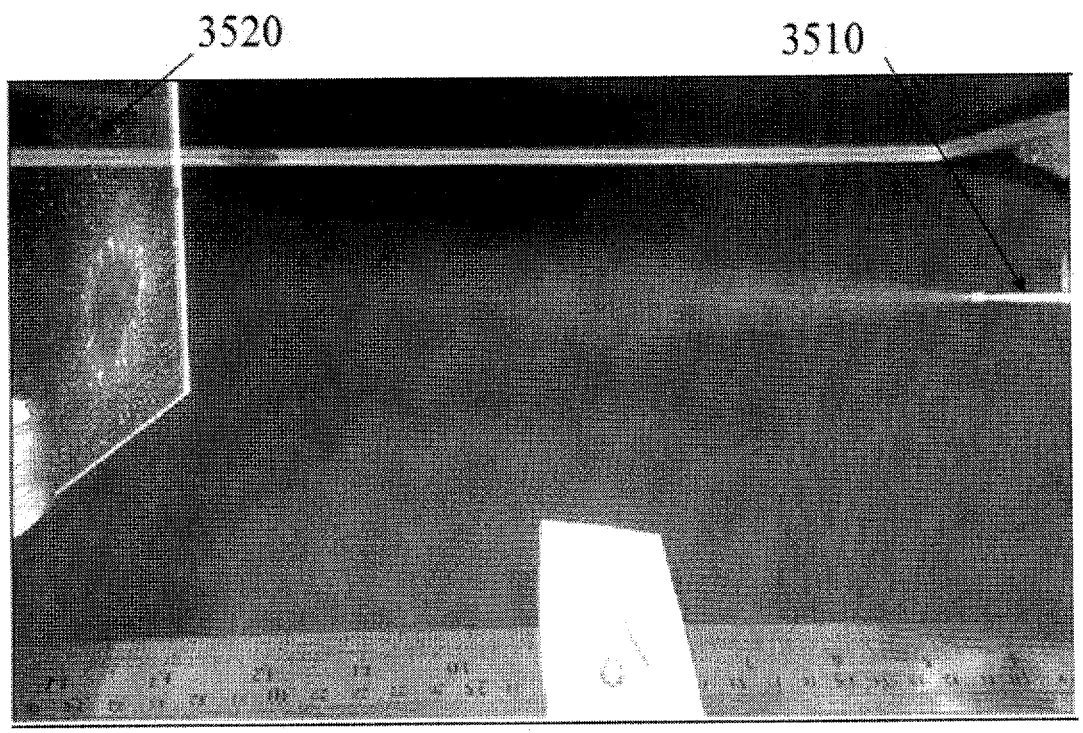
Fig. 47

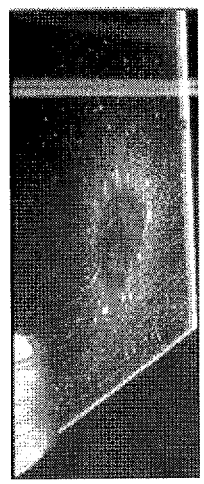 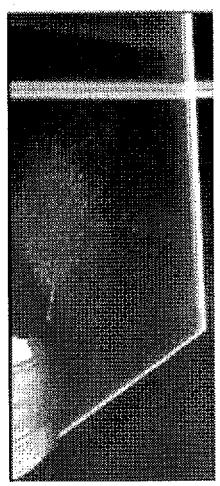 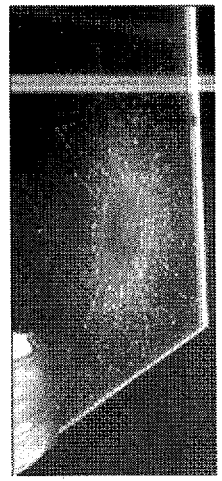 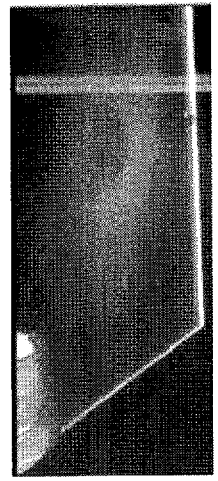 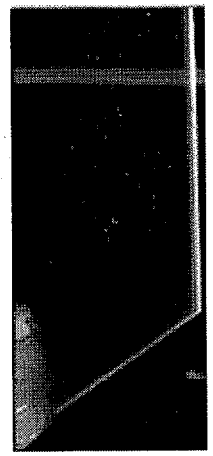
Fig. 48A  Fig. 48B  Fig. 48C  Fig. 48D  Fig. 48E
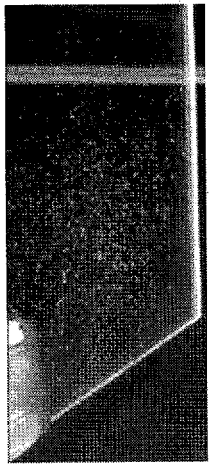 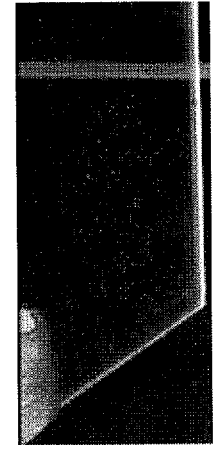 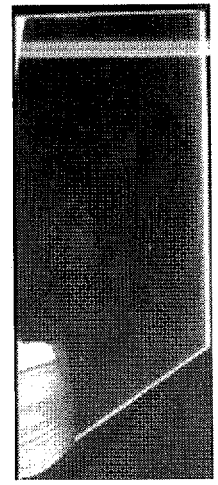 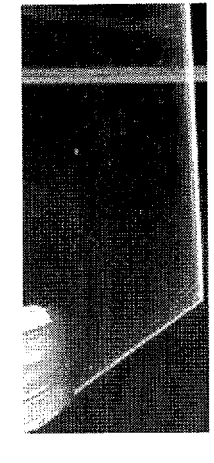 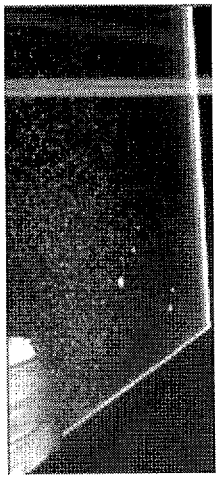
Fig. 48F  Fig. 48G  Fig. 48H  Fig. 48I  Fig. 48J
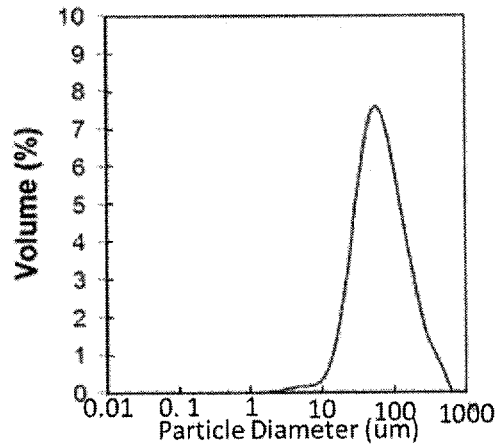
Fig. 49

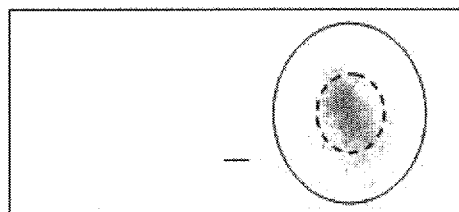
Fig. 50A
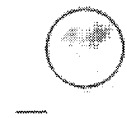
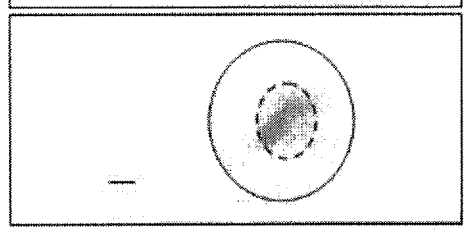
Fig. 50B
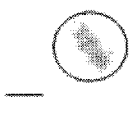
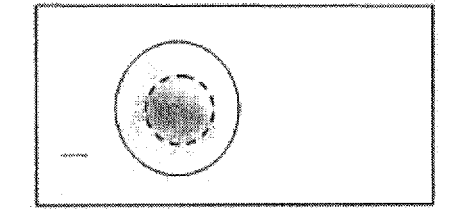
Fig. 50C
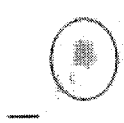
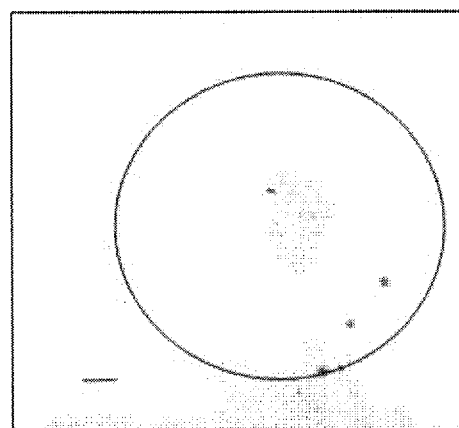
Fig. 50D
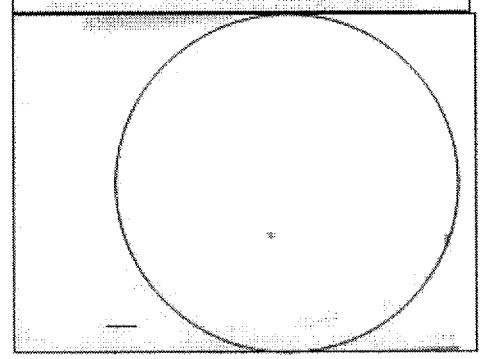
Fig. 50E

US 11,471,618 B2

ADJUSTABLE DOSING DELIVERY AND MULTI SECTIONED DRUG COMPARTMENT

FIELD OF THE INVENTION

The present invention generally pertains to a system for delivering aerosolized substance to a natural orifice of the body.

BACKGROUND OF THE INVENTION

In the pharmaceutical and therapeutic areas, nasal delivery is a known and acceptable delivery route that can provide a solution for a wide range of therapeutics and medical indications.

Prior art nasal delivery devices suffer from difficulties in: dose control, delivery accuracy, drug storage, and treatment with multiple medications. Metered dose delivery, where a fixed dose is released in every activation is common in nasal and aerosol delivery of pharmaceuticals. For metered dose delivery, each delivery device is designed to deliver a specific, unchangeable dose per activation. In some therapeutics areas, there is a need for a different dose for each patient, sometimes even for each therapeutic treatment for the same patient. For example: for the pediatric population, the dose often must depend on the weight of the patient. In other cases, such as acute treatment in cases of breakthrough seizures, breakthrough pain, or Parkinson's "off stage", the treatment should reflect the patient's medical condition.

Loading of a desirable dose to fit a specific need is not common in nasal delivery applications, moreover, one of the main obstacles to providing an adjustable dose in nasal delivery devices, especially when released in the form of an aerosol, is maintaining, over a wide range of dose sizes, reproducible aerosol characteristics in terms of dose released, residual volume, droplet diameter, droplet size distribution and plume geometry.

In many therapeutic areas there is a need to provide the patient with a number of medications during the same treatment. With oral delivery, a patient can consume different pills one after the other, or consume one pill that contains more than one active ingredient/drug (For example: L-Dopa+Carbidopa; Topiramate+Phentermine (like in Qsymia) and more. In injectable and nasal delivery, the ability to mix compounds before or at the time of administration is less common.

In some cases there is a need to store compounds and materials separately in order to maintain stability and functionality. This can conflict with a need to deliver the compounds in a specialized formulation for better user experience and/or better absorption. For example, a drug which is a biologic or protein or an active compound that is not stable in solution can be highly stable as a dry powder. For such drugs, mixture of the dry powder drug with a liquid formations at the time of administration, could provide a homogenous solution to be delivered efficiently to the target tissue. User compliance could be high, since it is effective and provides a positive user experience. Another example is an insoluble compound that is stored in one compartment and is released with, slightly before or slightly after a formulation that will either affect the spread of the compound in the target tissue, or improve the absorption of the compound via the mucosal tissue, or change the adhesion of the compound to the mucosal tissue (to lengthen or shorten the exposure of the mucosal tissue to the compound, or, the formulation can protect the active compound from degradation and/or clearance. However, in the prior art there is no way to provide both long-term separate storage for components of a formulation and automatic mixing of the components at the time of administration.

It is therefore a long felt need to provide a system which can be optimized for efficient delivery of a substance to a target site, said optimization neglecting neither the need to bring sufficient material to the target site, nor the need to ensure adequate absorption into and through the mucosal layer.

SUMMARY OF THE INVENTION

It is an object of the present invention to disclose a system and method for delivering aerosolized substance to a natural orifice of the body It is another object of the present invention to disclose a device for delivering a predetermined volume $V_{sub}$ [ml] of at least one substance, within at least one body cavity of a subject, the device comprising:
a. at least one predefined volume sized and shaped for containing said predetermined volume $V_{sub}$ [ml] of at least one substance;
b. a delivery end for placement in proximity to the body cavity, the delivery end being in fluid communication with the container; the delivery end comprising at least one orifice of diameter D [mm];
c. at least one valve mechanically connectable to the container, characterized by at least two configurations: (i) an active configuration in which the valve enables delivery of a predetermined volume $V_{sub}$ [ml] of the substance from the container to the body cavity via the delivery end; and, (ii) an inactive configuration, in which the valve prevents delivery of the predetermined volume $V_{sub}$ [ml] of the substance from the container to the body cavity;
the valve is reconfigurable from the inactive configuration to the active configuration, and vice versa, within a predetermined period of time, dT, in response to activation of the same; and
d. a fluid tight chamber configured to contain a predetermined volume $V_{gas}$ [ml] of pressurized gas at a predetermined pressure, $P_{gas}$ [barg];
the device is configured, once the valve is reconfigured from the inactive configuration to the active configuration, to entrain the substance by the pressurized gas, and deliver the same via the orifice in the delivery end within the body cavity;
wherein the device is configured to deliver the predetermined volume $V_{sub}$ [ml] of the substance and the predetermined volume $V_{gas}$ of the pressurized gas through the orifice of diameter D [mm] in (a) pressure rate of $dP_{gas}/dT$; (b) volume rate of $dV_{gas}/dT$; and (c) volume rate of $dV_{sub}/dT$;
further wherein at least one of the following is held true:
(a) $P_{gas}$ is in the range of about 1-10 barg;
(b) $V_{gas}$ is in the range of about 1-21 ml;
(c) $V_{sub}$ is in the range of about 0.01-7 ml;
(d) D is in the range of 0.2-6 mm;
(e) the pressure rate, $$\frac{dP}{dT} \to \infty;$$

(f) the pressure rate $dP_{gas}/dT$ is greater than about 0.001 barg/ms;
(g) the volume rate $dV_{sub}/dT$ is greater than about 0.0001 ml/ms;

(h) the volume rate $dV_{gas}/dT$ is greater than about 0.001 ml/ms;

(i) the predetermined period of time, $dT \to 0$; and (j) dT is in the range of about 0 to 500 millisecond.

It is another object of the present invention to disclose the device, wherein at least one of the following is true:

a. said device is configured for a plurality of deliveries of said predetermined volume $V_{sub}$, said predetermined volume $V_{sub}$ being controllably alterable;

b. the body orifice is a nasal cavity, the mouth, the throat, an ear, the vagina, the rectum, the urethra, and any combination thereof c. viscosity $\eta$ of the substance is in the range of about $1 \times 10^{-3}$ poise to about 1 poise;

d. DV50 diameter of particles of the substance, after exit from said device, is less than about 100 μm;

e. DV90 diameter of the particles is less than about 1000 μm;

f. a full width of a plume of aerosol comprising said substance and said gas subtends an angle θ of less than about 25°;

g. particles in the plume have velocities in a range of about 5 m/s to 50 m/s;
h. the pressurized gas comprises air, nitrogen, oxygen, carbon dioxide, helium, neon, xenon and any combination thereof;
i. during dispensing of the at least one substance, a mixture of the predetermined volume $V_{gas}$ [ml] of the pressurized gas and the predetermined volume $V_{sub}$ [ml] of the substance entrained within it forms a plume of aerosol; the aerosol having a predetermined distribution, the distribution being either homogeneous or heterogeneous, the heterogeneous distribution is selected from a group consisting of: an arbitrary distribution, a distribution in which the density of at least one substance within the mixture follows a predetermined pattern, and any combination thereof; characteristics of the aerosol selected from a group consisting of: particle size, particle shape, particle distribution, and any combination thereof, are determinable from characteristics of the device selected from a group consisting of: the predetermined volume of the pressurized gas, the predetermined volume of the substance, the predetermined pressure of the pressurized gas, the predetermined orifice size, and any combination thereof;
j. at least one substance is selected from a group consisting of a gas, a liquid, a powder, an aerosol, a slurry, a gel, a suspension and any combination thereof; and
k. at least one substance is stored under either an inert atmosphere or under vacuum to prevent reactions during storage.

It is another object of the present invention to disclose the device, wherein said volume is a container.

It is another object of the present invention to disclose the device, wherein the container is a capsule having a main longitudinal axis, the container comprising a number n of compartments, the container configured to contain the predetermined volume $V_{sub}$ [ml] of the at least one substance, the volume $V_{sub}$ [ml] of the at least one substance containable in at least one of the n compartments; at least one of the following being true:

a. the container is a capsule;
b. the number n of compartments is an integer greater than or equal to 1; at least one compartment has cross-section with shape selected from a group consisting of: wedge shaped, circular, oval, elliptical, polygonal, annular, and any combination thereof;
c. for the number n of compartments being an integer greater than 1, at least two compartments have different volumes;
d. for the number n of compartments being an integer greater than 1, at least two compartments have the same volume;
e. for the number n of compartments being an integer greater than 1, at least two compartments have different cross-sectional areas;
f. for the number n of compartments being an integer greater than 1, at least two compartments have the same cross-sectional area;
g. for the number n of compartments being an integer greater than 1, at least two compartments contain different substances;
h. for the number n of compartments being an integer greater than 1, at least two compartments contain the same substance;
i. for the number n of compartments being an integer greater than 1, at least two compartments are disposed coaxially around the main longitudinal axis of the capsule;
j. for the number n of compartments being an integer greater than 1, at least two compartments are disposed sequentially along the main longitudinal axis of the capsule;
k. for the number n of compartments greater than 1, the plurality of substances mix during dispensing; and
l. for the number n of compartments greater than 1, the plurality of substances react during dispensing.

It is another object of the present invention to disclose the device, wherein the container comprises a port fluidly connectable to the exterior of the device, the port configured such that at least one substance is insertable into the chamber via the port.

It is another object of the present invention to disclose the device, wherein the device comprises a port cover configured to provide an air-tight closure for the port, the port cover slidable along the device, rotatable around the device, rotatable around a hinge on the exterior of the device and any combination thereof.

It is another object of the present invention to disclose a device for delivering a predetermined amount $M_{sub}$ [mg] of at least one substance within at least one body cavity of a subject, the device comprising:

a. at least one predefined volume sized and shaped for containing the predetermined amount $M_{sub}$ [mg] of the at least one substance;
b. a delivery end for placement in proximity to the body cavity, the aid delivery end being in fluid communication with the container; the delivery end comprising at least one orifice of diameter D [mm];
c. at least one valve mechanically connectable to the container, characterized by at least two configurations: (i) an active configuration in which the valve enables delivery of a predetermined amount $M_{sub}$ [mg] of the substance from the container to the body cavity via the delivery end; and, (ii) an inactive configuration, in which the valve prevents delivery of the predetermined amount $M_{sub}$ [mg] of the substance from the container to the body cavity; the valve is reconfigurable from the inactive configuration to the active configuration, and vice versa, within a predetermined period of time, dT, in response to activation of the same; and
d. a fluid tight chamber configured to contain a predetermined volume $V_{gas}$ [ml] of pressurized gas at a predetermined pressure, $P_{gas}$ [barg];

the device is configured, once the valve is reconfigured from the inactive configuration to the active configuration, to entrain the substance by the pressurized gas, and deliver the same via the orifice in the delivery end within the body cavity;

wherein the device is configured to deliver the predetermined amount $M_{sub}$ [mg] of the substance and the predetermined volume $V_{gas}$ of the pressurized gas through the orifice of diameter D [mm] in a pressure rate of $dP_{gas}/dT$;

further wherein at least one of the following is held true:
(a) $P_{gas}$ is in the range of about 1-10 barg;
(b) $V_{gas}$ is in the range of about 1-21 ml;
(c) $M_{sub}$ is in the range of about 0.01-1000 mg;
(d) D is in the range of 0.2-6 mm;
(e) the pressure rate, $$\frac{dP}{dT} \to \infty;$$

(f) the pressure rate is greater than about 0:001 barg/ms;
(g) the amount rate $dM_{sub}/dT$ is greater than about 0.0001 mg/ms;
(h) the volume rate $dV_{gas}/dT$ is greater than about 0.001 ml/ms;
(i) the predetermined period of time, $dT \to 0$; and
(j) dT is in the range of about 0 to 500 millisecond.

It is another object of the present invention to disclose the device, wherein at least one of the following is true:
a. said device is configured for a plurality of deliveries of said predetermined amount $M_{sub}$, said predetermined amount $M_{sub}$ being controllably alterable;
b. the body orifice is a nasal cavity, the mouth, the throat, an ear, the vagina, the rectum, the urethra, and any combination thereof;
c. viscosity η of the substance is in a range of about $1 \times 10^{-3}$ poise to about 1 poise.
d. DV50 diameter of particles of the substance, after exit from the device, is less than about 100 μm;
e. DV90 diameter of the particles of the substance, after exit from the device, is less than about 1000 μm;
the full width of the plume of aerosol comprising the substance and the gas subtends an angle θ of less than about 25°;
g. particles in the plume have velocities in the range of about 5 m/s to 50 m/s;
h. the pressurized gas comprises air, nitrogen, oxygen, carbon dioxide, helium, neon, xenon and any combination thereof
i. during dispensing of the at least one substance, a mixture of the predetermined volume $V_{gas}$ [ml] of the pressurized gas with the predetermined mass $M_{sub}$ [mg] of the substance entrained within it forms a plume of aerosol, the aerosol having a predetermined distribution, the distribution being either homogeneous or heterogeneous, the heterogeneous distribution is selected from a group consisting of: an arbitrary distribution, a distribution in which the density of the at least one substance within the mixture follows a predetermined pattern, and any combination thereof; characteristics of the aerosol selected from a group consisting of: particle size, particle shape, particle distribution, and any combination thereof, are determinable from characteristics of the device selected from a group consisting of: predetermined volume of the pressurized gas, predetermined volume of the substance, predetermined pressure of the pressurized gas, predetermined orifice size, and any combination thereof;
j. at least one substance is selected from a group consisting of a gas, a liquid, a powder, an aerosol, a slurry, a gel, a suspension and any combination thereof;
k. at least one substance is stored under either an inert atmosphere or under vacuum to prevent reactions during storage; and
l. a dose-response curve is substantially linear for brain concentration of the substance when administered nasally via the device;
m. a dose-response curve for brain concentration having a fit selected from a group consisting of logarithmic, parabolic, exponential, sigmoid, power-low, and any combination thereof; of said substance when administered nasally via said device.

It is another object of the present invention to disclose the device, wherein said volume is a container.

It is another object of the present invention to disclose the device, wherein the container is a capsule having a main longitudinal axis, the capsule comprising a number n of compartments, the capsule configured to contain the predetermined mass $M_{sub}$ [mg] of the at least one substance, the mass $M_{sub}$ [mg] of the at least one substance containable in at least one of the n compartments; at least one of the following being true:
a. the container is a capsule;
b. the number n of compartments is an integer greater than or equal to 1; at least one compartment has cross-section with shape selected from a group consisting of: wedge shaped, circular, oval, elliptical, polygonal, annular, and any combination thereof;
c. for the number n of compartments being an integer greater than 1, at least two compartments have different volumes;
d. for the number n of compartments being an integer greater than 1, at least two compartments have the same volume;
e. for the number n of compartments being an integer greater than 1, at least two compartments have different cross-sectional areas;
f. for the number n of compartments being an integer greater than 1, at least two compartments have the same cross-sectional area;
gf. for the number n of compartments being an integer greater than 1, at least two compartments contain different substances;
h. for the number n of compartments being an integer greater than 1, at least two compartments contain the same substance;
i. for the number n of compartments being an integer greater than 1, at least two compartments are disposed coaxially around the main longitudinal axis of the capsule;
j. for the number n of compartments being an integer greater than 1, at least two compartments are disposed sequentially along the main longitudinal axis of the capsule;
k. for the number n of compartments greater than 1, the plurality of substances mix during dispensing; and
l. for the number n of compartments greater than 1, the plurality of substances react during dispensing.

It is another object of the present invention to disclose the device, wherein the container comprises a port fluidly connectable to the exterior of the device, the port configured such that a substance is insertable into the chamber via the port.

It is another object of the present invention to disclose the device, wherein the device comprises a port cover configured to provide an air-tight closure for the port, the port cover slidable along the device, rotatable around the device, rotatable around a hinge on the exterior of the device and any combination thereof.

It is another object of the present invention to disclose a method of delivering a predetermined volume $V_{sub}$ [ml] of at least one substance within at least one body cavity of a subject, comprising:
a. providing a device comprising:
  i. a least one predefined volume sized and shaped for containing the predetermined volume $V_{sub}$ [ml] of the at least one substance;
  ii. a delivery end in fluid communication with the container; the delivery end comprising at least one orifice of diameter D [mm];
  iii. at least one valve mechanically connected to the container, characterized by at least two configurations: (i) an active configuration in which the valve enables delivery of the predetermined volume $V_{sub}$ [ml] of the substance from the container to the body cavity via the delivery end; and, (ii) an inactive configuration, in which the valve prevents delivery of the predetermined volume $V_{sub}$ [ml] of the substance from the container to the body cavity;
    the valve is reconfigurable from the inactive configuration to the active configuration, and vice versa, within a predetermined period of time, dT, in response to activation of the same; and
  iv. a fluid tight chamber configured to contain predetermined volume $V_{gas}$ [ml] of pressurized gas at a predetermined pressure, $P_g$. [barg];
b. emplacing the substance in the predefined volume;
c. setting the valve in the inactive configuration;
d. pressurizing the fluid-tight chamber with the gas to the predetermined pressure;
e. placing the delivery end in proximity to the body cavity;
f. reconfiguring the valve from the inactive configuration to the active configuration thereby entraining the substance in the predetermined volume $V_{gas}$ of the pressurized gas; thereby
g. delivering the predetermined volume $V_{sub}$ [ml] of the substance and the predetermined volume $V_{gas}$ of the pressurized gas through the orifice of diameter D [mm] in a pressure rate of $dP_{gas}/dT$;
wherein at least one of the following is held true:
(a) $P_{gas}$ is in the range of about 1-10 barg;
(b) $V_{gas}$ is in the range of about 1-21 ml;
(c) $V_{sub}$ is in the range of about 0.01-7 ml;
(d) D is in the range of 0.2-6 mm;
(f) the pressure rate, $$\frac{dP}{dT} \to \infty;$$

(g) the pressure rate is greater than about 0.001 barg/ms;
(h) the volume rate $dV_{sub}/dT$ is greater than about 0.0001 ml/ms;
(i) the volume rate $dV_{gas}/dT$ is greater than about 0.001 ml/ms;
(j) the predetermined period of time, $dT \to 0$; $dT \to 0$; and
(k) dT is in the range of about 0 to 500 millisecond.

It is another object of the present invention to disclose the method, additionally comprising at least one of the following steps:
a. generating a plurality of deliveries of said predetermined volume $V_{sub}$, and controllably altering said predetermined volume $V_{sub}$;

b. selecting the body orifice from a group consisting of a nasal cavity, the mouth, the throat, an ear, the vagina, the rectum, the urethra, and any combination thereof;
c. selecting viscosity η of the substance to be in the range of about $1 \times 10^{-3}$ poise to about 1 poise;
d. characterizing particles of said substance in a delivered aerosol, said aerosol a mixture of said at least one substance and said gas, by a DV50 diameter, said DV50 diameter being less than about 100 μm;
e. characterizing said particles by a DV90 diameter of less than about 1000 μm;
f. characterizing a plume of said aerosol by a plume angle θ, said plume angle θ subtending the full width of said plume, said plume angle θ subtending an angle of less than about 25°;
g. characterizing velocities of particles in said plume as being in a range of about 5 m/s to 50 m/s;
h. selecting said gas from a group consisting of: air, nitrogen, oxygen, carbon dioxide, helium, neon, xenon and any combination thereof;
i. dispensing said at least one substance, and during said step of dispensing, forming a plume of aerosol with predetermined distribution from a mixture of the predetermined volume $V_{gas}$ [ml] of said pressurized gas and said predetermined volume $V_{sub}$ [ml] entrained within it; selecting said predetermined distribution from a group consisting of: a homogeneous distribution, a heterogeneous distribution; selecting said heterogeneous distribution from a group consisting of: an arbitrary distribution, a distribution in which the density of said at least one substance within said mixture follows a predetermined pattern, and any combination thereof; selecting characteristics of said aerosol from a group consisting of: particle size, particle shape, particle distribution, and any combination thereof, are determinable from characteristics of said device selected from a group consisting of: said predetermined volume of said pressurized gas, said predetermined volume of said substance, said predetermined pressure of said pressurized gas, said predetermined orifice size, and any combination thereof;
ji. selecting said substance from a group consisting of: a gas, a liquid, a powder, a slurry, a gel, a suspension, and any combination thereof;
k. storing at least one said substance under either an inert atmosphere or under vacuum, thereby preventing reactions during storage; and
l. characterizing a dose-response curve for brain concentration of said substance to be of substantially linear form;
m. a dose-response curve for brain concentration having a fit selected from a group consisting of logarithmic, parabolic, exponential, sigmoid; power-low, and any combination thereof; of said substance when administered nasally via said device.

It is another object of the present invention to disclose the method, wherein said volume is a container.

It is another object of the present invention to disclose the method, additionally comprising steps of providing the container comprising a capsule having a main longitudinal axis, the capsule comprising a number n of compartments, configuring the capsule to contain the predetermined volume $V_{sub}$ [ml] of the at least one substance, containing the volume $V_{sub}$ [ml] of the substance in at least one of the n compartments; additionally comprising at least one of the following steps:

a. providing the capsule with n compartments; n is an integer greater than or equal to 1;
b. selecting the cross-sectional shape of at least one of the n compartments from a group consisting of: wedge shaped, circular, oval, elliptical, polygonal, annular, and any combination thereof;
c. for the number n of compartments being an integer greater than 1, providing at least two of the plurality of compartments having different volumes;
d. for the number n of compartments being an integer greater than 1, providing at least two compartments having the same volume;
e. for the number n of compartments being an integer greater than 1, providing at least two compartments having different cross-sectional areas;
f. for the number n of compartments being an integer greater than 1, providing at least two compartments having the same cross-sectional area;
g. for the number n of compartments being an integer greater than 1, providing at least two compartments containing different substances;
h. for the number n of compartments being an integer greater than 1, providing at least two compartments containing the same substance;
i. for the number n of compartments being an integer greater than 1, disposing the plurality of compartments coaxially around the main longitudinal axis of the capsule;
j. for the number n of compartments being an integer greater than 1, disposing the plurality of compartments sequentially along the main longitudinal axis of the capsule;
k. for the number n of compartments being an integer greater than 1, mixing the plurality of substances during dispensing; and
l. for the number n of compartments being an integer greater than 1, reacting the plurality of substances during dispensing.

It is another object of the present invention to disclose the method, additionally comprising step of inserting the predetermined volume $V_{sub}$ [ml] of the at least one substance into the container via a port fluidly connectable to the exterior of the device.

It is another object of the present invention to disclose the method, additionally comprising step of providing an airtight closure for the port, and of moving the port cover relative to the device in at least one motion selected from a group consisting of: sliding the port cover along the device, rotating the port cover around the device, rotating the port cover around a hinge on the exterior of the device and any combination thereof.

It is another object of the present invention to disclose a method of delivering a predetermined amount $M_{sub}$ [mg] of at least one substance within at least one body cavity of a subject, comprising:
a. providing a device comprising:
  i. at least one predefined volume sized and shaped for containing said predetermined amount $M_{sub}$ [mg] of said at least one substance;
  ii. a delivery end in fluid communication with said container; said delivery end comprising at least one orifice of diameter D [mm];
  iii. at least one valve mechanically connected to said container, characterized by at least two configurations: (i) an active configuration in which said valve enables delivery of said predetermined amount $M_{sub}$ [mg] of said at least one substance from said container to said body cavity via said delivery end; and, (ii) an inactive configuration, in which said valve prevents delivery of said predetermined amount $M_{sub}$ [mg] of said substance from said container to said body cavity; said valve is reconfigurable from said inactive configuration to said active configuration, and vice versa, within a predetermined period of time, dT, in response to activation of the same; and
  iv. a fluid tight chamber configured to contain predetermined volume $V_{gas}$ [ml] of pressurized gas at a predetermined pressure, $P_{gas}$ [barg];
b. emplacing said substance in said predefined volume;
c. setting said valve in said inactive configuration;
d. pressurizing said fluid-tight chamber with said gas to said predetermined pressure;
e. placing said delivery end in proximity to said body cavity;
f. reconfiguring said valve from said inactive configuration to said active configuration thereby entraining said substance in said predetermined volume $V_{gas}$ of said pressurized gas; thereby
g. delivering said predetermined amount $M_{sub}$ [mg] of said substance and said predetermined volume $V_{gas}$ of said pressurized gas through said orifice of diameter D [mm] in a pressure rate of $dP_{gas}/dT$;
wherein at least one of the following is held true:
(a) $P_{gas}$ is in the range of about 1-10 barg;
(b) $V_{gas}$ is in the range of about 1-21 ml;
(c) $M_{sub}$ is in the range of about 1-1000 mg;
(d) D is in the range of 0.2-6 mm;

$$\frac{dP}{dT} \to \infty;$$

(e) said pressure rate,
(f) said pressure rate is greater than about 0.001 barg/ms;
(g) said amount rate $dM_{sub}/dT$ is greater than about 0.0001 mg/ms;
(h) said volume rate $dV_{gas}/dT$ is greater than about 0.001 ml/ms;
(i) said predetermined period of time $dT \to 0$; and
(j) dT is in the range of about 0 to 500 millisecond.

It is another object of the present invention to disclose the method, additionally comprising at least one of the following steps:
a. generating a plurality of deliveries of said predetermined amount $M_{ub}$, and controllably altering said predetermined amount $M_{sub}$;
b. selecting said body orifice from a group consisting of a nasal cavity, the mouth, the throat, an ear, the vagina, the rectum, the urethra, and any combination thereof;
c. selecting viscosity η of said substance to be in a range of about $1 \times 10^{-3}$, poise to about 1 poise.
d. characterizing particles of said substance in a delivered aerosol, said aerosol a mixture of said at least one substance and said gas, by a DV50 diameter, said DV50 diameter being less than about 100 μm;
e. characterizing said particles by a DV90 diameter of less than about 1000 μm;
f. characterizing a plume of said aerosol by a plume angle θ, said plume angle θ subtending the full width of said plume, said plume angle θ subtending an angle of less than about 25°;
g. characterizing velocities of particles in said plume as being in a range of about 5 m/s to 50 m/s;
h. selecting said gas from a group consisting of: air, nitrogen, oxygen, carbon dioxide, helium, neon, xenon and any combination thereof;
i. dispensing said at least one substance, and during said step of dispensing, forming a plume of aerosol with predetermined distribution from a mixture of the predetermined volume $V_{gas}$ [ml] of said pressurized gas and said predetermined amount $M_{sub}$ [mg] entrained within it; selecting said predetermined distribution from a group consisting of: a homogeneous distribution; a heterogeneous distribution; selecting said heterogeneous distribution from a group consisting of: an arbitrary distribution, a distribution in which the density of said at least one substance within said mixture follows a predetermined pattern, and any combination thereof; selecting characteristics of said aerosol from a group consisting of: particle size, particle shape, particle distribution, and any combination thereof, are determinable from characteristics of said device selected from a group consisting of: said predetermined volume of said pressurized gas, said predetermined volume of said substance, said predetermined pressure of said pressurized gas, said predetermined orifice size, and any combination thereof;

j. selecting said substance from a group consisting of: a gas, a liquid, a powder, a slurry, a gel, a suspension, and any combination thereof;

kj. storing at least one said substance under either an inert atmosphere or under vacuum, thereby preventing reactions during storage;

ll. characterizing a dose-response curve for brain concentration of said substance to be of substantially linear form;

m. a dose-response curve for brain concentration having a fit selected from a group consisting of logarithmic, parabolic, exponential, sigmoid, power-low, and any combination thereof; of said substance when administered nasally via said device.

It is another object of the present invention to disclose the method, wherein said volume is a container.

It is another object of the present invention to disclose the method, additionally comprising step of providing said container having a main longitudinal axis, said container comprising at least one compartment, said compartment configured to contain said predetermined amount $M_{sub}$ [mg] of said at least one substance.

It is another object of the present invention to disclose the method, additionally comprising at least one of the following steps:

a. providing the container comprising a capsule;
b. providing said capsule with one compartment;
c. providing said capsule with n compartments; n is an integer greater than 1;
d. providing at least two of said plurality of said compartments having different volumes;
e. providing at least two said compartments having the same volume;
f. providing at least two said compartments having different cross-sectional areas;
g. providing at least two said compartments having the same cross-sectional area;
h. providing at least two of said compartments containing different substances;
i. providing at least two of said compartments containing the same substance;
j. disposing said plurality of compartments coaxially around said main longitudinal axis of said capsule;
k. disposing said plurality of compartments sequentially along said main longitudinal axis of said capsule;
l. mixing said plurality of substances during said dispensing; and
m. reacting said plurality of substances during said dispensing.

It is another object of the present invention to disclose the method as defined above, additionally comprising step of selecting the cross-sectional shape of said at least one compartment from a group consisting of: wedge shaped, circular, oval, elliptical, polygonal, annular, and any combination thereof.

It is another object of the present invention to disclose the method, additionally comprising step of inserting said predetermined amount $M_{sub}$ [mg] of said at least one substance into said container via a port fluidly connectable to the exterior of said device.

It is another object of the present invention to disclose the method, additionally comprising step of providing an air-tight closure for said port, and of moving said port cover relative to said device in at least one motion selected from a group consisting of: sliding said port cover along said device, rotating said port cover around said device, rotating said port cover around a hinge on the exterior of said device and any combination thereof.

It is another object of the present invention to disclose the method, additionally comprising step of selecting said substance from a group consisting of a gas, a liquid, a powder, an aerosol, a slurry, a gel, a suspension and any combination thereof.

It is another object of the present invention to disclose the method, additionally comprising step of storing at least one said substance under either an inert atmosphere or under vacuum, thereby preventing reactions during storage.

It is another object of the present invention to disclose the method, additionally comprising step of selecting said viscosity 11 such that, after steps of delivering said substance into a tube and measuring the distance L said substance travels down the tube, L is substantially independent of viscosity $\eta$ of said substance.

BRIEF DESCRIPTION OF THE DRAWINGS

The invention is herein described, by way of example only, with reference to the accompanying drawings, wherein:

FIGS. 1A-D show examples of the prior art;

FIG. 2 shows a cross-section of the face, illustrating zones in the nose from which material therein transfers to different parts of the body;

FIG. 3 illustrates an embodiment of a device of the present invention;

FIGS. 4A-E illustrate exemplary embodiments of multi-compartment capsules.

FIG. 5 illustrates a schematic of an exploded view of an exemplary embodiment of a mixing chamber in a capsule, the part of a capsule configured to mix components in a composition.

FIGS. 6A-G illustrate exemplary embodiments that allow holding the substances separate during storage and mixing the substances only upon activation and delivery.

FIGS. 7A-F illustrate embodiments of multi-compartment capsules, with exemplary embodiments of the separators configured to subdivide the capsules into compartments.

FIGS. 8A-D illustrate a preferred embodiment of the loading portion of the device with a pinch triggering mechanism.

FIGS. 9A-C illustrate an embodiment of the activation mechanism which is a dispensing device into which any flowable substance is introducible.

FIG. 10A-D illustrate an embodiment of the device of the present invention;

FIG. 11A-H illustrate the formation of an aerosol within the nozzle of the a device of the present invention;

FIG. 12 illustrates an exploded view of an embodiment of the device, which comprises a base cover (3), a drug container housing (4) to hold a drug container, a drug container holder stopper (5), a body (7) which comprises compressed gas chamber, a nose piece (9), an activation button (10) and a nose piece cover (12).

FIG. 13A-D illustrate this embodiment of the device, before activation.

FIG. 14A-D illustrate this embodiment of the device of FIG. 13A after activation.

FIG. 15A-D illustrate the embodiment of a device before activation with ball-type (2) drug container dividing and mixture elements. The nose piece is not shown.

FIG. 16A-D illustrate the embodiment of a device after activation with ball-type (2) drug container dividing and mixture elements. The nose piece is not shown.

Figure 22:
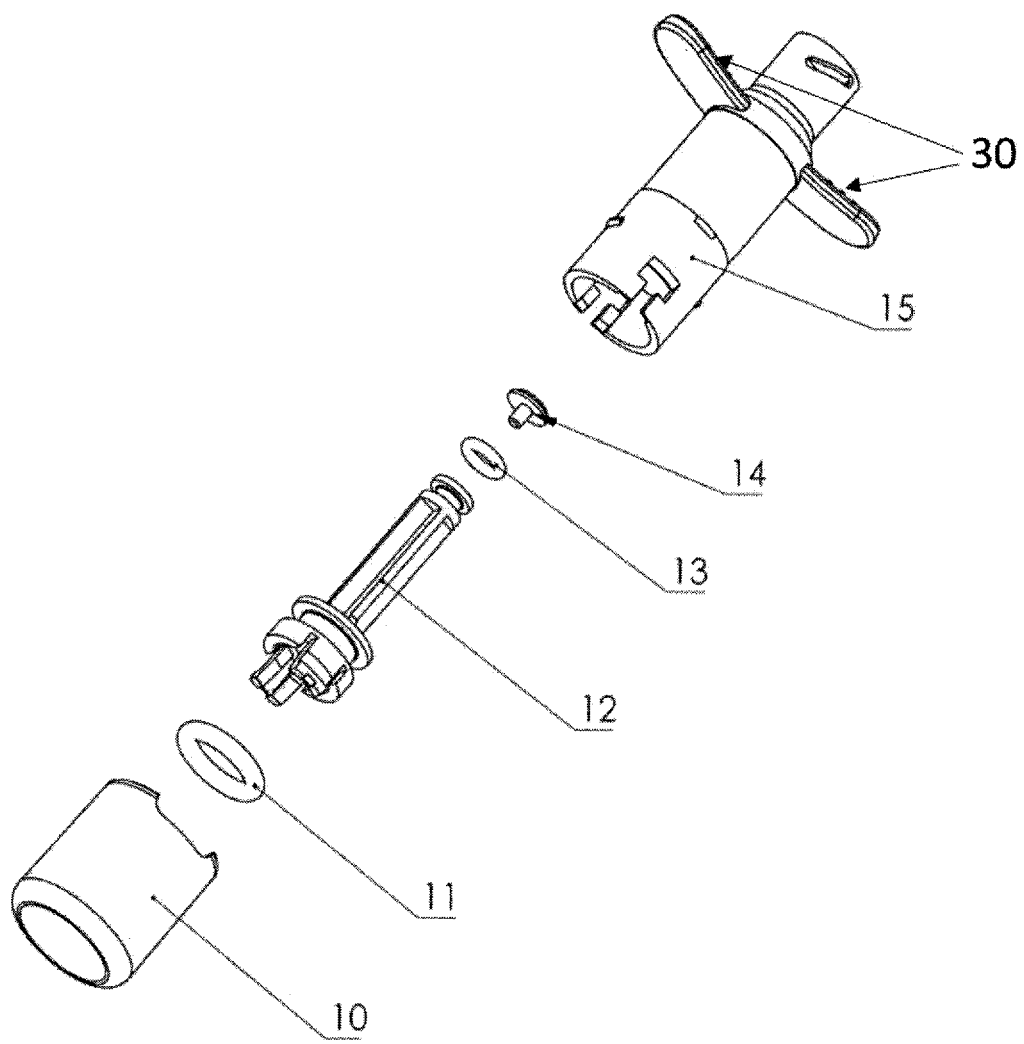
Figure 25A:
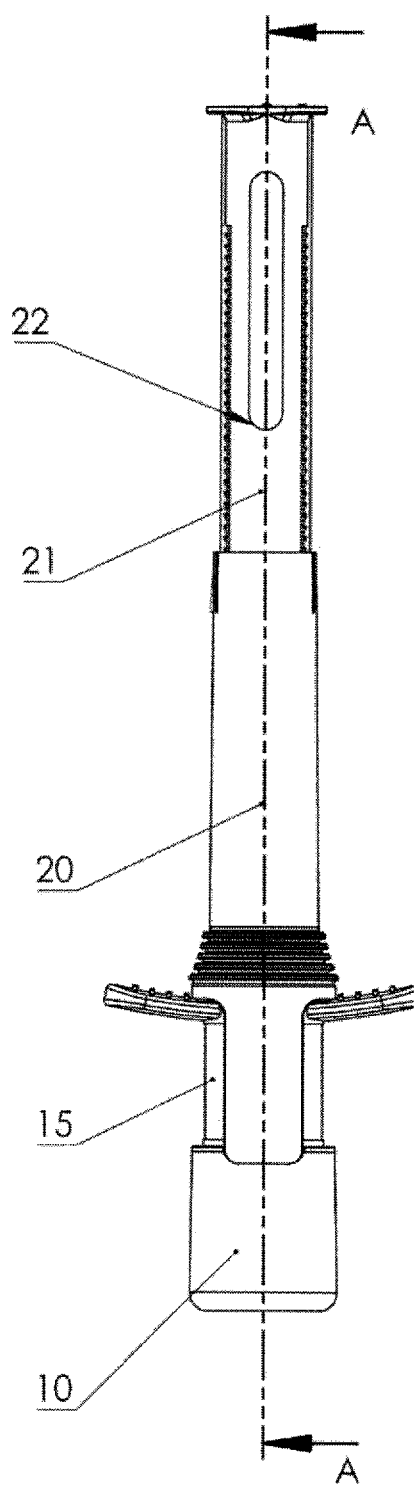
Figure 25B:
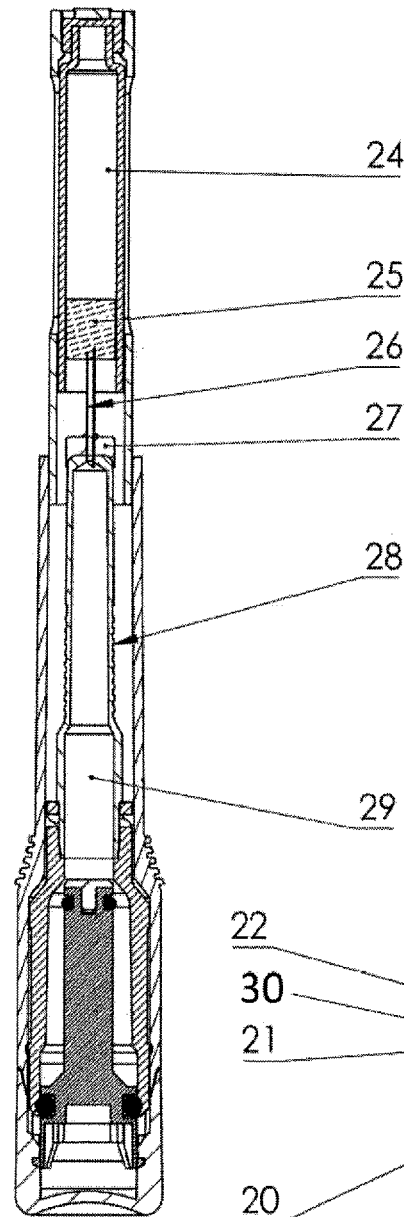
Figure 25C:
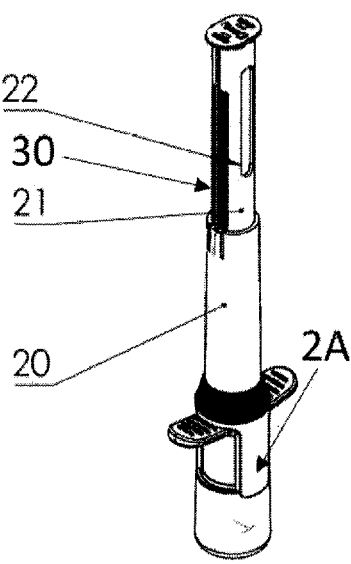
Figure 26A:
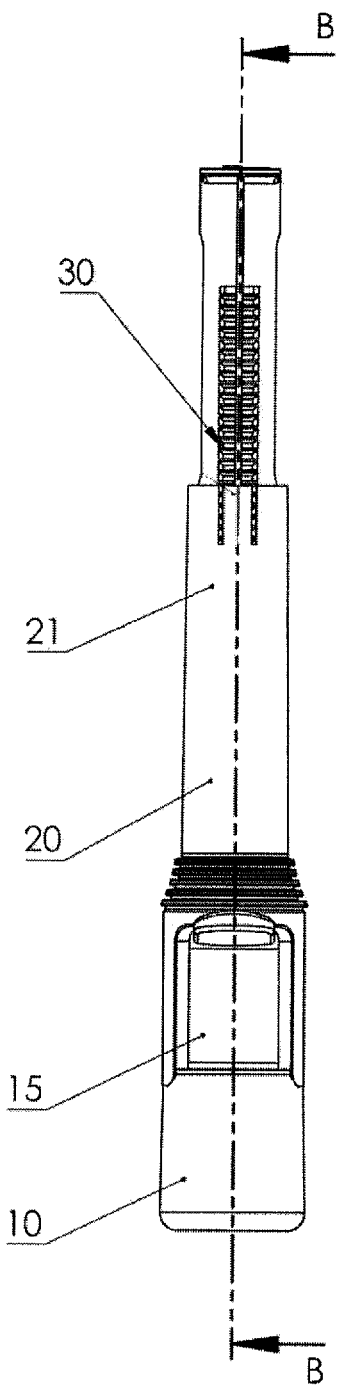
Figure 26B:
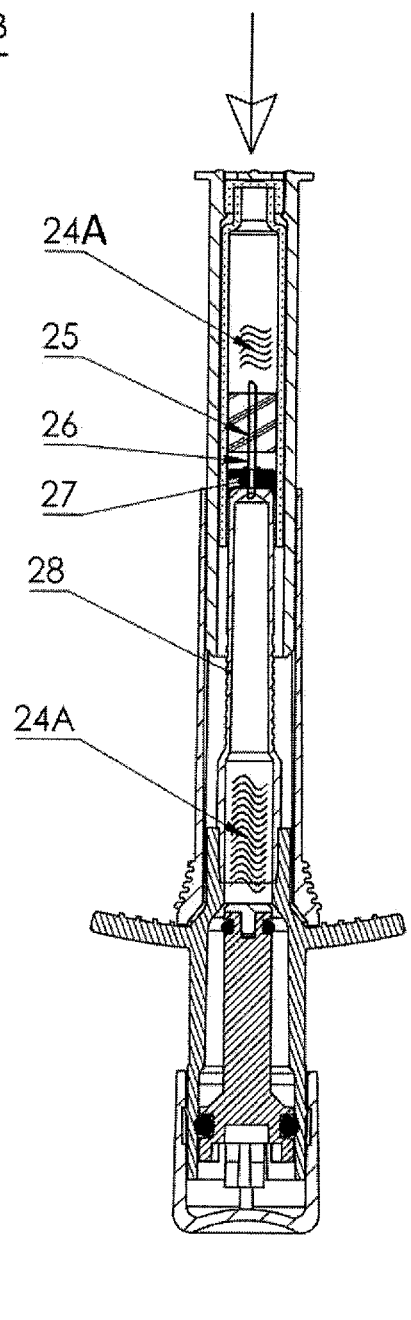
Figure 26C:
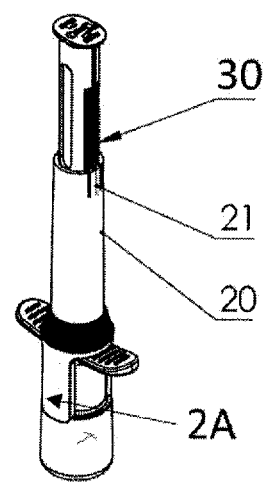
Figure 27:
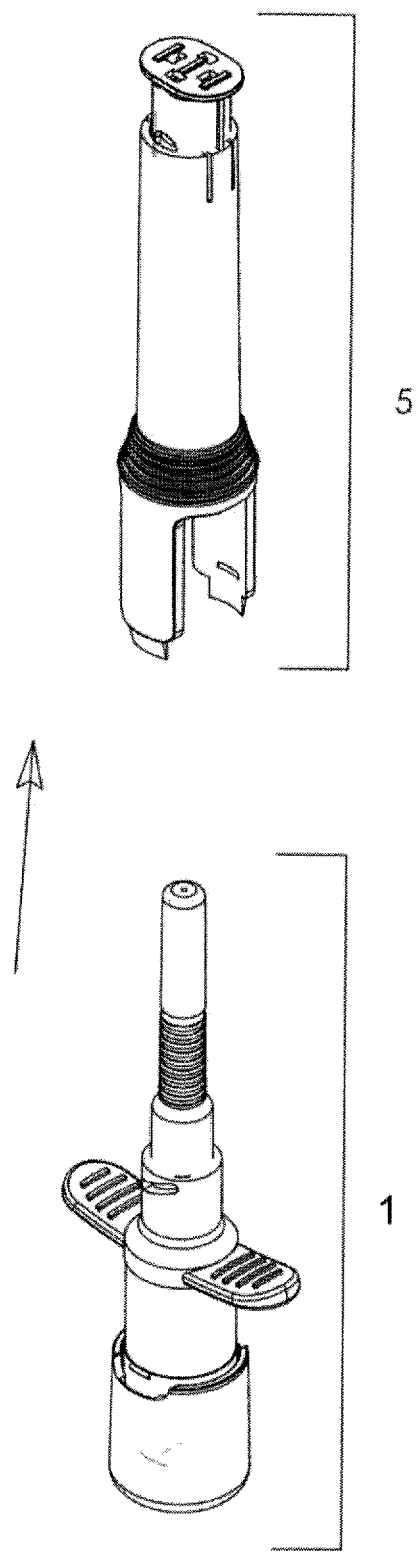

FIG. 19A-C illustrate an orifice, identifying the plume angle;

FIG. 20A-B illustrate plume angle for different devices;

FIG. 21A-C illustrate amount of material exiting a nasal cast for different devices;

FIG. 22 illustrates an experimental setup;

FIGS. 23A-D show the results of experiments using the setup;

FIGS. 24A-D show a typical particle size distribution;

FIGS. 25A-C show deposition of substance on a target;

FIGS. 26A-C show the embodiment of the device of FIG. 25 during loading of the drug into the integral drug volume from the primary drug container;

FIG. 27 illustrates removal of the nose piece or medicine chamber (5) from an aerosol delivery device (1) by pulling (arrow) the medicine chamber (5) away from the aerosol delivery device (1);

FIGS. 28A-D illustrate a device with a replaceable nose piece preloaded with a single dose of a medicament;

FIGS. 29A-D illustrate a device which can be loaded with a medicament, drug or substance via a syringe;

FIGS. 30A-D show the device of FIGS. 29A-D with a syringe in place;

FIG. 31 shows an embodiment of delivery device where adjustment of the size of the dose is made from the proximal end;

FIGS. 32A-C show embodiments of a device configured to supply a single dose of a medicament to each of two nostrils;

FIGS. 33A-E show a front view (FIG. 33A), a side view (FIG. 33B), a cross-section view (FIG. 33C) a top view (FIG. 33D), and a perspective view of an embodiment with nose pieces at approximately right angles to each other;

FIGS. 34A-E show a front view (FIG. 34A), a side view (FIG. 34B), a front view (FIG. 34C), a cross-section view of an embodiment with a single nose piece (FIG. 34D1), an enlarged top view (34D2), a top view (FIG. 34E) and a perspective view;

FIG. 35 shows an embodiment of the device, with the nozzle (6100) and the nozzle tip (6200) on the right, with the bracket indicating the region shown enlarged (6190) in FIG. 36.

FIG. 36 shows results of tests for three different operating conditions;

FIGS. 37A-B show droplet distribution and size for a larger needle when the Methylene blue solution is injected into the tube using a syringe;

FIGS. 37C-D show droplet distribution and size for a smaller needle when the Methylene blue solution is injected into the tube using a syringe;

FIGS. 38A1, 38A2 and 38B show droplet distribution and size for a larger needle when the device of the present invention is charged to 7 barg pressure and 20 ml Methylene blue solution is discharged through an orifice into the base of the tube.

FIGS. 38C-D show droplet distribution and size for a smaller needle when the device of the present invention is charged to 7 barg pressure and 20 ml Methylene blue solution is discharged through an orifice into the base of the tube;

FIGS. 39A-B show droplet distribution and size for a larger needle when the device of the present invention is charged to 4 barg pressure and 18 ml Methylene blue solution is discharged through an orifice into the base of the tube;

FIGS. 39C-D show droplet distribution and size for a smaller needle when the device of the present invention is charged to 4 barg pressure and 18 ml Methylene blue solution is discharged through an orifice into the base of the tube;

FIGS. 40A-C a comparison is made between 2 commercial, prior art devices and the present invention device;

FIGS. 41A-C a comparison is made between 2 commercial, prior art devices and the present invention device showing the stability of the droplets in the present invention;

FIGS. 42A-E nasal applicators were connected to a ~7 ml volume closed tubing, with a connection to a pressure sensor;

FIGS. 43A-C show Methylene Blue in aqueous solution delivered through a nostril of a human nasal cast model;

FIG. 44 show the total angle subtended by the plume as shown by the angle $\alpha$.

FIGS. 45A-C compares the plume angle $\theta$ with the 2 commercial nasal delivery devices (FIGS. 45A-B) and the SipNose device (FIG. 45C);

FIGS. 46A-B compares the amount of material reaching the upper layers of the nasal model for one of the prior-art devices (commercial 2—LMA MAD Nasal™) and the device of the present invention (SipNose);

FIG. 47 shows an experimental setup for determining coverage of a spray plume;

FIGS. 48A-D show coverage and droplet distribution for the SipNose device for different device parameters;

FIGS. 48E-J show coverage and droplet distribution for a number of different commercial devices;

FIG. 49 shows a plot of the number of particles vs. particle size, with the X axis (particle size) being logarithmic;

FIGS. 50A-C show that, for the three typical operating conditions, significant amounts of the material penetrate through the 4 mm of fabric.

FIGS. 50D-E show the inner area (dashed circle) delineating the area of heavier deposition and the outer area (solid circle) delineating the area of lighter deposition.

DETAILED DESCRIPTION OF THE PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a device capable of improving the transfer of medicament to a predetermined desired location and to provide a device capable of improving the delivery of medicament through the tissue.

In the present invention, a combination of parameters and forces such as pressure, gas/air volume orifice diameter enable the formation of optimized aerosol characteristics for both improved delivery of aerosol to the target area (such as the olfactory epithelium in the nasal cavity) and enhanced absorption at that area for better delivery to a desired tissue (such as the brain).

The term 'ul' or 'µm' hereinafter refers to the unit micro liters.

The term. 'capsule' or 'container' hereinafter refers to a container configured to contain a flowable substance. The term flowable refers hereinafter to any liquid, gas, aerosol, powder and any combination thereof. It should be emphasized that the term capsule can also refer to a predefined volume within the same in which a flowable substance is placed. In other words, the predefined volume is sized and shaped to enclose a predefined volume of said substance.

The term 'plurality' hereinafter refers to an integer greater than or equal to one.

The term 'olfactory epithelium' hereinafter refers to a specialized epithelial tissue inside the nasal cavity. The olfactory epithelium lies in the upper top portion of the nasal cavity.

The term 'substance' hereinafter refers to any substance capable of flowing. Such a substance can be a granular material, including a powder; a liquid; a gel; a slurry; a suspension; and any combination thereof.

The term 'gas' refers to any fluid that can be readily compressed. Gases as used herein include, but are not limited to, air, nitrogen, oxygen, carbon dioxide, helium, neon, xenon and any combination thereof. Devices charged by hand will typically use air as the carrier gas.

The term 'channel' hereinafter refers to a passageway allowing passage of a fluid through at least a portion of a mixing mechanism. The channel can be disposed within a portion of the mixing mechanism, forming a closed bore; it can be on an exterior of a portion of the mixing mechanism, forming a groove on the portion of the mixing mechanism, and any combination thereof.

The term 'about' refers hereinafter to a range of 25% below or above the referred value. The term 'biologic' or 'biologic response modifier' hereinafter refers to material manufactured in or extracted from biological sources such as a genetically engineered protein derived from human genes, or a biologically effective combination of such proteins.

All pressures herein are gauge pressures, relative to atmospheric pressure. Pressure units will be written herein using the standard abbreviation for "gauge", namely, "g". For example, atmospheric pressure is 0 barg and a pressure of 1 bar above atmospheric is 1 barg.

The term 'release time' refers hereinafter to the time for the drug and carrier gas to substantially completely exit the device. Typically, the release time is affected by the activation time and reflects the time for the device to reconfigure from the active configuration to the inactive configuration or vice versa.

The terms 'the device', 'the present device', 'the SipNose device' and 'SipNose' will be used interchangeably to refer to the device of the present invention.

In all of the embodiments of the device shown hereinbelow, identical numbers refer to identical functions.

All figures shown herein are illustrative and none is to scale.

The present invention teaches a device for delivering a predetermined amount of a substance, preferably comprising a medication or combination of medications, into a body orifice of a subject, the orifice comprising any of the body's natural orifices, including a nostril, the mouth, the ear, the throat, the urethra, the vagina, the rectum and any combination thereof.

In preferred embodiments of the device, the device comprises a delivery mechanism and a medicament capsule, as described hereinbelow. The device can apply a broad range of drugs and materials to the nasal cavity for local effect, deliver a broad range of drugs and materials through the nasal cavity to the systemic circulation, deliver a broad range of drugs and materials through the nasal cavity to the central nerve system (CNS) the brain, spinal cord and associated nerves, and any combination thereof.

The drugs to be applied could be, but are not limited to, pharmaceuticals, natural compounds, biologics, hormones, peptides, proteins, viruses, cells, stem cells and any combination thereof.

However, it should be emphasized that the device can be provided alone as well as in combination with a capsule.

In some cases the capsule would be provided with a known medicament within the same and in other cases the capsule would be 'filled' with the medicament just before use.

In some embodiments of the present invention, the device operating characteristics and the substance characteristics can be jointly optimized to maximize uptake of the substance at the desired site. In preferred variants of such embodiments, uptake is further optimized by exploiting synergies between delivery characteristics generated by the device and by the formulation or composition of the delivered material In some embodiments, the substance comprises one or more agents to optimize delivery through the mucosal membrane by means of mucoadhesive agent and/or a permeability enhancer agent and/or a particulate formulation in the nano-particle or macro-particle range, and any combination thereof. In such embodiments, the combination of the device and substance enhance the delivery of the active agent to the target area (nasal epithelium and more specifically olfactory epithelium) and from there to the target tissue (for example the brain).

A non-limiting example is a composition comprising a drug to be delivered and at least one chemical permeation enhancer (CPE). In a preferred embodiment, the composition contains two or more CPEs which, by using a nasal delivery device, affect in an additive manner or behave synergistically to increase the permeability of the epithelium, while providing an acceptably low level of cytotoxicity to the cells. The concentration of the one or more CPEs is selected to provide the greatest amount of overall potential (OP). Additionally, the CPEs are selected based on the treatment. CPEs that behave primarily by transcellular transport are preferred for delivering drugs into epithelial cells. CPEs that behave primarily by paracellular transport are preferred for delivering drugs through epithelial cells. Also provided herein are mucoadhesive agents that enable the extension of the exposure period of the target tissue/mucus membrane to the active agent, for the enhancement of delivery of the active agent to and through the mucus membrane.

In contrast to prior-art nasal delivery devices and technologies, the devices of the present invention can produce a fine aerosol in the nasal cavity or other desired body orifice at the target area and at the location of the target tissue instead of producing the aerosol only within the device or immediately after exit from the device. Utilizing the pressure as a driving force and the air as a carrier allows the material to be released from the nozzle as a mixture of aerosol and a pre-aerosolized state. The properties of the resultant aerosol are typically dependent on the properties of the device and of the medium into which the device is discharged. The properties of the device which affect the aerosol characteristics are the delivery pressure, the volume of the delivery gas, the characteristics of its orifice and time to activate.

In some embodiments, the aerosol properties are fairly independent of the delivered substance, while, in other embodiments, the pressure, volume, orifice characteristics, and delivered substance properties can be co-optimized.

In prior-art devices the aerosol is produced in proximity exit of the device. Typically, the aerosol comprises a wide "fan" of aerosol and a low driving force. Therefore, large droplets typically deposit very close to the exit from the device, while smaller droplets tend to quickly contact the walls of the passage, so that deposition is typically predominantly close to the delivery end of the device, with little of the substance reaching desired sites deeper in the body orifice, such as the middle and superior turbinates of the nose.

In contrast, in the present device, the pre-aerosolized mixture of gas and substance exits the device with a significant driving force as a mixture of aerosol and pre-aerolized material (fluid or powder). When the preaerosolized material hits the walls of the nasal passages, it "explodes" into a fine aerosol that is capable of being driven by the pressure deep into the nasal passages to deposit in the desired region.

FIGS. 1A-D illustrate capsules of prior art intended to deliver medicaments to the nasal passages. FIG. 1A illustrates the LMA MAD nasal atomizer from Wolfe Tory, FIG. 1B illustrates a typical nasal pump, FIG. 1C illustrates a Simply Saline nasal spray, and FIG. 1D illustrates the Optinose breath powered delivery device.

Typical prior art devices release aerosolized medicament. However, all have severe limitations.

The LMA MAD nasal atomizer (FIG. 1A) comprises a syringe, so the dose size can be quite accurate, if the user is careful. However, the delivery pressure is provided by the user depressing a plunger, so that control of delivery speed and delivery pressure (and the droplet size) depend on how hard the user depresses the plunger, making these parameters hard to control. Furthermore, syringe plungers are subject to stick-slip behavior, especially at the start of depression, making the delivery parameter harder to control accurately.

Devices such as nasal pumps (FIG. 1B) typically do not provide a fixed dose per activation, as the delivery energy is provided by pressure exerted by a user during activation. Typically, there is a wide dispersion in the size of the droplets produced following user activation, making it difficult to accurately target the medicament to a desired location.

The Simply Saline Nasal Mist (FIG. 1C) comprises a pressurized container. A button is pressed to release a portion of the contents. Each activation reduces the pressure inside the container, thereby reducing the velocity and pressure of delivery and altering the droplet size. The length of activation time depends on the time the button remains depressed, so that there is little control of the amount delivered.

The Optinose breath powered delivery device (FIG. 1D) is breath-powered. It uses a capsule containing a single dose of the medicament, so dose size is well-controlled. However, delivery speed and delivery pressure (and the particulates dispersion) depend on how hard the user exhales into the device and how long the user continues to exhale. Furthermore, exhalation pressures are typically higher at the start of exhalation than at the end, so the delivery parameters will vary during delivery.

Unlike the device of the present invention, none of the prior-art devices provide accurate control of all of the delivery parameters, which include dose volume, carrier volume, pressure, and delivery velocity.

A further advantage of the device of the present invention (the SipNose device) is that, unlike the prior art devices, it can be configured to accurately deliver large volumes (>100 ul) at high pressure, such that the high-velocity aerosol can be as reliably and reproducibly produced for large volumes as for small.

FIG. 2 illustrates locations for deposition of substances entering the nostrils. Typical locations are (a) deposition in the lungs after passage through the lower turbinates (240), thereby enabling transfer of the substance across the walls of the alveoli of the lungs; (b) deposition in the mucous membranes lining the nasal passages, especially the lower (240), and middle (230) turbinates, facilitating transfer of the substance to the blood; and (c) deposition in the olfactory epithelium mucous membranes of the upper turbinates (220) facilitating transfer, via the thin ethmoid bone (not shown) to the brain through the olfactory nerve endings (250) substance, typically as an aerosol, with the mixture of gas and substance entering the body orifice via the delivery end. Typically, discharge (delivery) time is less than about 500 ms.

The embodiments disclosed below disclose non-limiting examples of devices and methods for providing the predetermined volume of gas at the predetermined pressure.

FIG. 3 shows an exemplary embodiment of the device. In the embodiment of FIG. 3, a piston (8)' is used to compress the gas. The piston is moved by a lever (4) attached to the piston (8) by a rotatable connector (13). The piston (8) fits air-tightly and slidably in the air chamber (2). The lever (4) is rotatably attached to the handle (3) at its proximal end such that the distal end of the lever (4) can be pulled away from the handle (3) to retract the piston (8) toward the proximal end of the device and pull air into the air chamber (2) and the distal end of the lever (4) can be pushed toward from the handle (3) to extend the piston (8) toward the distal end of the device and compress the gas. In use, the mouthpiece (5) is placed in the mouth and the nosepiece (6) is placed in a nostril. Inhaling on the mouthpiece (5) activates the device (mechanism not shown), releasing the compressed gas from the air chamber (2), from whence it passes through the substance capsule (21) and exits the device through the distal end of the nosepiece (6).

The embodiments disclosed in FIG. 3 are typically configurable into four states: (a) a non-activated state where the valve is in its inactive configuration, the chamber contains non-pressurized gas, and the portion of the chamber in fluid connection with the valve is at a minimum, (b) a pre-activated state where the valve is in its inactive configuration, the chamber contains non-pressurized gas, and the portion of the chamber in fluid connection with the valve is at a maximum, in this stage the tip to be entered to the body orifice (the delivery end) can be under "vacuum" conditions or not, (c) a loaded configuration where the chamber contains a predetermined amount of pressurized gas and the valve is in its INACTIVE state, and (d) an activated state where the valve is in its ACTIVE state. Typically, the activated state discharges the device, with the mixture of gas and substance released from the device, entering the body orifice via the delivery end.

The characteristics of the aerosol, namely its size, shape and velocity, depend on the speed of exit of the gas from the chamber, the volume of air delivered, the characteristics of the delivery orifice and the activation time. The speed of exit of the gas from the chamber and the volume of air delivered depend on the pressure of the gas in the chamber in the loaded state, on the volume of the chamber in the loaded state, and on the characteristics of the fluid connection between the chamber and the delivery orifice. The less change there is in these characteristics during an activation and between activations, the more reliable and the more reproducible the device will be. Therefore, in controlling the characteristics of the fluid connection, the time taken to open the valve needs to be taken into consideration. In devices of the current invention, the valve opening times are both reproducible and short and are not in any way dependent on the user, so that the delivery comprises a short, reproducible, high velocity pulse of the gas.

The non-activated state and the loaded state appear identical; they differ in that, in the loaded state the chamber contains pressurized gas whereas, in the non-activated state, the chamber does not contain pressurized gas.

In some embodiments, including embodiments intended for use in emergencies or daily home use, the device is a single-use device with only two states, a loaded state and an activated state. The device is provided in the loaded state; activation of the trigger mechanism discharges the gas and substance.

In other embodiments, the device is provided in the pre-activated state. The user transforms the device into the loaded state, pressurizing the gas, and activates the trigger mechanism to discharge the gas and substance.

Capsules can be flexible or rigid. Rigid capsules can comprise materials such as glass, metal, rigid polymer and any combination thereof. Flexible capsules are preferably of a flexible polymer such as silicone. Preferably, capsules are sealable at both ends Multi-compartment capsules can contain different components of a substance in the different compartments; at least one compartment can contain a carrier gas, and any combination thereof.

In some embodiments, there is a single capsule for the carrier gas and the substance. Some embodiments have separate capsules for substance and gas.

Some embodiments have the carrier gas held in a gas holding chamber. The gas holding chamber can be filled at the time of manufacture or can be filled to the predetermined pressure by a charging mechanism.

Some embodiments have the substance held in a holding chamber. The holding chamber can be filled at the time of manufacture or can be filled by a filling mechanism such as, but not limited to, a syringe.

It should be emphasized that the present invention refers to both one compartment capsules as well as multi-compartment capsules.

FIG. 4A-E shows exemplary embodiments of multi-compartment capsules.

In multi-compartment capsules, walls divide the capsule into compartments. The compartments can have approximately the same volume or different volumes, and the same thickness or different thicknesses; if circular, they can have the same diameter or different diameters. They can have the same area at the end faces, or different areas.

The compartments, taken together, can form a large fraction of the volume of the capsule, or they can form a small fraction of the volume of the capsule.

Compartment walls can be equally spaced, either angularly or linearly, or they can be unequally spaced. Spacings can be arbitrary, they can be regular, they can follow a pattern, and any combination thereof.

Compartments can be near the edge of the capsule or at other positions within the capsule.

Before use, the compartments are preferably hermetically sealed to prevent mixing of the substances contained therein.

Compartment walls can be substantially similar in shape to the capsule walls (for non-limiting example, lenticular walls within a lenticular capsule) or at least one of the compartments' walls' shape differs from the shape of the cross-section of the capsule. (For non-limiting example, a lenticular wall within a circular capsule.)

Compartment walls can be non-frangible or frangible. Frangible walls permit mixing or reaction of the contents of adjacent compartments before the substances leave the compartments.

Compartments can, but need, not, have a frangible membrane at least one end.

Any compartments can contain one substance or a mixture of substances; any two compartments can contain the same substance or mixture thereof, or different substances or mixtures thereof.

The material of any combination of capsule walls and compartment walls can be rigid, semi-flexible, flexible and any combination thereof. Flexible or semi-flexible compartment or capsule walls can reduce dead space—regions of low gas flow—in the air path during activation.

Figure 4A:
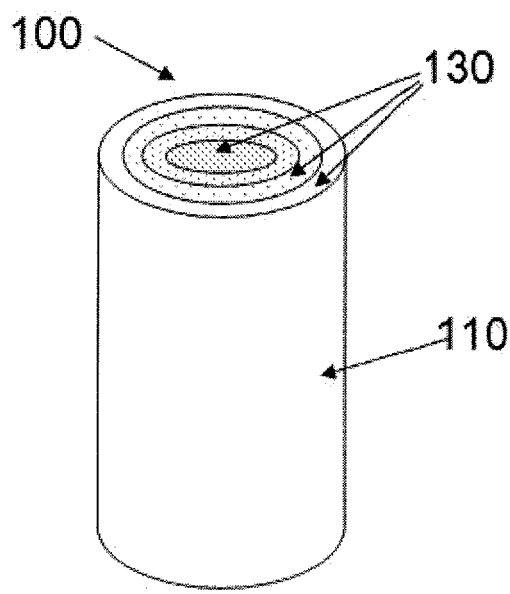

In the embodiment shown in FIG. 4A, the compartments (130) are coaxially disposed within the outer tegument (110), with the compartments nested within one another. The central compartment forms a cylinder and the remaining compartments, three in the exemplary embodiment of FIG. 4A, each forming an annulus of a cylinder. Nested compartments need not be coaxial.

Figure 4B:
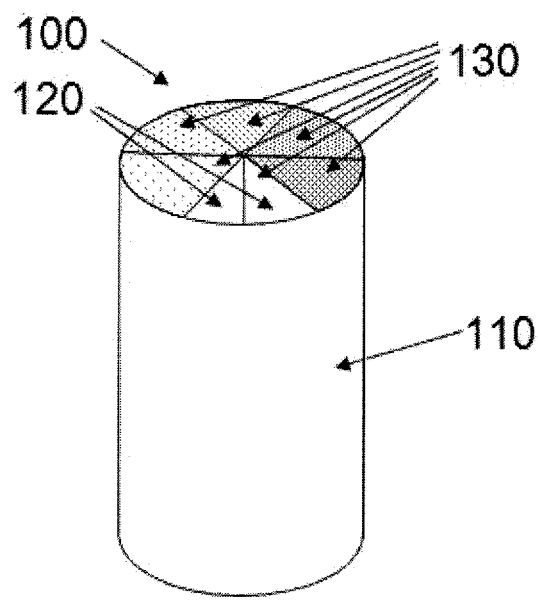

In the embodiment schematically illustrated in FIG. 4B, the capsule (100) comprises an outer tegument (110) enclosing n angularly disposed compartments (130) separated by walls (120), where n is less than about 10. In the embodiment shown in FIG. 4B, n is e.g., six.

Figure 4C:
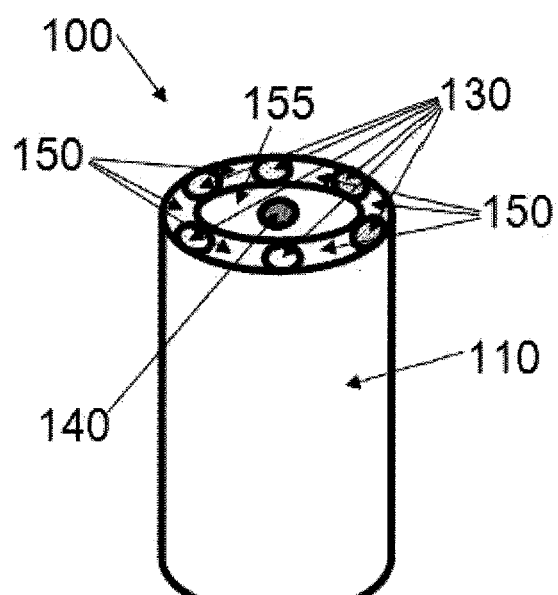

In the embodiment schematically illustrated in FIG. 4C, the capsule (100) comprises an outer tegument (110) enclosing six angularly disposed cylindrical compartments near the edge of the capsule (130), a central compartment (140), and auxiliary compartments (150, 155), for a total of 14 compartments.

In practice, the embodiment illustrated in FIG. 4C will have no more than about 20 compartments.

In some embodiments, there is no central compartment (140).

In the exemplary embodiment shown, the auxiliary compartments are hollow, containing a substance. In other embodiments, at least one of the auxiliary compartments (150, 155) is comprised of solid material, thereby forming part of the structure of the capsule.

In preferred embodiments, the central compartment (140) and the central auxiliary compartment (155) are solid, forming a solid central core for the structure. The remaining compartments (130, 150) comprise substance, where, in preferred embodiments, the compartments (130) contain a substance such as a medicament and the auxiliary compartments (150) contain a propellant, preferably compressed gas.

Figure 4D:
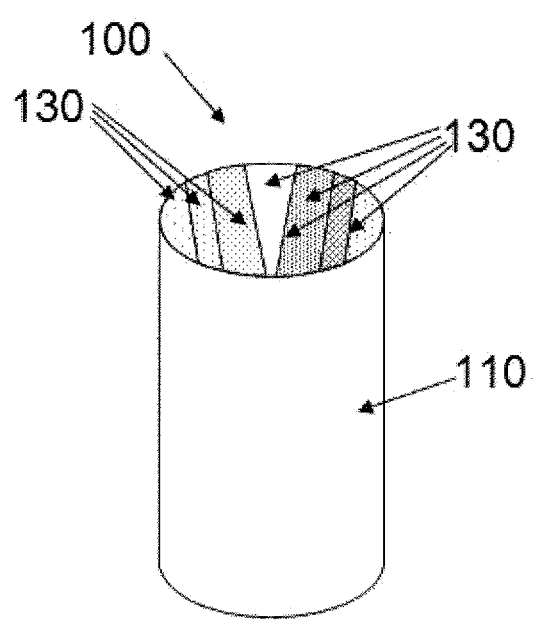

In the exemplary embodiment shown in FIG. 4D, the compartments (130) form slices within the outer tegument (110). In the exemplary embodiment of FIG. 4D, some of the slices have parallel sides, while the central slice is wedge-shaped; in other embodiments, all of slices have substantially parallel sides. In yet other embodiments, a plurality of slices are wedge-shaped. Slice-type capsules can have up to about 10 compartments.

Figure 4E:
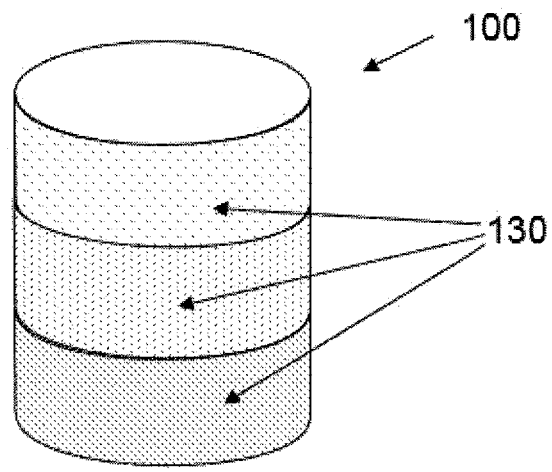

In the exemplary embodiment shown in FIG. 4E, the compartments (130) are arranged longitudinally, with the walls between the segments being frangible. Any number of such compartments can be used and the lengths of the compartments can differ.

These embodiments are merely exemplary; any combination of the above arrangements can be used.

In the exemplary embodiments shown, the walls separating the compartments are planar. In other embodiments, the walls can form a curve, either regular or irregularly shaped.

The main longitudinal axis of at least one of the compartments can be parallel to the main longitudinal axis of the capsule, it can be spirally disposed it can be at an angle to the main longitudinal axis of the capsule, and any combination thereof.

The main longitudinal axes of the compartments can be straight, they can form regular curve, they can form irregular curves, and any combination thereof. For any pair of compartments, the main longitudinal axes can be the same or they can be different.

In most embodiments, at least part of the upstream closure surface (not shown) and the downstream closure surface (not shown) of the capsule are frangible or otherwise removable, such that, when broken or otherwise removed, the medications can be delivered to the desired deposition site. In a variant of these embodiments, different portions at least one closure surface have different breaking strengths, such that the different portions can be broken at different times during delivery of the medication, enabling either differential mixing of medical formulations in different compartments or differential delivery of the medications in at least two of the compartments.

In some embodiments, at least part of the side surface of the capsule is frangible, enabling yet another mixing path or delivery path.

Capsules can be cylindrical with circular cross-section, as shown, cylindrical with oval, elliptical, lenticular, or polygonal cross-section, with the polygon having at least three sides and not more than about 20 sides. The polygon can be a regular or irregular.

Capsules can be spherical, elliptical, ovoid, pillow-shaped, football-shaped, stellate and any combination thereof. Capsules can form regular or irregular shapes.

Compartments can have substantially constant cross-section through the device or the cross-section can vary in area, in shape, or in any combination thereof.

Figure 5:
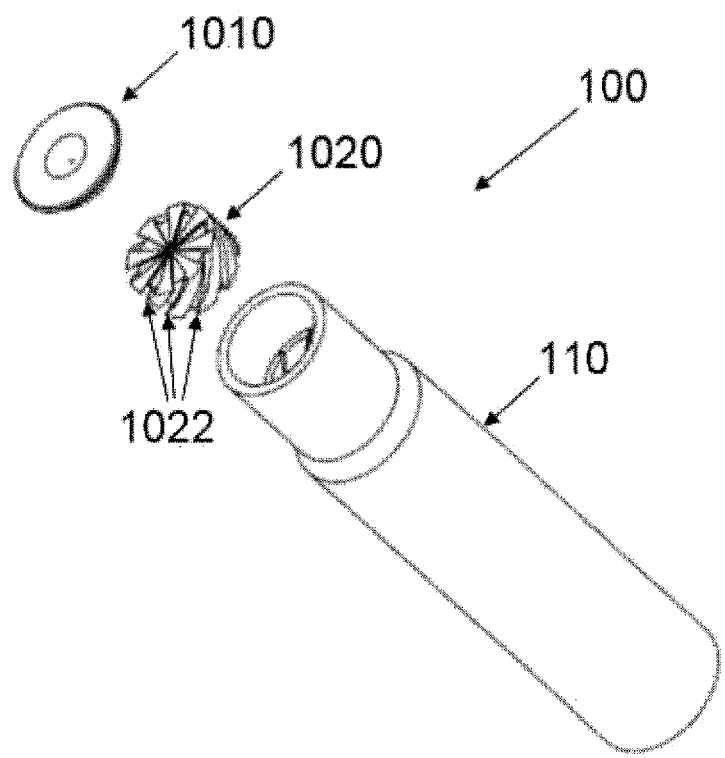

FIG. 5 shows a schematic of an exploded view of an exemplary embodiment of a mixing chamber in a capsule, the part of a capsule configured to mix components in a composition. In this exemplary embodiment, the tegument (110) of the capsule and the upstream closure surface (1010) of the capsule are shown. Also shown is a mixing mechanism (1020), in this case, a single-section mechanism. The substance compartments are not shown.

In this exemplary embodiment, the mixing mechanism (1020) comprises spirally-disposed air channels (1022) at the periphery of the mixing mechanism (1020). The central part of the mixing mechanism (1020) is solid, forcing the carrier gas and the substances to pass through the channels (1022). By narrowing the channel through which the gas passes and by changing the direction of the gas flow, mixing of the substances is enhanced. The mixing mechanism (1020) fits within the tegument (110) of the capsule (100) and mixing occurs within the capsule (100).

In some embodiments, a single channel is used. This can have a cross-section which is annular, circular, polygonal, lenticular, pie-shaped irregular, or any combination thereof. The channel main longitudinal axis can pass through any part of the capsule. Non-limiting examples include a circular cross-section with main longitudinal axis at the capsule center, and an annular cross-section at the periphery of the capsule, with main longitudinal axis at the capsule center.

In some embodiments, the capsule comprises two units, one comprising at least one substance and one comprising the mixing mechanism, such that the substances exit the compartments and are then mixed in the mixing mechanism.

In other embodiments, the mixing mechanism (1020) comprises channels disposed throughout its cross-section.

Channels can be arbitrarily arranged across a cross-section, regularly arranged across a cross-section, or irregularly arranged across a cross-section.

Channels can be linearly disposed, parallel to the main longitudinal axis of the capsule; or linear and disposed at an angle to the main longitudinal axis of the capsule.

The main longitudinal axis of at least one channel can be curved with respect to the main longitudinal axis of the mixing mechanism, with respect to an axis perpendicular to the main longitudinal axes, or any combination thereof.

Any combination of the above channel shapes can be used.

The shape of a channel cross-section can be substantially the same along the length of the channel, the shape can change along the length of the channel, the size of the cross-section can change along the length of the channel, and any combination thereof.

Shapes of the cross-sections of the channels can vary in the same manner along the length of the channel, or they can vary in different manners.

Shapes of the cross-sections of the channels can be the same for all the channels, or the shapes of the cross-sections of at least two channels can be different.

Sizes of the cross-sections of the channels can vary in the same manner along the length of the channel, or they can vary in different manners.

Sizes of the cross-sections of the channels can be the same for all the channels, or the sizes of the cross-sections of at least two channels can be different.

In some embodiments, the mixing mechanism (1020) comprises a plurality of longitudinal sections, with the sections having fluidly connected channels, but the channels are differently disposed longitudinally. For non-limiting example, a two-section device can have spirally disposed channels with left-handed spirals in the first section and right-handed spirals in the second section.

In some embodiments, there are different numbers of channels in the two sections. In other embodiments, there are the same number of channels in the two sections.

In other multi-section mixing mechanisms (1020), sections comprising channels are fluidly connected by substantially channel-free regions.

Mixing mechanisms can comprise between 1 and 10 regions. Individual regions can have any of the channel dispositions described hereinabove.

In some embodiments, mixing can be done by an integral mixing mechanism, either a single-section or a multi-section device. In other embodiments, mixing can be done by disposing a plurality of single-section mechanisms end-to-end, either abutting each other or with spacers to provide channel-free regions.

During the process of mixing, the first and second flowable substances can be mechanically mixed with each other and with the air or other gas, they can be reacted with each other, and any combination thereof.

In some embodiments, reaction of at least one flowable substance can be enhanced by a catalyst deposited on or part of the walls of the mixing region.

Criteria of the capsule, whether single-compartment or multi-compartment, can be optimized to include: ensuring that a single dose of the substance is delivered in its entirety, ensuring that the single dose contains the predetermined amount of the substance, ensuring that the dose is delivered to the desired region of the nose, and ensuring that delivery of the dose causes the minimum possible discomfort to the patient. Any combination of these criteria can be optimized for each particular combination giving rise to a different embodiment of the capsule.

The capsule can also be optimized for ease of insertion into a delivery device, for ease of removal from a delivery device, for stability of the contents during storage, for resistance of the capsule materials to environmental degradation, for resistance to undesired fracture, for reliability of use, for completeness of mixing, for completeness of reaction, and any combination thereof.

In some embodiments, the capsule comprises a filter configured to remove from the air at least one selected from a group consisting of particles, particulates, bacteria, viruses, moisture, and undesired gases before the air contacts the user. Such a filter, by preventing unpleasant odors or tastes from reaching the user and by preventing particles or particulates from reaching the user, can make the experience of using the device much more pleasant for the user and much safer. By removing bacteria and viruses, infection of the user can be prevented.

In some embodiments, the capsule contains only a single dose of the substance, the capsule being replaced after each use. In other embodiments, the capsule contains multiple doses of the substance, preferably packed separately, so that the dose is fresh for each use.

During dispensing of the substance, the gas passing through the capsule entrains the substances contained within the compartments such that the substances have a predetermined distribution within the dispensed mixture, where the predetermined distribution can be a homogeneous distribution or a heterogeneous distribution. Heterogeneous distributions can be: an arbitrary distribution, a distribution in which the dispersion of the at least one substance within the mixture follows a predetermined pattern, and any combination thereof.

According to another embodiment of the present invention, movement of air into the chamber during transformation of the device into said pre-activated state creates a vacuum in the region near or in the capsule.

As disclosed above, the capsule (10) can be designed in various forms to allow various options for drug component mixing; drug component maintenance at low humidity; temperature variation (heating or cooling), viscosity and variation, and combinations of these options.

FIGS. 6A-G and 7-F show embodiments of multi-compartment capsules, with exemplary embodiments of the separators configured to subdivide the capsules into compartments.

Figure 6A:
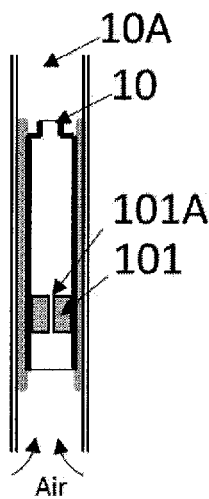

FIG. 6A shows a plunger-type barrier (101) between compartments. In this exemplary embodiment, there is one plunger (101). In other embodiments, more or fewer plungers (101) can be present. The plunger (101) comprises a hole or slot small enough to prevent passage of substance therethrough, but wide enough to allow passage of compressed air therethrough. When the device is activated, compressed gas (curved arrows at bottom) enters the capsule (10). The pressure forces the plunger (101) upward, forcing substance above the plunger (101) out of the top of the capsule. Substance below the plunger (101) will be forced upward by the compressed air, to mix with the substance above the plunger in a nose piece (not shown). The plunger (101) passes through the top of the capsule into an intermediate space (10A) below the nosepiece (not shown; a shoulder or other barrier (not shown) prevents the plunger (101) from exiting the nosepiece.

The hole or slot (101A) in the plunger (101) is narrow enough to prevent substance leakage during storage, and wide enough to allow compressed gas passage during activation, wiping the substance from the container during activation. The hole or slot (101A) in the plunger (101) can be designed in many ways to allow delivery that is very efficient, having a residual volume of less than 15% of the original volume. The plunger (101) can be made either from a flexible materials such as, but not limited to, silicone, rubber, flexible plastic or from a hard material such as, but not limited to, a polymer such as Delrin®, a plastic, nylon, metal and any combination thereof.

Figure 6B:
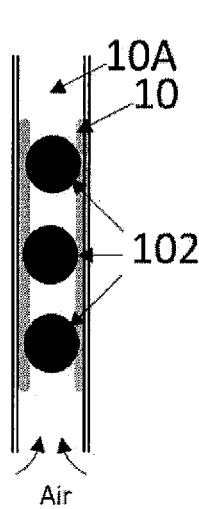

FIG. 6B shows ball-type barriers (102) between compartments. The balls (102) provide both a separation function, before activation, and a mixing function during activation. In this exemplary embodiment, there are 3 balls (103). In other embodiments, more or fewer balls (103) can be present. When the device is activated, compressed gas (curved arrows at bottom) enters the capsule (10). The pressure forces the balls (102) upward, forcing substance above the topmost ball (102) out of the top of the capsule. The topmost ball (102) passes through the top of the capsule into an intermediate space (10A) below the nosepiece (not shown; a shoulder or other barrier (not shown) prevents the balls (102) from exiting the nosepiece. The substance between the first and second balls can then pass through the top of the capsule (10) into the nosepiece (not shown, and mix with the first substance. The second ball (102) can then enter the intermediate space (10A), and similarly with all balls (102) in the capsule (10) until the capsule (10) is empty.

Ball-type barriers (102) are useful when mixing of several components should occur only upon delivery, when one or more substance should be maintained at low humidity, when the viscosity of the substance varies significantly, and any combination thereof. In addition, contact between the ball (102) and the walls of the capsule (10) can also ensure effective release of the substance from the capsule (10). Examples of substances which tend to cling to walls include, but are not limited to, oils and some powders. The barriers can be balls, as in the embodiment shown, angular dividers or any other shape which can be easily moved by the released compressed gas (low-friction contacts), and still provide effective sealing between the elements to avoid mixing during, for example, shipment and storage.

Figure 6C:
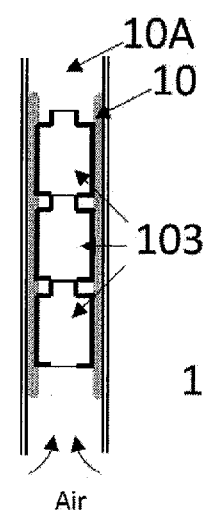

FIG. 6C shows an embodiment with linked drug containers (103) within the capsule (10). In this exemplary embodiment, there are 3 linked drug containers (103). In other embodiments, more or fewer linked drug containers (103) can be present. The linked drug containers (103) are sealed by frangible membranes. A single frangible membrane can seal the top of one drug container (103) and the bottom of the adjacent drug container (103), separate frangible membranes can be used for adjacent ends of drug containers, and any combination thereof. When the device is activated, compressed gas (curved arrows at bottom) enters the capsule (10). The pressure bursts the membranes, allowing mixing and exit into the nosepiece of the substance s within the linked drug containers (103).

In a preferred embodiment, each drug containers (103) is made of a soft thin sheet. The sheet can be a polymeric membrane, a continuous sheet or any other form which is thin enough to be easily torn when desired by the released of the compressed air. All drug containers (103) are connected to each other during manufacturing. Mixing occurs only during activation, with the compressed gas tearing the membranes/sheets dividing the compartments. Once the membranes are torn, the substance s are exposed to the compressed gas, mixed and delivered.

Figure 6D:
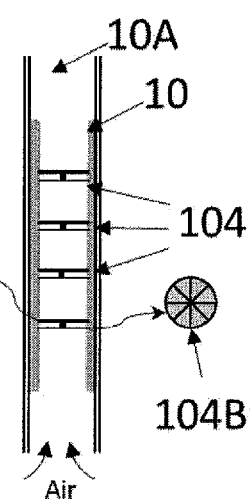

FIG. 6D shows an embodiment with sets of two-layer membranes (104A, 104B) within the capsule (10). In this exemplary embodiment, there are 4 sets of two-layer membranes (104A, 104B). In other embodiments, more or fewer sets of two-layer membranes (104A, 104B) can be present. The lower membrane (104B) is reticulated, with portions separable from each other, and the upper membrane (104A), frangible. When the device is activated, compressed gas (curved arrows at bottom) enters the capsule (10). The pressure causes the separable portions of the lower membrane (104B) to rotate upward, tearing the upper membrane (104A) and allowing mixing and exit into the nosepiece of the substance s within the capsule (10).

This embodiment differs from the previous one in that: (a) the drug containers do not form one unit; (b) the separate zones are separated from each other by membrane which is composed of two layers: one provides the rigidity of the membrane and is made of a rigid material, and the other one is a continuous flexible sheet which seals against the lower rigid part during until activation and which opens when air is pressed against its lower side The membranes (104A, 104B) open only one way, when air presses against their lower side during activation, allowing mixing of the substances during delivery.

Figure 6E:
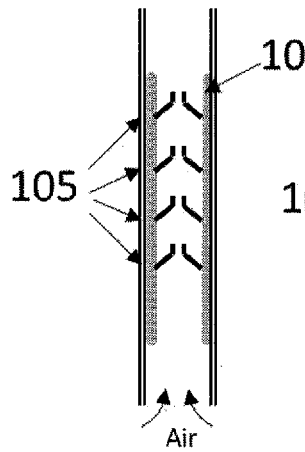

FIG. 6E shows an embodiment with duckbill valves (105) within the capsule (10). In this exemplary embodiment, there are 4 duckbill valves (105). In other embodiments, more or fewer duckbill valves (105) can be present. When the device is activated, compressed gas (curved arrows at bottom) enters the capsule (10). The pressure causes the duckbill valves (105) to rotate upward, allowing exit and mixing of the substance s within the capsule (10).

Figure 6F:
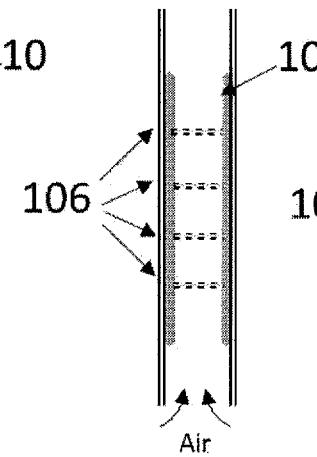

FIG. 6F shows an embodiment with frangible membranes (106) within the capsule (10). In this exemplary embodiment, there are 4 frangible membranes (106). In other embodiments, more or fewer frangible membranes (106) can be present. When the device is activated, compressed gas (curved arrows at bottom) enters the capsule (10). The pressure causes the frangible membranes (106) to tear, allowing mixing and exit into the nosepiece (not shown) of the substance s within the capsule (10).

Figure 6G:
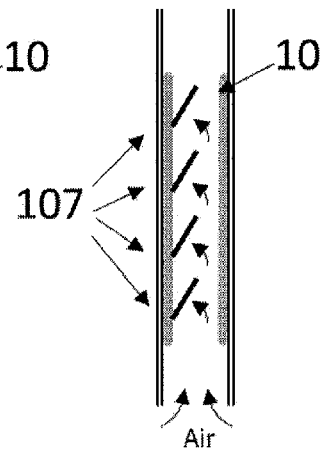

FIG. 6G shows an embodiment with bendable membranes (107) within the capsule (10). In this exemplary embodiment, there are 4 bendable membranes (107). In other embodiments, more or fewer bendable membranes (107) can be present. When the device is activated, compressed gas (curved arrows at bottom) enters the capsule (10). The pressure causes the bendable membranes (107) to rotate upward (curved arrows in middle) about connection points between the bendable membranes (107) and the capsule (10) wall, allowing mixing and exit into the nosepiece (not shown) of the substances within the capsule (10).

These exemplary embodiments allow holding the substances separate during storage and mixing the substances only upon activation and delivery. In some embodiments, the device or the substances therein can be configured to generate a temperature change, either heating or cooling, during mixing and delivery. The device can further be configured so that components for creating a temperature change in the device are not released with the delivered substances.

Heating and cooling can be triggered by mechanical force, by pressure, by chemical reaction and any combination thereof. This can be done inside the drug capsule, around the drug capsule, or outside the device itself in its packaging, to be triggered right before activation of the device.

Such temperature change can be generated during activation (short time temperature change) or prior to activation (long time temperature change). Long time temperature changes require a temperature activation separated from the delivery activation.

Either option, or at least the long time temperature change, further requires proper device sealing to allow temperature to be maintained inside the device and to allow equilibration prior delivery. Such options can further include a temperature indicator, such as by a color change in a dedicated control window, to allow the user to know that the device is ready for activation.

A temperature change can be an increase in temperature, a decrease of temperature, or both.

A temperature change can be useful for example for:
Substance mixing
Dissolution of one substance in another
Absorption of a substance or mixture of substances in tissue, for example, a delivery temperature regulated with respect to the temperature of the nasal passages.
Effective scattering of a substance or mixture of substances on tissue, for example, to create a flat, thin, uniform layer in the nasal passages and hence improve absorption
Affect the viscosity of a substance or mixture of substances (both increase and decrease of viscosity can occur).
Affect nature of a substance or mixture of substances. For example: polymerization can be initiated only during delivery, or during or after contact with tissue.

One embodiment comprises two heating agents. These heating agents are in compartments of a capsule. Upon activation of the device, or upon activation of heating (for example, buy pressing a button), a membrane separating the two compartments is torn, allowing the heating agents to mix and to generate heat within the device. Other membranes are not torn by this activity, which keeps the heating agents in a sealed compartment—sealed so as to prevent delivery of heating agent delivery but allow gas passage to other compartments. Passage of the compressed gas then delivers the heated substances or other desired substances. Mixing, as disclosed above, can occur during delivery.

FIG. 7A shows an embodiment with sets of two-layer membranes (104A, 104B) and a mixing ball (102) within the capsule (10). In this exemplary embodiment, there are 2 sets of two-layer membranes (104A, 104B) and a single mixing ball (102) at the top of the capsule (10). In other embodiments, more or fewer sets of two-layer membranes (104A, 104B) and more or fewer mixing balls (102) can be present; the mixing balls (102) can be at any desired location within the capsule (10). The lower membrane (104B) is reticulated, with portions separable from each other, and the upper membrane (104A), frangible. When the device is activated, compressed gas (curved arrows at bottom) enters the capsule (10). The pressure causes the separable portions of the lower membrane (104B) to rotate upward, tearing the upper membrane (104A) and allowing mixing and exit into the nosepiece of the substances within the capsule (10). Further mixing is provided by the mixing ball (102). As disclosed above, a shoulder or other stopper in the nosepiece (not shown) prevents the mixing ball (102) from exiting the nosepiece (not shown).

FIG. 7B shows an embodiment with duckbill valves (105) and a mixing ball (102) within the capsule (10). In this exemplary embodiment, there are 2 duckbill valves (105) and a single mixing ball (102) at the top of the capsule (10). In other embodiments, more or fewer duckbill valves (105) can be present and more or fewer mixing balls (102) can be present; the mixing balls (102) can be at any desired location within the capsule (10). When the device is activated, compressed gas (curved arrows at bottom) enters the capsule (10). The pressure causes the duckbill valves (105) to rotate upward, allowing exit and mixing of the substances within the capsule (10). Further mixing is provided by the mixing ball (102). As disclosed above, a shoulder or other stopper in the nosepiece (not shown) prevents the mixing ball (102) from exiting the nosepiece (not shown).

FIG. 7C shows an embodiment with frangible membranes (106) and a mixing ball (102) within the capsule (10). In this exemplary embodiment, there are at least two frangible membranes (106) and a single mixing ball (102) at one end of the capsule (10). In other embodiments, more or fewer frangible membranes (106) can be present and more or fewer mixing balls (102) can be present; the mixing balls (102) can be at any desired location within the capsule (10). When the device is activated, compressed gas (curved arrows at bottom) enters the capsule (10). The pressure causes the frangible membranes (106) to tear, allowing mixing and exit into the nosepiece (not shown) of the substances within the capsule (10). Further mixing is provided by the mixing ball (102). As disclosed above, a shoulder or other stopper in the nosepiece (not shown) prevents the mixing ball (102) from exiting the nosepiece (not shown).

FIG. 7D shows an embodiment with bendable membranes (107) and a mixing ball (102) within the capsule (10). In this exemplary embodiment, there are at least two bendable membranes (107) and a single mixing ball (102) at one end of the capsule (10). In other embodiments, more or fewer bendable membranes (107) can be present and more or fewer mixing balls (102) can be present; the mixing balls (102) can be at any desired location within the capsule (10). When the device is activated, compressed gas (curved arrows at bottom) enters the capsule (10). The pressure causes the bendable membranes (107) to rotate upward (curved arrows in middle) about connection points between the bendable membranes (107) and the capsule (10) wall, allowing mixing and exit into the nosepiece (not shown) of the substances within the capsule (10). Further mixing is provided by the mixing ball (102). As disclosed above, a shoulder or other stopper in the nosepiece (not shown) prevents the mixing ball (102) from exiting the nosepiece (not shown).

FIG. 7E shows an embodiment with two half balls (102). In this exemplary embodiment, there is one pair of half-balls (102). In other embodiments, more pairs of half-balls (102) can be present. When the device is activated, compressed gas (curved arrows at bottom) enters the capsule (10). The pressure causes the half-balls (102) to move upward. They will separate and tumble as they move, allowing gas to pass between and around them thus mixing and delivering the substance. As disclosed above, a shoulder or other stopper in the nosepiece (not shown) prevents the mixing ball (102) from exiting the nosepiece (not shown).

FIG. 7F shows an embodiment with two attached mixing balls (102). In other embodiments, more mixing balls (102) can be present. When the device is activated, compressed gas (curved arrows at bottom) enters the capsule (10). The pressure causes the mixing balls (102) to move upward, thus causing efficient mixing of the substances. As disclosed above, a shoulder or other stopper in the nosepiece (not shown) prevents the mixing ball (102) from exiting the nosepiece (not shown).

The mixing balls need not be spherical; any shape that will provide good sealing during storage and low-friction movement during activation can be used.

FIGS. 8A-D and 9A-C show exemplary embodiments of the loading and triggering region of embodiments of devices with mechanical triggering mechanisms, all of which are configured to open fully, quickly and reproducibly, with the time over which the valve opens being reproducible, independent of how the user may operate the device. For example, in the suction devices described herein, a weak suction will induce the same full opening over the same time period as a strong suction, and, in the mechanical devices disclosed herein a slow activation of the triggering mechanism will induce the same full opening over the same time period as a rapid activation of the triggering mechanism.

In some embodiments, the loading region of the device comprises at least one filter to remove from the air (or other gas) at least one selected from a group consisting of particles, particulates, bacteria, viruses, moisture, and undesired gases before the air contacts the user.

Preferably, the air or gas is filtered on entrance to the air chamber from the outer environment (the room, the surrounding area). Alternatively or additionally, air can be filtered on exit from the air chamber, while within the loading air chamber, and any combination thereof.

FIG. 8A-D shows a preferred embodiment of the loading portion of the device (1000) with a pinch triggering mechanism. FIG. 8A shows a side view of the device, FIG. 8B shows a cross-section, taken along the line AA in FIG. 8A, FIG. 8C shows an exploded view, and FIG. 8D shows a perspective view.

The device comprises a hollow upstream portion (1881) fluid-tightly connected to a hollow downstream portion (1889). In this embodiment, the activation mechanism (1880) comprises a cup-shaped insert (1884) fitting snugly and fluid-tightly within the hollow interior of the device. The outer rim of the insert (1884) is preferably fixed to the outer wall of the activation mechanism (1880), with its inner rim (1885) able to slide on an inner wall (1886), preferably tubular, of the activation mechanism (1880). In the activation mechanism's (1880) closed position, a stop (1882) is firmly held by the inner rim (1885) of the insert.

The inner wall of the activation mechanism (1880) comprises a throughgoing bore (1883). In some variants of this embodiment, a flexible tube (1888) is fluid-tightly fixed to the wall (1886) such that there is flexible tubing in at least the portion of the wall abutting the stop (1882). In other variants of this embodiment, the flexible tube (1888) passes through the bore (1883).

In preferred variants of this embodiment of an activation mechanism, in the closed position, the stop (1882) fits into and sits in a hole in the inner wall (1886). In other variants, the stop (1882) fits into and sits in a depression in the inner wall (1886).

When the activation mechanism (1880) is in the closed position, the flexible tube (1888) is pinched between the stop (1882) and the inner side of the throughgoing bore (1883).

When the activation mechanism (1880) is activated, the insert (1884) slides up along the wall, releasing the stop (1882) so that the pinched region in the flexible tube (1888) is released, thereby releasing the pressurized gas and dispensing the substance.

In the embodiment shown in FIGS. 8A-D, the activation mechanism can be activated either by sucking on the suction mechanism (1810), creating a partial vacuum above the cup-shaped insert (1884) and pulling it upward, thereby releasing the stop (1882), or by pressing the pressable lever (1870). Pressing the pressable lever (1870) forces it inward so that the ramp portion (1782) of the pressable lever pushes the cup-shaped insert (1884) upward, thereby releasing the stop (1882), releasing the pressurized gas and dispensing the substance.

In some embodiments, flexible filling material such as, but not limited to, flexible tubing, can be placed within the region of the device (not shown) containing the substance to be delivered in order to reduce dead space within the device. Reducing dead space will not affect the characteristics of the aerosol formed after release, but it will decrease pressure loss and increase air speed within the device, thereby substantially reducing residual substance remaining within the device after completion of activation, either within the capsule or adhering to the interior walls of the device, e.g., within the nozzle. It is well known in the art that residual material within a delivery device can be released on subsequent uses of the device and that the amount of such residual material released during a given use of a device is extremely variable. Therefore, minimizing residual substance within the device will increase the accuracy and reproducibility of delivery, thereby increasing its repeatability and reliability, both by maximizing the fraction of the substance actually delivered from the current capsule and by minimizing the amount of residual substance on the walls of the device.

It should be noted that the capsules (disclosed hereinbelow) are designed so as to avoid residual volume within the capsule itself, since, even in the case of a single dose or disposable capsule there are safety issues involved in disposing of capsules containing residual amounts of hazardous drugs or other hazardous component in the composition.

Other trigger mechanisms include, but are not limited to, a releasable catch, a pressable button a detectable predetermined sound pattern, a detectable predetermined light pattern, a moveable lever, a slider moveable from a first position to a second position, a rotatable knob is rotated, a releasable latch configured and any combination thereof.

The predetermined sound pattern can be: a constant-pitch sound, a varying-pitch sound, a constant volume sound, a varying volume sound and any combination thereof.

The predetermined light pattern can be: a constant-color light, a varying-color light, a constant brightness light, a varying brightness light and any combination thereof.

In some embodiments, the device comprises a unidirectional valve such that gas can flow from the charging mechanism to the delivery end, but is unable to flow in the reverse direction.

In some embodiments, a substance to be dispensed (which can comprise any number of materials) can be stored within a capsule, either as the substance to be dispensed or as a precursor or precursors, with the capsule placeable within the device, as described hereinbelow. In such embodiments, the capsule is ruptured during activation, either all at once or in stages, thereby dispensing the substance.

In other embodiments, a substance, prepared in a conventional matter, is introducible into a holding chamber within the device and, on activation of the device, the substance is dispensed. Embodiments of this kind can be used as emergency dispensing devices, since any flowable substance can be introduced into the holding chamber and since the holding chamber, which has no facilities for separating precursors or for providing an inert atmosphere in the chamber, is not intended for long-term storage of substances.

In some embodiments, the capsule chamber in which the capsule can be placed can also function as a holding chamber, so that the substance can be dispensed either from the capsule or directly from the holding chamber.

In other embodiments, an insert can be placed within the capsule chamber, with the interior of the insert being a holding chamber.

An embodiment of the activation mechanism a dispensing device (1000) into which any flowable substance is introducible is shown in FIG. 9A-C. The charging mechanism is not shown. FIG. 9A shows a side view of the embodiment, FIG. 9B shows a top view of the embodiment, and FIG. 9C shows a cross-section, taken along the line AA in FIG. 9B.

In this embodiment, the means of loading the substance into the device is a syringe (2000). The syringe (2000) can be placed in the injection port (2100, FIG. 9C) and the syringe plunger depressed so that the flowable substance enters a dispensing chamber (2200) within the device (1000). Before, during or after injection of the substance into the chamber, the device can be charged, in any manner described herein, using any activation mechanism described herein or known in the art.

In some embodiments, the syringe is left in the injection port. In other embodiments, a cover (2300) is provided for the injection port, so that, after loading the substance into the chamber, the injection port can be sealed by means of the cover. As shown in the embodiment of FIG. 9, the cover (2300) can slide longitudinally onto and off the injection port (2100), In other embodiments, it can rotate or spiral around the device to cover or uncover the injection port (2100), it can rotate around a hinge on the body of the device so that it flips onto and off the injection port (2100), or any other method of sealing the port can be used. In the embodiment as shown, in the open position, the syringe goes through a hole in the cover in order to reach the chamber. Any combination of the above embodiments can be used in a cover.

In some embodiments, the substance is stored in a capsule or in a sealed compartment in the device. Before or during activation, the capsule or sealed compartment is breached and pressure on the capsule (e.g., by pressing a button to move the piston of a built-in syringe) forces the contents into a dispensing chamber (2200). Dispensing gas passing through the dispensing chamber (2200) then entrains the substance and delivers it.

In some embodiments of a device with separate storage chamber and holding chamber, the capsule comprises a syringe or a syringe like compartment, a rubber piston and seals. The longitudinal axis of the syringe and piston are at right angles to the longitudinal axis of the device. Pressure on the piston moves the substance from the syringe into the holding chamber, in a manner similar to the syringe (2000) and holding chamber (2200) in FIGS. 9A-C.

In the embodiment shown, a pinch triggering mechanism is used, as shown hereinabove in FIGS. 8A-D, although any of the other activation mechanisms described herein or any conventional valve known in the art can be used.

Figure 9A:
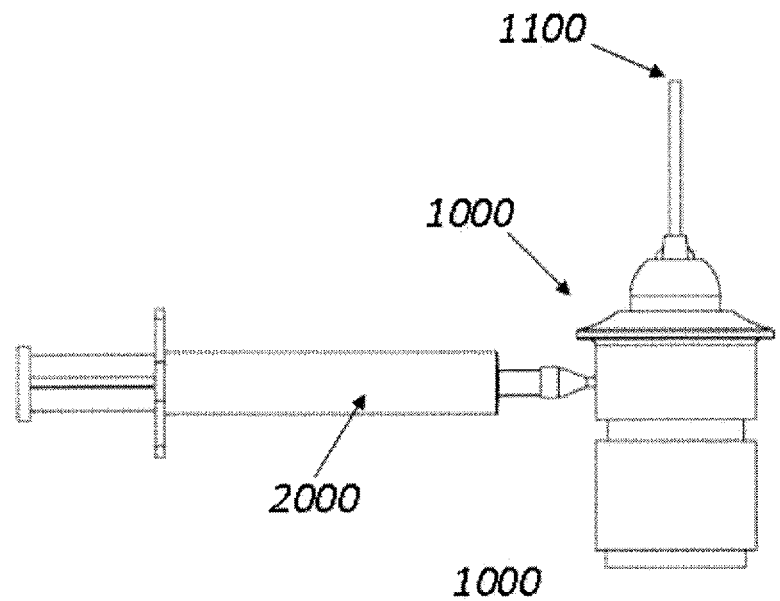
Figure 9B:
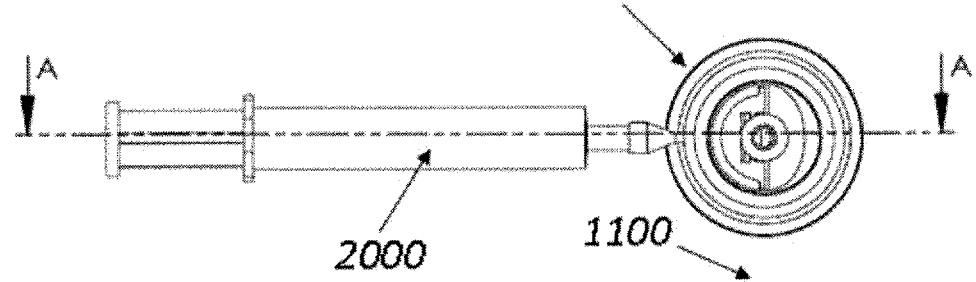
Figure 9C:
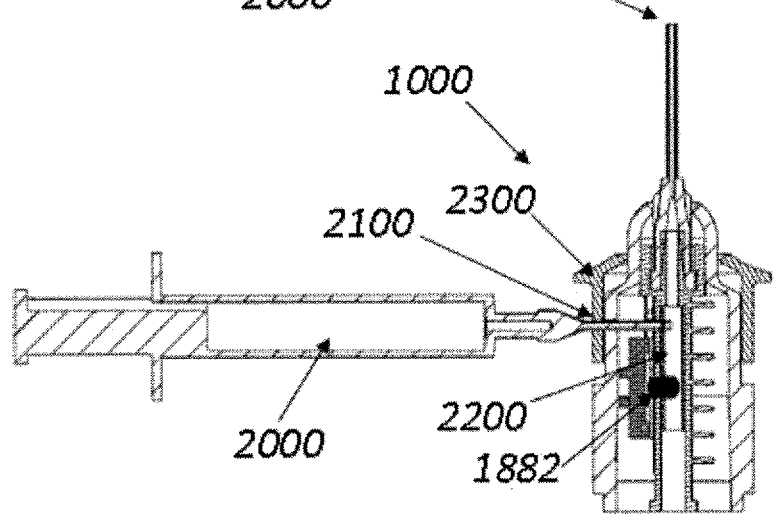

In reference to FIGS. 10A-D-11A-H, two exemplary embodiments of nozzles (1100) are shown. In both FIGS. 10A-D and FIGS. 11A-H, the nozzle (1100) has a tip extension (1110) with a larger diameter than the nozzle, the tip extension substantially surrounding the distal end of the nozzle (1100). In FIGS. 9A-C, the nozzle tip is substantially conical, lacking the optional tip extension (1110).

Figures 10A, 10B, 10C, 10D:
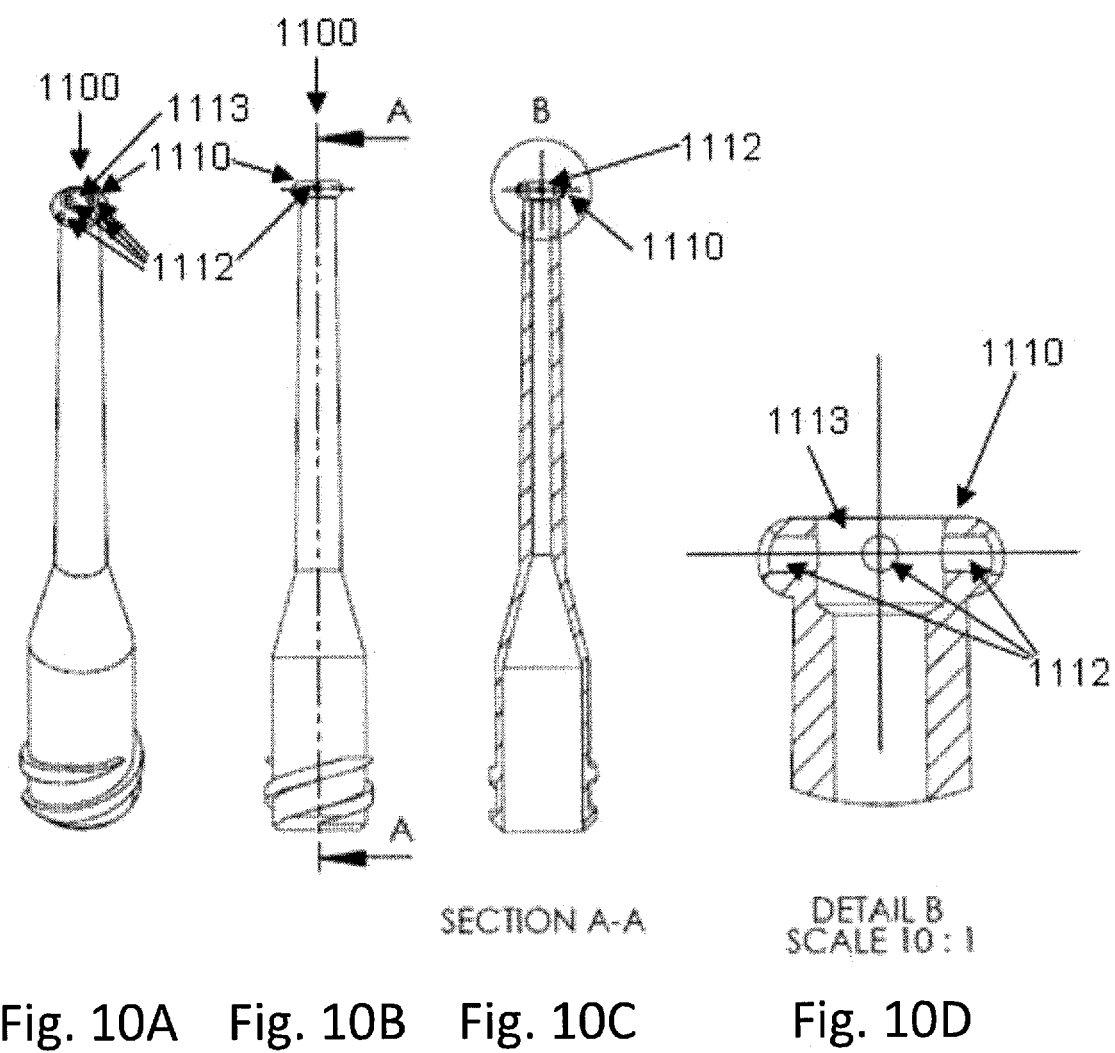

In the exemplary embodiment of both FIGS. 10A-D and FIGS. 11A-H, the tip extension (1110) has holes (1112) in it to allow substance to exit laterally from the extension, and the tip (1110) has at least one hole (1113) in its distal end to allow substance to exit longitudinally from the nozzle (1100). FIG. 10A-D shows an embodiment of a nozzle (1100) with a tip extension (1110). FIG. 10A shows a perspective view of the nozzle (1100) from the distal end, while FIG. 10B shows a side view. FIG. 10C shows a cross-section of the nozzle along the line AA in FIG. 10A, while FIG. 10D shows an enlarged view of the circled region B at the tip of the nozzle in FIG. 10C, showing the tip of the nozzle and the tip extension in more detail. The holes (1112) in the tip extension (1110) and the hole (1113) in the tip can be clearly seen. In some embodiments, the nozzle (1110) has only lateral holes (1112), so that no substance escapes from the distal end of the nozzle (1110).

In preferred embodiments, the distal end of the tip extension does not comprise any longitudinal protuberances, being substantially flat in the area around the opening (1113) and, where non-planar, extending proximally from the plane of the opening.

Figures 11A, 11B, 11C, 11D:
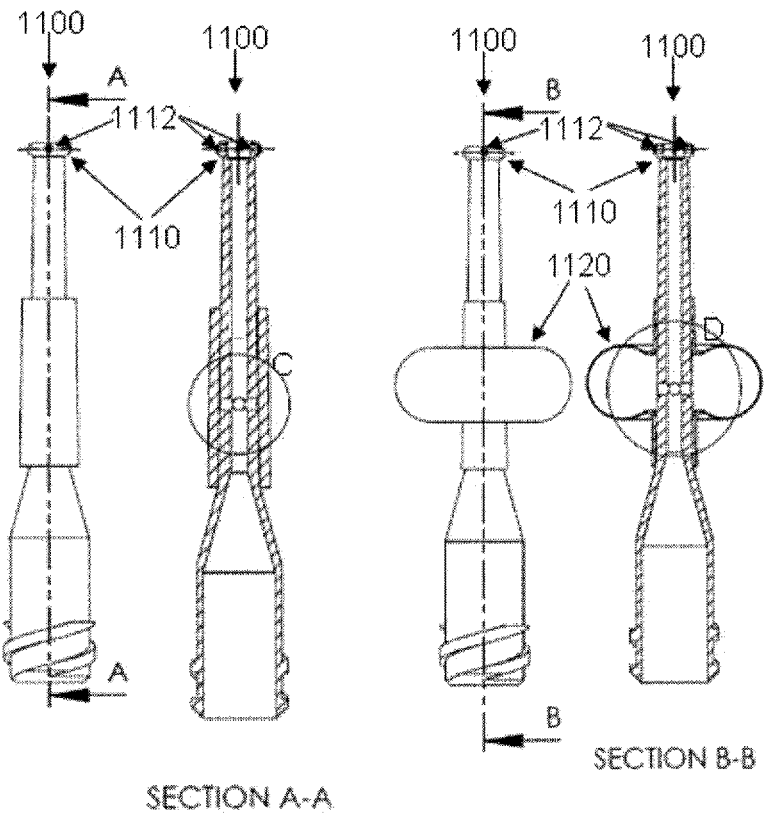
Figures 11E, 11F, 11G, 11H:
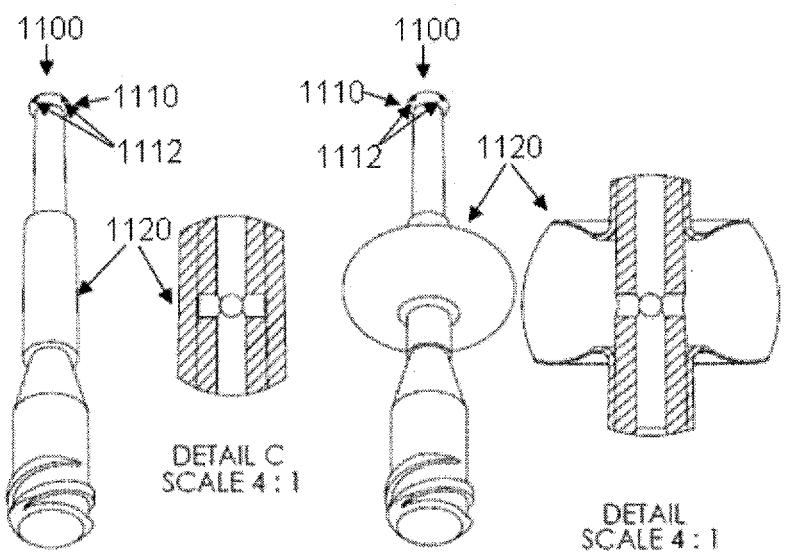

In order to prevent material from escaping from the nasal passages or entering undesired areas in the nasal cavity, in some embodiments, the nozzle comprises a medial extension, an expandable portion (1120). FIGS. 11A-H show an embodiment of a nozzle with a tip extension (1110) and an expandable portion (1120). FIGS. 11E and 11G show perspective views of the nozzle from the proximal end, while FIGS. 11A and 11C show side views of the nozzle (1100). FIGS. 11B and 11D show cross-sections of the nozzle (1100) along the lines AA in FIG. 11A and BB in FIG. 11C, respectively. FIG. 11F shows an enlarged view of the circled region C in the center of the nozzle in FIG. 11B, while FIG. 11H shows an enlarged view of the circled region D in the center of the nozzle in FIG. 11D.

FIGS. 11A, 11B, 11E and 11F show the nozzle with unexpanded expandable portion, while FIGS. 11C, 11D, 11G and 11H show the nozzle with expanded expandable portion.

In the exemplary embodiments of FIGS. 10A-D and 11A-H, the tip extension and the expanded medial extension are substantially toroidal; in other embodiments, they can be substantially spherical, substantially ovoid, substantially ellipsoidal, substantially the frustum of a cone (preferably with a rounded distal edge), substantially conic (preferably with a rounded distal edge) and any combination thereof.

The nozzle tip and the tip extension (1110) have a number of holes (1112, 1113) which fluidly connect the bore of the nozzle (1100) to the exterior of the device, allowing material to exit from the interior of the device. In the exemplary embodiments shown, there is a hole (1113) (FIGS. 10A-D; not shown in FIGS. 11A-H) in the distal end of the nozzle and four holes (1112) in the tip extension (1100). Both the extension and the distal end of the nozzle can have more or fewer holes and, in some embodiments, one or the other can have no holes. The holes (1112) can be regularly spaced around the periphery of the extension, the holes (1112) can be irregularly spaced around the periphery, the holes (1112) can be concentrated in a predetermined part of the periphery, and any combination thereof. Similarly, the holes in the distal end of the tip can be regularly or irregularly spaced in the tip.

In some embodiments, the extension (1110) can be padded, can comprise soft material, can comprise flexible material and any combination thereof.

Extensions, both tip extensions and medial extensions, can have a number of functions. A non-limiting list of such functions is (1) ensuring proper positioning of the nozzle (1100) in the nasal passages, where the proper position can be the nozzle (1100) centralized in the nasal passages, the nozzle (1100) touching a predetermined portion of the nasal passages, or the nozzle (1100) closer to a predetermined portion of the nasal passages, (2) sealing the nasal passages so that material can not escape therefrom, (3) sealing the nasal passage so that substance does not contact undesired portions thereof, (4) sealing the nasal passage so that substance remains in a predetermined region of the nasal passage, (5) reducing the discomfort of contact between the nozzle and the nasal passages, especially in embodiments where the extension is intended to seal against the walls of the nasal passages, by providing a soft and/or flexible contact region and any combination thereof. Proper positioning can be for the purpose of improving delivery of a substance to a predetermined area, preventing clogging of the holes by nasal secretions, preventing clogging of the holes by contact with the nasal passages, mucosa and any combination thereof.

Nozzle extensions, both those that are expanded during the activation procedure and those that have a predetermined shape and do not expand, can either (1) be attached to the nozzle in a way that they are removed from the nasal cavity with the nozzle tip itself, or (2) have the option of being releasable from the nozzle tip so that they stay in the nasal cavity until they are pulled out by the user or by a caregiver, or any combination thereof. In embodiments where at least one nozzle extension remains in a nasal cavity, preferably, the nozzle extension or extensions are removed after a predetermined time, preferably a short time.

In some embodiments, the holes (1112) in the nozzle (1100) do not lie substantially in a plane perpendicular to the main longitudinal axis of the nozzle (1100). In such embodiments, the holes (1112) can lie along a line parallel to the main longitudinal axis of the nozzle (1100), along a line forming a spiral around the nozzle (1100), irregularly in the distal portion of the nozzle (1100), regularly spaced in the distal portion of the nozzle (1100), and any combination thereof.

Therefore, dispersion of the drug can be substantially from a ring perpendicular to the main longitudinal axis of the nozzle (1100) (holes (1112) around the edge of the extension (1110), from a circle perpendicular to the main longitudinal axis of the nozzle (1100) (holes (1113) in the distal tip of the nozzle (1100), from a line (holes (1112) parallel to the main longitudinal axis of the nozzle (1100) or in a spiral around the main longitudinal axis of the nozzle (1100), or from at least part of the surface of a volume extending along the side of the nozzle (1100).

In some embodiments, the size of the tip extension (1110) is selected so that the extension (1110) is in contact with the nasal passages substantially along its entire circumference. In such embodiments, material exiting holes (1113) in the distal tip of the nozzle (1100) or holes (1112) on the distal face of the extension (1110) can not reach regions proximal to the extension (1110) and will reach only regions deeper in the nasal passages than the extension (1110). In such embodiments, the substance will reach the upper parts of the nasal passages.

Material exiting from holes (1112) in locations where the extension (1110) is in contact with the nasal passages will deposit directly on the walls of the nasal passages. In such embodiments, deposition is in a very narrow band; the location of the band can be tailored for the material of interest.

Material exiting holes (1112) proximal to the region of the extension (1110) in contact with the walls of the nasal passages will be unable to reach locations distal to the region of the extension (1110) in contact with the walls of the nasal passages and will therefore deposit in the lower parts of the nasal passages.

Returning to FIGS. 11A-H, in this embodiment, the expandable portion (1120) surrounds the nozzle (1100). In other embodiments, the expandable portion (1120) can partially surround the nozzle (1100). A single expandable portion (1120) or a plurality of expandable portions (1120) can be used. An expandable portion can be on the surface of the nozzle or it can be stored within the nozzle, popping out when it expands. An expandable portion can have a predetermined shape when expanded. The shape of the outward-facing part of an expandable portion can be part of the surface of a spheroid, can be part of a cylinder, a part of a cone, or can conform to the shape of a predetermined portion of a nasal passage. Such shaping can help ensure that, on inflation, the expandable portion or portions gently guide the nozzle so that it rests in the position with respect to the nasal passages or in the correct portion of the nasal passages. It can also reduce the user's discomfort when the device is in place or, if detachable from the device, it can seal the nasal passage for a time, before being removed by the user or a caretaker.

The expandable portion (1120) is preferably inflated after insertion of the device into the nasal passage. Inflation can be before or at the time of activation of the device.

FIGS. 12-14A-D, show an embodiment of a single-use device comprising a multi compartment drug container.

Figure 12:
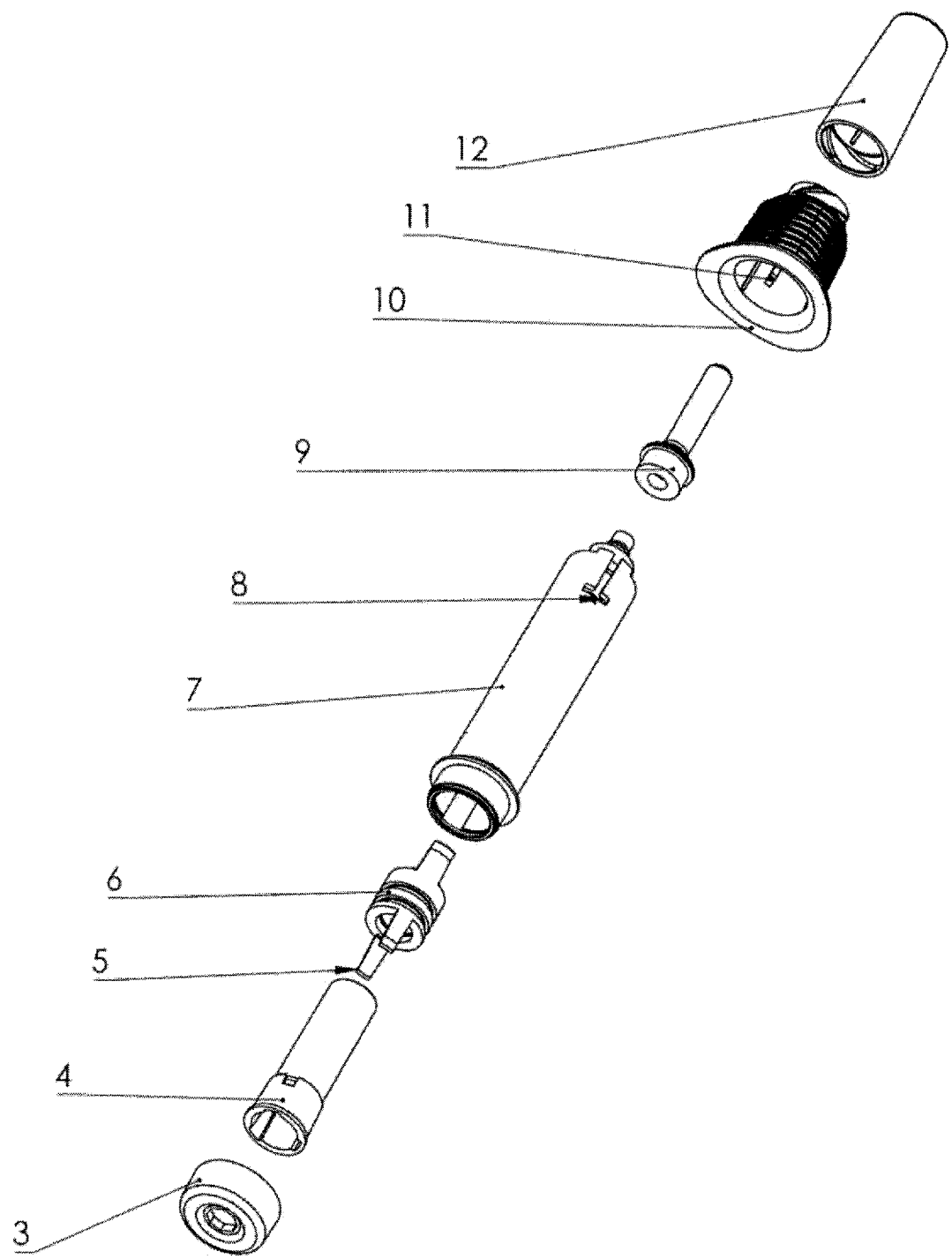

FIG. 12 shows an exploded view of an embodiment of the device. The embodiment of FIG. 12 comprises a base cover (3), a drug container housing (4) to hold a drug container (18, not shown; see FIG. 13B), a drug container holder stopper (5), a body (7) which comprises compressed gas chamber, a nose piece (9), an activation button (10) and a nose piece cover (12).

FIG. 13A-D shows this embodiment of the device, before activation.

Figure 13A:
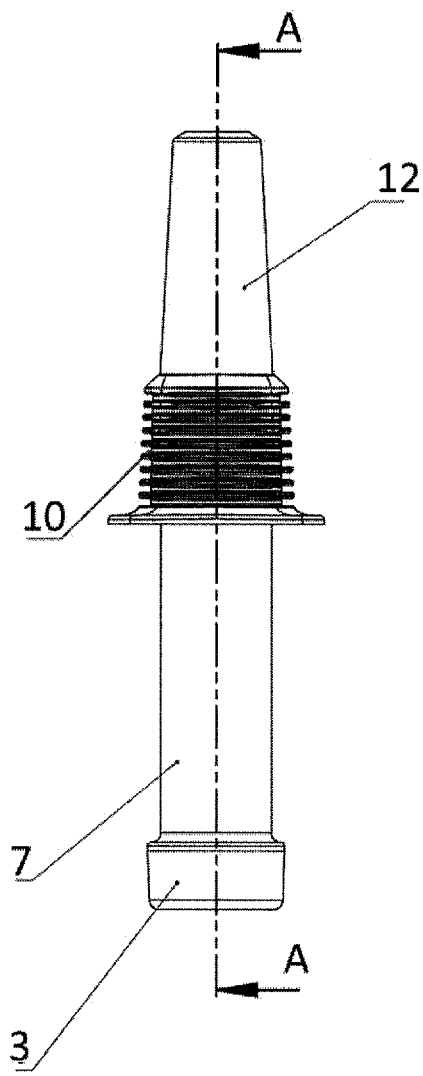

FIG. 13A shows this embodiment of the device assembled. The base cover (3), the body (7), the activation button (10) and nose piece cover (12) can be seen.

Figure 13B:
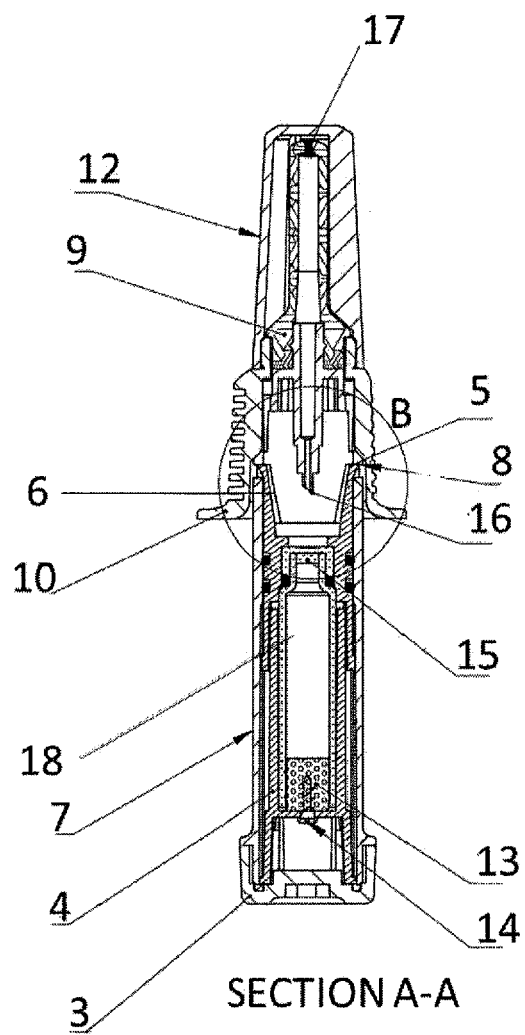

FIG. 13B shows a cross-section of this embodiment of the device, along the line A-A. Inside the body (7) is a drug container housing (4) and, within that, a drug container (18) configured to contain one or more substances. Between the drug container housing (18) and the body (7) is compressed gas. The drug container (18) configured to contain one or more substances, usually medicaments or medicament precursors, as disclosed above. The base cover (3) and a plunger anchor (14) are anchored into a drug container plunger (13) at the proximal end of the drug container (18). Sealing the drug container (18) at its distal end is a drug container cover (15), preferably made of a biocompatible material. The drug container (18) is prevented from moving distally by a drug container holder (6), with the drug container holder (6) clasping the neck of the drug container (18) and preventing it from moving. The activation button (10) slidably covers the drug container holder (6), the distal end of the body (7), and the proximal end of the nose piece (9). Before activation, a flange, the drug container holder stopper (5, see FIG. 13C) at the distalmost end of the drug container holder (6) sits in the activation rib slot (8). A needle (16) is configured to pierce the drug container cover (15) during activation. A nose piece (9) is attached to the distal side of the body (7) and passes through the activation button (10). When not in use, the nose piece (9) can be covered by a nose piece cover (12).

Figure 13C:
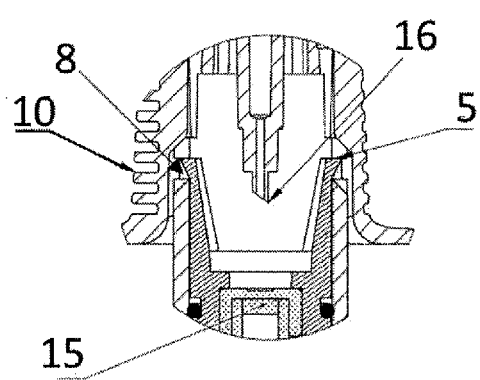

FIG. 13C shows an enlarged view of the area inside the circle B in the cross-section shown in FIG. 13B, before activation. The activation button (10), needle (16), drug container cover (15), and drug container holder stopper (5) can be seen more clearly, with the drug container holder stopper (5) resting in the activation rib slot (8).

Figure 13D:
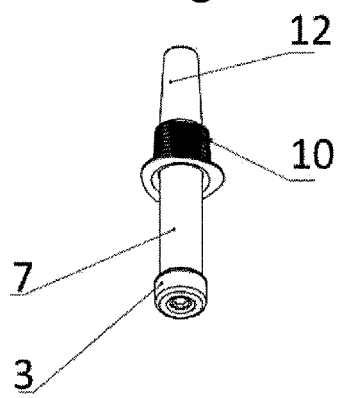

FIG. 13D shows another view of the device of FIG. 13A, with the nose piece cover (12). The body (7), activation button (10), and nose piece cover (12) are seen.

FIG. 14A-D shows this embodiment of the device of FIG. 13A after activation.

FIG. 14A shows the post-activation embodiment of the device assembled, without a nose piece cover (12). The base cover (3), the body (7), the activation button (10) and the nose piece cover (10) can be seen.

FIG. 14B shows a cross-section of this embodiment of the device, along the line A-A. Inside the body (7) is a drug container housing (4) and, within that, a drug container (18) configured to contain one or more substances, typically medicaments or medicament precursors. Between the drug container housing (18) and the body (7) is compressed gas. During activation, the drug container (18) is emptied of the substances it contains. The base cover (3) and a plunger anchor (14) are anchored into a drug container plunger (13) at the proximal end of the drug container (18). Sealing the drug container (18) at its distal end is a drug container cover (15), preferably made of a biocompatible material. The drug container (18) is prevented from moving distally by a drug container holder (6), with the drug container holder (6) clasping the neck of the drug container (18) and preventing it from moving. The activation button (10) slidably covers the drug container holder (6), the distal end of the body (7), and the proximal end of the nose piece (9). Before activation, a flange, the drug container holder stopper (5, see FIG. 13C) at the distalmost end of the drug container holder (6) sits in the activation rib slot (8). A needle (16) is configured to pierce the drug container cover (15) during activation. A nose piece (9) is attached to the distal side of the body (7) and passes through the activation button (10). The tip of the nose piece (9) is pierced by an aerosol release orifice, through which the aerosol generated within the device can exit the device.

FIG. 14C shows an enlarged view of the area inside the circle B in the cross-section shown in FIG. 14B, before activation. The activation button (10), needle (16), drug container cover (15), and drug container holder stopper (5) can be seen more clearly FIG. 14D shows another view of the device of FIG. 14A, with the nose piece cover (12). The body (7), activation button (10), and nose piece (9) are seen. The needle (16) has pierced the drug container cover (15), allowing the drug to escape, and the drug container holder stopper (5) is no longer in the activation rib slot (8).

FIG. 14D shows an external view of the device of FIG. 13A, without the nose piece cover (12).

For the device of FIGS. 12-14A-D, removal of the nose piece cover (12) allows device activation. Pushing the activation button (10) towards the base (7) releases the drug container (18) held by the drug container holder (6) from its locking in the activation rib slot (8) and allow the drug container (18) to move towards the needle (16). While the drug container (18) moves, the drug container plunger (13) is extracted from it. The resulting gap between the proximal end of the drug container plunger (13) and the distal end of the interior of the base cover (3) allow the compressed gas to pass through the drug container (18). This initial air passage pushes the drug container (18) further towards the needle, resulting in puncturing of drug container cover (15) by the needle (16) and substance release through the aerosol release orifice (17) as a result of the open air passage.

FIGS. 15A-D and 16A-D show embodiments of a device with ball-type (2) drug container dividing and mixture elements. The nose piece is not shown. With two dividing elements, 3 substances can be stored in the device prior to delivery. FIG. 15A-D shows the device before activation, while FIG. 16A-D shows the device after activation.

FIG. 15A shows the exterior of the device from the side, while FIG. 15C shows the exterior of the device from the top. FIG. 15B shows a cross-section of the device along the line A-A in FIG. 15A, while FIG. 15D shows an enlarged view of the area within the circle B in FIG. 15B.

As shown in the cross-section of FIG. 15B, inside the body (7) is a drug container housing (1) and, within that, a drug container (4) configured to contain three separate substances. Between the drug container housing (1) and the body (7) is compressed gas. The drug container (4) configured to contain three substances, A, B and C; substances A, B and C being separated by dividing and mixing elements (2, 3). The base (14) comprises an integral plunger anchor, with the plunger anchor anchored into a drug container plunger (13) at the proximal end of the drug container (4). Sealing the drug container (4) at its distal end is a drug container cover (15), preferably made of a biocompatible material. The drug container (4) is prevented from moving distally by a drug container holder (6), with the drug container holder (6) clasping the neck of the drug container (4) and preventing it from moving. The activation button (10) slidably covers the drug container holder (6), the distal end of the body (7), and the proximal end of the nose piece (9). Before activation, as in FIGS. 13A-D, a flange, the drug container holder stopper (5, see FIG. 13C) at the distalmost end of the drug container holder (6, see FIG. 13C) sits in the activation rib slot (8, see FIG. 13C). A needle (16) is configured to pierce the drug container cover (15) during activation. A nose piece (9) is attached to the distal side of the body (7) and passes through the activation button (10). The distal end of the nose piece (9) comprises an aerosol release orifice (17) to allow passage of an aerosol from the interior of the device to its exterior.

FIG. 15C shows a view of the device of FIG. 15A, from the top.

FIG. 15D shows an enlarged view of the area inside the circle B in the cross-section shown in FIG. 15B, before activation. The gap between the drug container housing (1) and drug container (4) can be seen more clearly. Inside the drug container (4), substances A and B are separated by dividing/mixing element 3, while substances B and C are separated by dividing/mixing element 2. The proximal end of the drug container housing (1) surrounds the drug container plunger (13, see FIG. 15B), sealing the proximal end of the drug container (4), FIG. 16A-D shows the embodiment of the device of FIG. 13A-D after activation.

FIG. 16A shows the exterior of the device from the side, while FIG. 16C shows the exterior of the device from the top. FIG. 16B shows a cross-section of the device along the line A-A in FIG. 16A, while FIG. 16D shows an enlarged view of the area within the circle B in FIG. 16B.

As shown in the cross-section of FIG. 16B, inside the body (7) is a drug container housing (1) and, within that, a drug container (4). Before activation, between the drug container housing (1) and the body (7) was compressed gas, which exited its storage area via the drug container (4). After activation, the dividing and mixing elements (2, 3) have substantially exited the drug container (4), but are prevented by the drug container holder (6) from entering the nose piece (9). The dividing and mixing elements (2, 3) cannot either block the nose piece (9) or exit the device and therefore are prevented from entering the body of a user. The base (14) with plunger anchor anchored into the drug container plunger (13, see FIG. 15B) is now separate from the proximal end of the drug container (4), allowing the compressed gas to enter the base of the drug container (4); the arrows show the direction of gas movement. The drug container cover (15), has been pierced by the needle (16), allowing an aerosol to form from the gas and the substances, during activation, pass through the nose piece (9), through the aerosol release orifice (17) and pass from the interior of the device to its exterior.

In some embodiments of the device, the substances can also be held inside the nosepiece, as demonstrated in FIGS. 17-20A-B.

FIG. 17 shows an embodiment of a device with a drug container or substance holder in the nose piece. The device is shown as configured for storage or transport. It comprises a base (5), a compressed gas chamber (4), which can be integral with the base or in communication with the base (5), activation holders (3), and a nosepiece (not shown) protected by a nosepiece cover (2). As in the embodiments of FIGS. 13-16, activation is by compressing the upper end of the device toward its base, by holding the activation holders (3) with the fingers and the bottom of the base (5) with the thumb, and bringing the fingers toward the thumb.

FIG. 18 shows an exploded view of the parts of the device in FIG. 17. Inside the base (5) is an air chamber gate (8) for control of passage of gas from the compressed gas chamber (4). The air chamber gate (8) comprises a stopper (10) at its proximal end, with the stopper (10) resting against a shoulder in the base (5), with the shoulder preventing proximal movement of the air chamber gate (8); and a gate O-ring (9) proximal to the air chamber gate (8) to ensure an air-tight seal between the air chamber gate (8) and the base (5). A septum (7) surrounds the distal end of the air chamber gate (8), providing an air-tight seal between the base unit (5) and the compressed gas chamber (4). The device comprises a drug chamber (6), which can contain a single-substance or multiple substances, as disclosed above; a compressed gas chamber (4), activation holders (3) and a nosepiece (4A), and a nosepiece cover (2) with activation safety locks (2A) to prevent both accidental activation of the device and loss of the cove during storage or transport. In preferred embodiments, the compressed gas chamber (4), activation holders (3) and nosepiece (4A) form an integral unit; in other embodiments, at least one of the compressed gas chamber (4), activation holders (3) and nosepiece (4A) is a separate unit, joined to the others by any means known the art.

Figure 17:
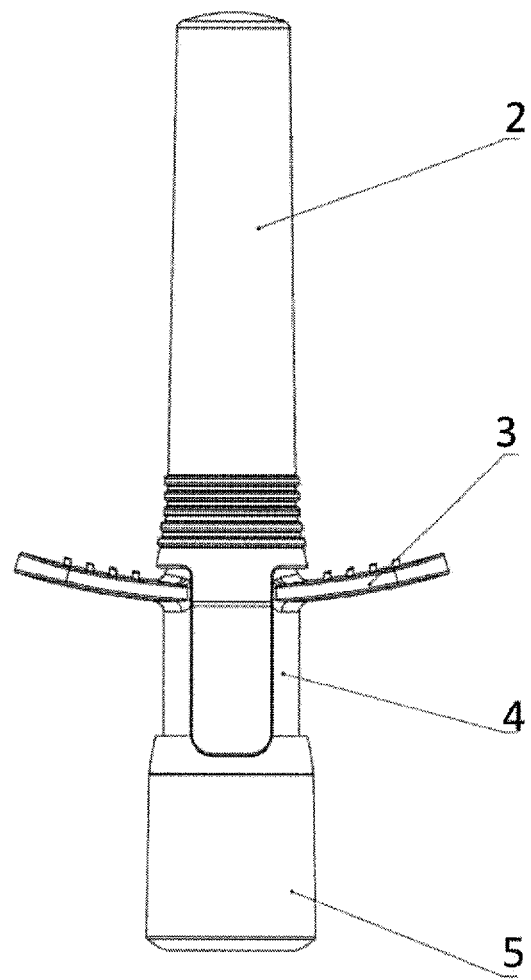
FIG. 17 shows pressure developed in a closed tube after discharge from devices into the tube.
Figure 18:
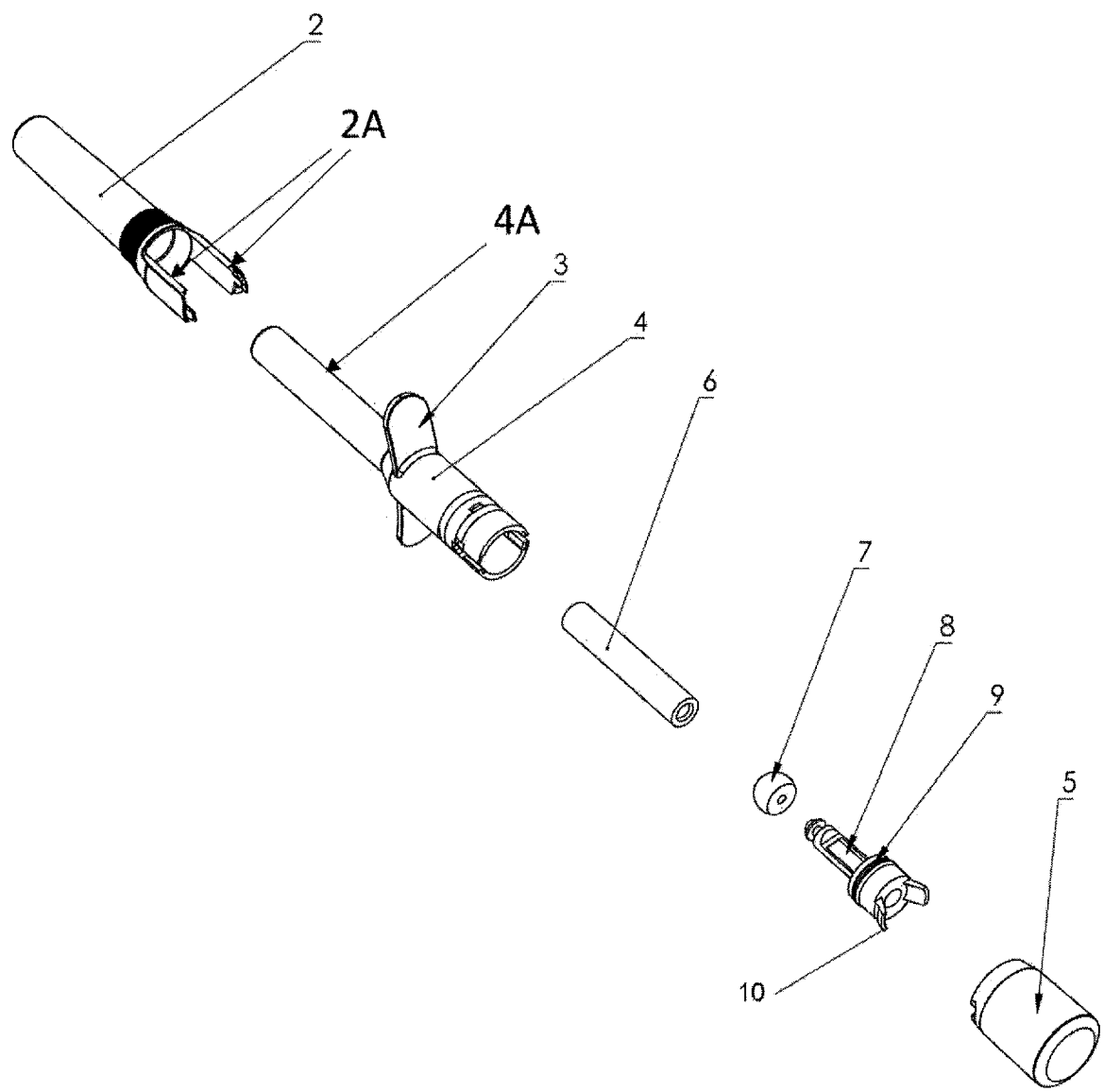
FIG. 18 shows a nasal cast and results of discharge of devices into the nasal cast.

FIG. 19B shows a cross-section of the device of FIGS. 17 and 18, before activation, with the cross-section taken along the line A-A of FIG. 19A, which shows the exterior of the device, illustrating the nose piece cover (2); activation holders (3), compressed air chamber (4) and the activation mechanism base (5).

FIG. 19C is an enlarged view of the area inside the circle B in FIG. 19B, showing the stopper, resting on a shoulder in the base unit (5).

The device is shown with a substance container containing substance in the nose piece. The device comprises a nose piece cover (2) with an activation safety lock (2), activation holders (3), a compressed air chamber (4) and an activation mechanism base (5). After the nose piece cover with its activation safety lock (2, see FIG. 18) is removed, activation is allowed. The at least one substance is held inside the drug container (6), with the drug container (6) sealed in place by a septum (7) at its proximal end and by a protruding element at distal end of the nose piece cover (2), which blocks the aerosol release orifice at the distal end of the nose piece (4A); the nose piece cover (2) being held in place by the activation safety lock. At the proximal end of the device are the activation mechanism base (5), a unit which has two zones/functions one is the air chamber gate (8) and the other one is the stopper (10), and a gate O-ring (9). The at least one substance is held in the drug container (6) between the drug container dividing and mixture elements (12). The compressed air is locked between the compressed air chamber wall (4) and the air chamber gate (8). Removal of the nose piece cover and activation safety lock (2) releases the safety lock anchor (11) and allows activation.

Upon activation, the stopper (7) is pressed inward; allowing the air chamber gate (8) to slide proximally, since the proximal area of the stopper exposed to the pressure is greater than the distal area of the stopper exposed to the same pressure. A gap is generated between the septum (7) and the drug container (6), allowing air passage through the at least one substance and generation of aerosol. In embodiments where drug container dividing and mixture elements (12) are used, they are released to a wider zone in the drug container (6) to allow substance mixing and release, contact between the substances and the air and aerosol formation and delivery.

FIG. 20B shows a cross-section of the device of FIGS. 17-19A-C, after activation, with the cross-section taken along the line A-A of FIG. 20A, which shows the exterior of the device, illustrating the activation holders (3), compressed air chamber (4) and the activation mechanism base (5).

After activation, the dividing and mixture elements (12) have been moved to a holding chamber at the tip of the nose piece and the drug container (6) is empty. The air chamber gate (8) has been moved proximally by the air pressure so that the stopper (5) rests against the interior of the bottom of the base (5), leaving a gap between the septum (7) and the compressed air chamber (4). The gate O-ring (9) still forms a seal around the stopper.

FIG. 21A-C illustrates an embodiment of a drug container (6). FIG. 21A shows the exterior of the container (6), with FIG. 21B showing a cross-section of the drug container (6) before activation taken along the line A-A of FIG. 21A. FIG. 21C shows the exterior of the drug container after activation. In FIG. 21B, there is one dividing and mixing unit (12) at each end of the drug container (6), thus effectively sealing the drug container (6). In FIG. 21C, both dividing and mixing units (12) have been displaced from the interior of the drug container (6.)

FIG. 22-34A-E illustrate embodiments of devices with a dose-adjustable drug chamber, where it is possible for a user to adjust the amount of medicament delivered in each dose, either for a single-use device or for a multi-use device.

FIG. 22 shows an embodiment of the body of a nasal delivery device. The nosepiece is not shown. The body comprises a base (10), an air chamber gate (12) with a first gate O-ring (11) at its proximal end and a second gate O-ring (13) at its distal end. The first gate O-ring (11) corresponds to the gate O-ring of the embodiments of FIGS. 18-21C and the second gate O-ring corresponds to the septum of FIGS. 18-21C. The distal end of the air chamber gate (12) is covered by a drug container base cover (14) which comprises a biocompatible material to ensure that substance that is to contact living tissue only contacts biocompatible material before the contact with living tissue. The compressed gas chamber (15) will fit over the air chamber gate (12), with the first gate O-ring (11) and the second gate O-ring (13) providing airtight seals before activation so that compressed gas is storable between the air chamber gate (12) and the compressed gas chamber (15). The compressed gas chamber (15) is connectable at its distal end with a nose piece (not shown). The distal portion of the compressed gas chamber (15) comprises activation holders (30)

FIG. 23A-D shows an embodiment of the body of FIG. 22, as assembled, before activation. FIG. 23A shows the exterior of the body, while. FIG. 23B shows a cross-section taken along the line A-A in FIG. 23A. FIG. 23C is an enlarged view of the circled section B in FIG. 23B, while FIG. 23D is a perspective view of the body of FIG. 23A. Activation is by compressing the upper end of the device toward its base, by holding the activation holders (30) with the fingers and the bottom of the base (10) with the thumb, and bringing the fingers toward the thumb.

As shown in FIGS. 23A and 23D, in the embodiment of FIGS. 22-23A-D, the base of the device forms the activation button (10), to, activate, the activation button (10) is pressed upward while the compressed gas chamber (gas chamber (15) is held stationary by fingers on the activation holders (30). The nosepiece is attachable to the compressed gas chamber (15) by means of the nose piece connector slot (15B); a protuberance on the nose piece engages with the nose piece connector slot (15B); permitting fast and easy replacement of the nose piece.

As shown in FIG. 23B, the activation button (10) comprises a gate anchor (10A), a shoulder on which the air chamber gate stopper (12A) rests before activation. This to prevent movement of the air chamber gate (12) before activation. The first gate O-ring (11), at the proximal end of the gate anchor (10A) and the second gate O-ring (13), at its distal end, provide airtight seals before activation so that compressed gas is storable between the air chamber gate (12) and the compressed gas chamber (15). The distal end of the air chamber gate (12) is covered by a drug container base cover (14) which comprises a biocompatible material to ensure that substance that is to contact living tissue only contacts biocompatible material before the contact with living tissue. The compressed gas chamber (15) is connectable at its distal end with a nose piece (not shown) by means of the nose piece connector slot (15B).

FIG. 23C, the enlargement of the area within the circle B of FIG. 23B, clearly shows the gate anchor (10A), with the air chamber gate stopper (12A) resting on it.

FIG. 24A-D shows an embodiment of the body of FIG. 22, as assembled, after activation. FIG. 24A shows the exterior of the body, while. FIG. 24B shows a cross-section taken along the line A-A in FIG. 24A. FIG. 24C is an enlarged view of the circled section B in FIG. 24B, while FIG. 24D is an enlarged view of the circled section C in FIG. 24B. Activation is by compressing the upper end of the device toward its base, by holding the activation holders (30) with the fingers and the bottom of the base (10) with the thumb, and bringing the fingers toward the thumb.

As shown in FIGS. 24A and 24D, in the embodiment of FIGS. 22-23, the base of the device forms the activation button (10), to activate, the activation button (10) is pressed upward while the compressed gas chamber (gas chamber (15) is held stationary by fingers on the activation holders (30). The nosepiece is attachable to the compressed gas chamber (15) by means of the nose piece connector slot (15B); a protuberance on the nose piece engages with the nose piece connector slot (15B); permitting fast and easy replacement of the nose piece.

As shown in FIG. 23B, the activation button (10) comprises a gate anchor (10A), a shoulder on which the air chamber gate stopper (12A) rested before activation. During activation, the air chamber gate stopper (12A) is pressed inwards, so that the air chamber gate (12) moves proximally, opening up a gap (17) between the air chamber gate (12) and the distal end of the compressed gas chamber (15), allowing the gas (16) to exit the compressed gas chamber (15) through the gap, and to enter the nosepiece and forma an aerosol with the substance. The first gate O-ring (11), at the proximal end of the gate anchor (10A) still provide an airtight seal after activation, but the second gate O-ring (13), at its distal end, so that compressed gas is storable between the air chamber gate (12) and the compressed gas chamber (15) is no longer in contact with the compressed gas chamber (15). The distal end of the air chamber gate (12) is covered by a drug container base cover (14) which comprises a biocompatible material to ensure that substance that is to contact living tissue only contacts biocompatible material before the contact with living tissue. The compressed gas chamber (15) is connectable at its distal end with a nose piece (not shown) by means of the nose piece connector slot (15B).

FIG. 24C, the enlargement of the area, within the circle B of FIG. 24B, clearly shows the gate anchor (10A), with the air chamber gate stopper (12A) no longer in contact with it, but is resting near the base of the activation button.

FIG. 24D, the enlargement of the area within the circle C of FIG. 24B, clearly shows the distal end of the air chamber gate (12), the drug container base cover (14), the second gate O-ring (13) and the gap (arrow) permitting air to escape from the compressed gas chamber into the intermediate space and then to the nose piece (not shown).

FIG. 25A-C shows an embodiment of the device with the primary drug container in the nose piece cover. The medicament or substance is delivered from the primary drug container to a secondary drug volume in the nose piece. The nose piece cover can then be removed and the device activated to aerosolize and deliver the drug.

FIG. 25A shows the exterior of the device. It comprises an activation button (10), a compressed gas chamber (15), and a nosepiece (not shown) protected by a nose piece cover (20). At the distal end of the nose piece cover (20) is a primary drug container (not shown) in a drug container housing (21). The embodiment also comprises an indicator window (22) to determine the quantity of drug remaining in the primary drug container.

FIG. 25B shows a cross-section of the device, taken along the line A-A in FIG. 25A. The base and aerosol generation and delivery mechanism are similar to those disclosed above in FIGS. 21A-C through 24A-D. The device comprises a nose piece (28) with an integral drug volume (29) in its proximal portion. The deliverable substance is stored in a primary drug container (24) near the distal end of the nose piece cover (20). The primary drug container (24) is sealed at its proximal end by a plunger stopper (25). A loading needle (26) is fixed to the nose piece cover (20), with a needle adaptor (27) to guide the loading needle's (26) proximal end so that the proximal end of the needle adaptor (27) passes through the orifice at the tip of the nose piece (28). As shown in FIG. 25B, unless drug is being loaded into the integral drug volume (29), the needle does not pierce the plunger stopper (25) and the primary drug container (24) remains sealed.

FIG. 25C shows a perspective view of the device. The indicator window (22) and the drug container housing (21) can be seen, as well as the nose piece cover (20), which terminates at its proximal end in a safety lock (2A) to prevent unwanted activation of the device.

FIG. 26 A-C shows the embodiment of the device of FIG. 25 during loading of the drug into the integral drug volume (29) from the primary drug container (24).

FIG. 26A shows the exterior of the device. It comprises an activation button (10), a compressed gas chamber (15), and a nosepiece (not shown) protected by a nose piece cover (20). At the distal end of the nose piece cover (20) is a primary drug container (not shown) in a drug container housing (21). The embodiment also comprises a volume scale (30), here a ratchet, to allow adjustment of the size of the dose.

FIG. 26B shows a cross-section of the device, taken along the line B-B in FIG. 26A. The base and aerosol generation and delivery mechanism are similar to those disclosed above in FIGS. 21A-C through 24A-D. As shown in FIG. 26B, a drug or medicament (24A) is being loaded from the primary drug container into the integral drug volume (29). Loading is activated by pressing the primary drug container (24) proximally. It then slides along the nose piece (28). The loading needle (26) is steadied by the needle adaptor (27). Pressing the primary drug container (24) proximally forces the loading needle (26) through the plunger stopper (25) and into the primary drug container (24). Drug (24A) can then flow through the loading needle (26) into the integral drug volume (29). Releasing the primary drug container (24) will cause it to move distally and remove the loading needle (26) from the plunger stopper (25). The nose piece cover (20) can then be removed and a dose of the drug can be administered.

FIG. 26C shows a perspective view of the device. The volume scale (30) and the drug container housing (21) can be seen, as well as the nose piece cover (20), which terminates at its proximal end in a safety lock (2A) to prevent unwanted activation of the device.

FIG. 27 illustrates removal of the nose piece cover or medicine chamber (5) from an aerosol delivery device (1) by pulling (arrow) the medicine chamber (5) away from the aerosol delivery device (1), FIG. 28A-D illustrates a device with a replaceable nose piece preloaded with a single dose of a medicament. The medicament can comprise one or more substances, as disclosed above. The device further comprises a nose piece cover with a removable top. FIGS. 28A and 28D show the exterior of the device with the nose piece cover in place, with FIG. 28A showing it from the side and FIG. 28C showing a perspective view. FIG. 28B shows a cross section taken along the line A-A in FIG. 28A and FIG. 28C provides a partially exploded view.

FIG. 28A shows an activation button (10) and compressed gas chamber (15), as disclosed above. The nose piece cover (40) has a removable orifice closure (41) at its distal end.

FIG. 28B shows a cross-section of the device. The nose piece cover (40) has a reversibly removable nose piece orifice cover (41). The nose piece (28), which comprises an integral drug volume (29); has, at its distal end, a nose piece cover pin (41A) to protect the distal end of the nose piece.

FIG. 28C shows a partially-exploded view of the device. The nose piece (28) is reversibly connectable to the activation button (10) and compressed gas chamber (15) by means of a nose piece connecting pin (42A) which slots into a connector slot (42B) at the distal end of the compressed gas chamber (15). The removable orifice closure (41) is shown separated from the nose piece cover (40). By this means, only the removable orifice closure (41) needs to be removed to replace a nose piece (28); there is no need to remove the entire nose piece cover (40). The safety lock (2A) to prevent accidental activation of the device is also shown.

FIG. 29A-D illustrates a device which can be loaded with a medicament, drug or substance via a syringe. FIGS. 29A and 29D show the exterior of the device, FIG. 29A from the side and FIG. 29D from an angle. FIG. 29B shows a cross section taken along the line A-A in FIG. 29A and FIG. 29C shows the loading needle.

As shown in FIG. 29A, the device comprises an activation button (10) and compressed gas chamber, as disclosed above. The nose piece cover (40) comprises a drug loading adaptor (45) and a reversibly removable drug loading adaptor cap (46) at its distal end. In the embodiment shown, the drug loading adaptor cap (46) is attached to the nose piece cover (40) by an integral flexible strip (46A), to prevent the drug loading adaptor cap (46) from getting lost.

As shown in FIG. 29A, a drug loading needle (47) is held firmly within the drug loading adaptor (45). The drug loading needle (47) extends from the top of the nose piece cover (40) through the distal end of the nose piece (42) to a drug storage volume near the proximal end of the nose piece (42). The distal portion of the drug loading needle (47) is configured by means of shape and size to accept the delivery end of a syringe (not shown). During storage and transport, the drug loading needle (47) is retained firmly in place with its distal portion help firmly between the closed drug loading adaptor cap (46) and the distal tip of the nose piece (42).

FIG. 29C shows the drug loading adaptor (45) with the drug loading needle (47) extending proximally therefrom.

FIG. 29D shows the nose piece cover (40), the drug loading adaptor cap (46) and the drug delivery device with activation button (10).

FIG. 30A-D shows the device of FIG. 29A-D with a syringe in place. The syringe can be a proprietary syringe, with a tip matched in shape and size to the opening in the distal portion of the drug loading needle (47) or it can be a commercial syringe with a tip that fits into the opening in the distal portion of the drug loading needle (47).

Figure 30A:
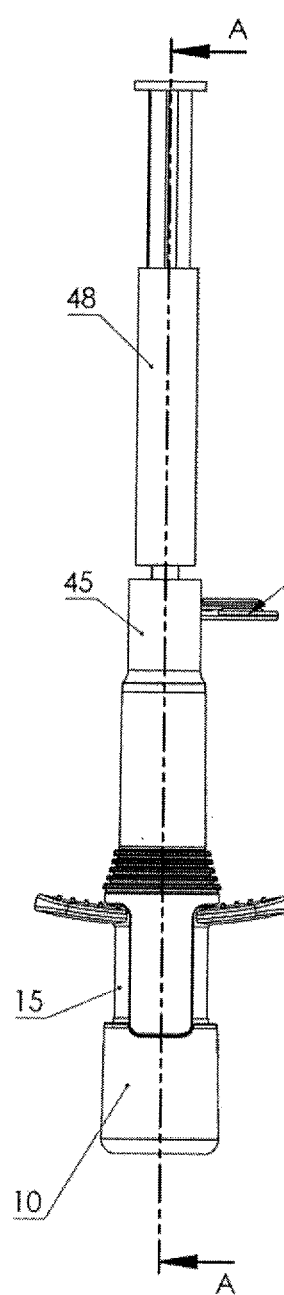

FIG. 30A shows a side view of the device with a labeled (49) loading syringe (48) in place. The drug loading adaptor cap (46) is open and the tip (not shown) of the loading syringe (48) is resting in the distal portion of the drug loading adaptor (45) and nose piece cover (40), with the nose piece cover in communication with the activation button (10) and compressed gas chamber (15) of the delivery device.

Figure 30B:
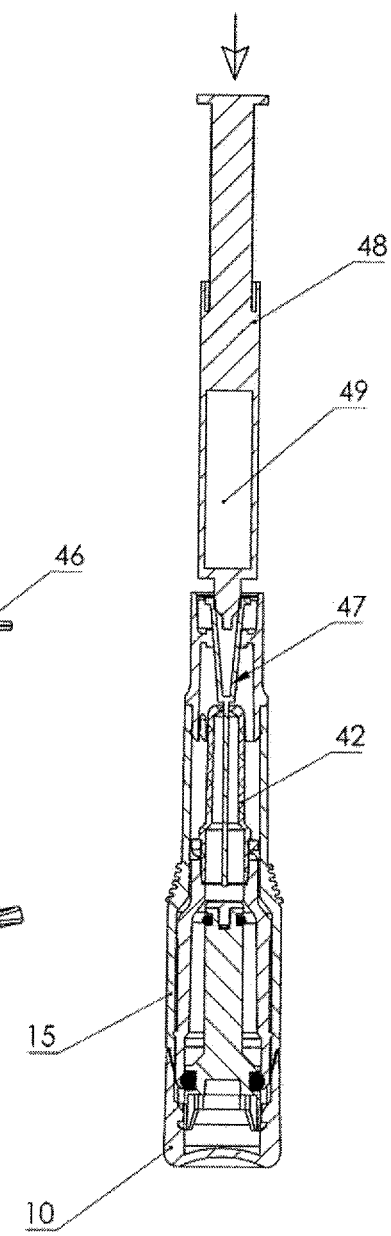

FIG. 30B shows a cross-section of the set-up of FIG. 30A, taken along the line A-A of FIG. 30A. The loading syringe (48) is resting in the distal portion of the drug loading needle (47). The proximal portion of the drug loading needle (47) passes through the nose piece (42). The nose piece (42) is attached, either reversibly or fixedly, to the activation button (10) and compressed gas chamber (15) of the delivery device.

Figure 30D:
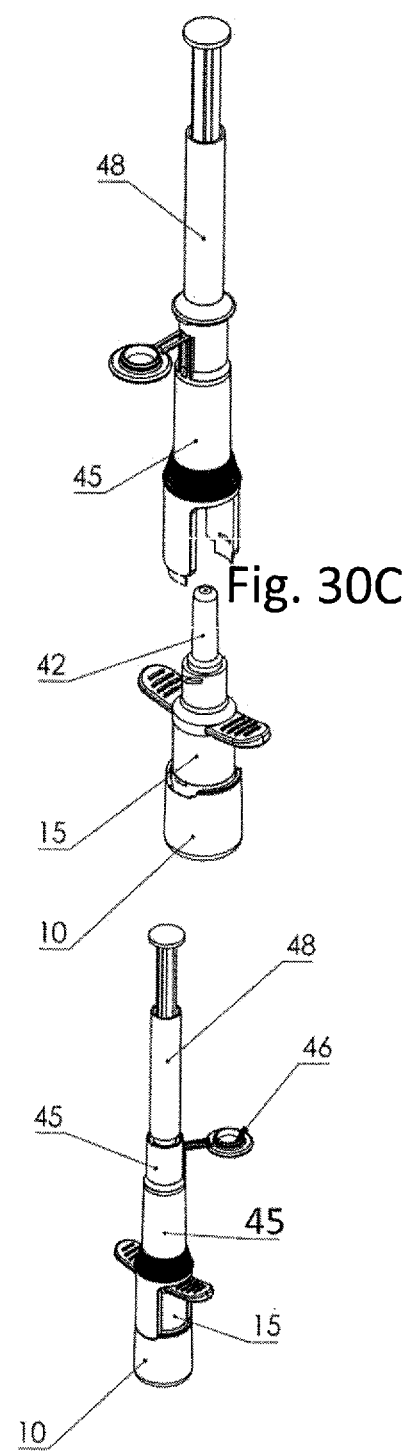

FIG. 30C-D shows how a loading syringe (48) in place in a drug loading adaptor (45), is connectable to a drug delivery device, comprising nose piece (42), compressed gas chamber (15) and activation button (10). FIG. 30C shows the loading syringe (48) in place in a drug loading adaptor (45), with the drug loading adaptor (45) in position to be attached to the delivery device. FIG. 30D shows the loading syringe (48) and drug loading adaptor (45), with the drug loading adaptor cap (46) open, attached to the compressed gas chamber (15) and activation button (10) of the delivery device.

Figure 31:
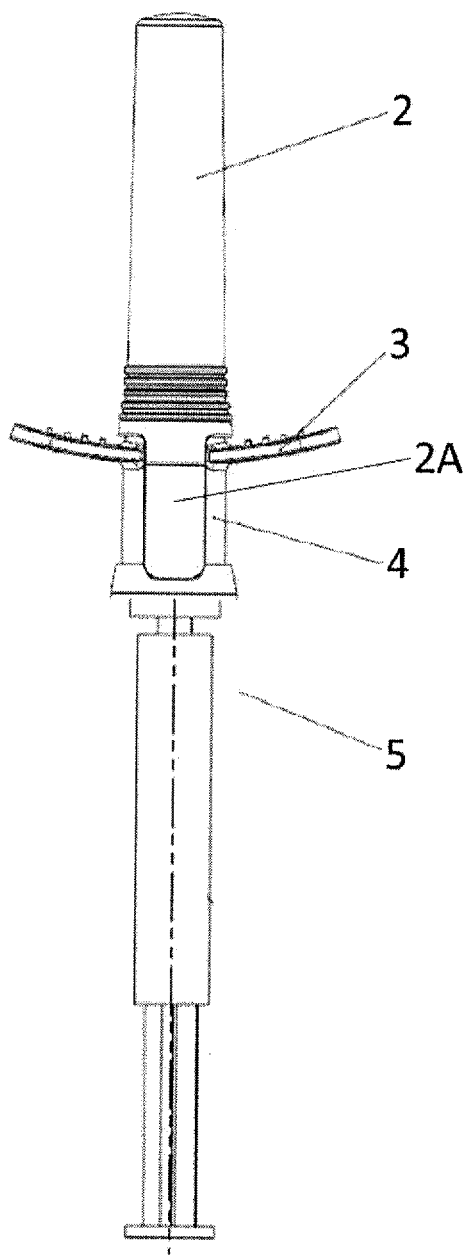

FIG. 31 shows an embodiment of delivery device where adjustment of the size of the dose is made from the proximal end—the opposite end of the device from the adjustment mechanisms disclosed above. The nose piece is covered by a nose piece cover (2) with a safety lock (2A) to prevent accidental activation of the device. The safety lock (2A) is latched to the compressed gas chamber (4) of the delivery device. Proximal to the compressed gas chamber (4) is an activation mechanism base (5). The activation holders (3) are also shown.

For many medicines, one dose is supplied to each nostril, with the patient receiving two doses altogether. In the prior art, for a single-dose delivery device, this required two delivery devices, with the consequent waste of packaging material, waste of time spent unpacking two devices, both of which tend to reduce patient compliance.

Figure 32A:
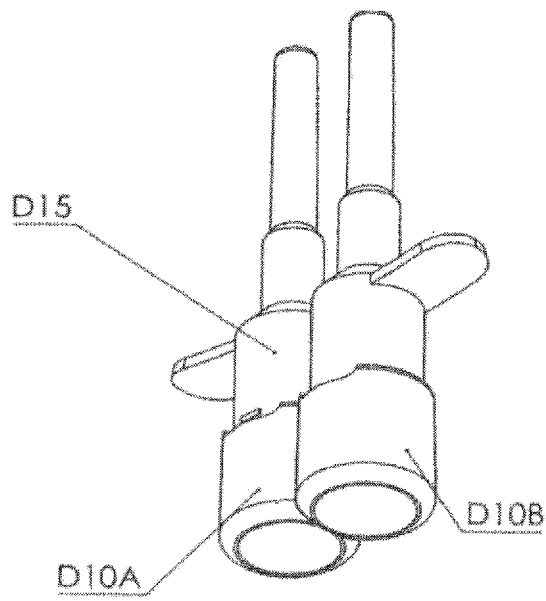
Figure 32B:
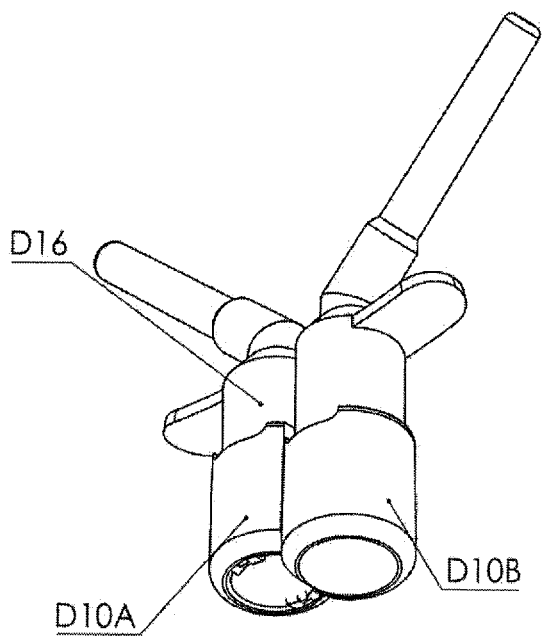
Figure 32C:
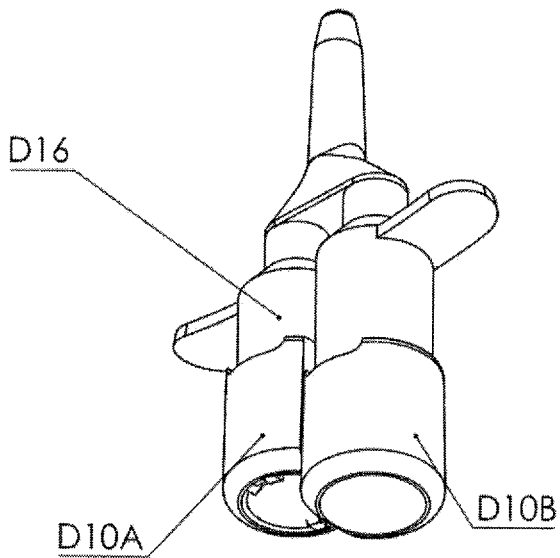
Figures 33A, 33B, 33C:
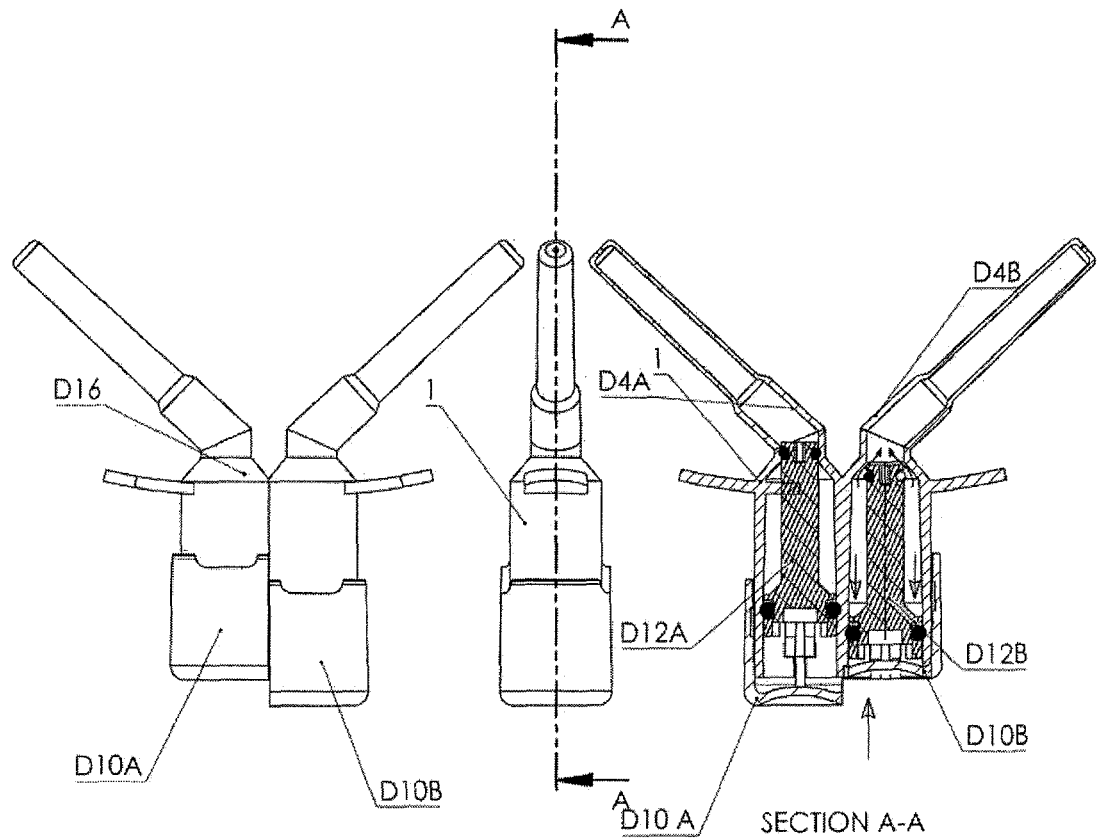
Figure 33D:
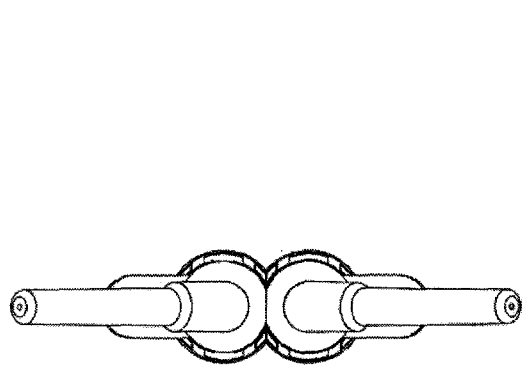
Figure 33E:
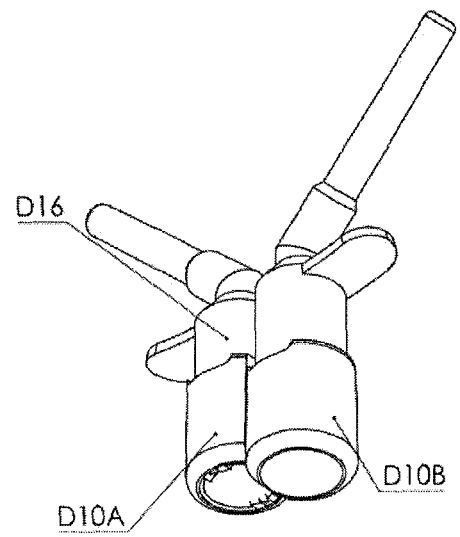

FIG. 32A-C shows embodiments of a devices configured to supply a single dose of a medicament to each of two nostrils. The devices (D15 and D16) of FIGS. 32A and 32B have two independent aerosolization and delivery devices (D10A and D10B), each containing a single dose of a drug, and each of which is in independent fluid communication with a nosepiece. In FIG. 32A, the nosepieces are parallel to each other, whereas in FIG. 32B, the nosepieces are at approximately right angles to each other.

The device (D16) of FIG. 32C, also comprises two independent single-dose aerosolization and delivery devices (D10A and D10B), but both of these are in communication with a single nosepiece.

FIG. 33A-E shows a front view (FIG. 33A), a side view (FIG. 33B), a cross-section view (FIG. 33C) a top view (FIG. 33D), and a perspective view (FIG. 33E) of an embodiment with nose pieces at approximately right angles to each other (FIG. 32B).

The device (D16) comprises two independent aerosolization and delivery devices (D10A and D10B), each in fluid connection with a single nosepiece. Each aerosolization and delivery device (D10A and D10B) comprises a single dose of a drug, which can comprise a single substance or a plurality of substance, stored as a mixture or stored in independent compartments, as disclosed above. The device also comprises activation holders; the aerosolization and delivery devices (D10A and D10B) will be activated one at a time, as disclosed above, with fingers on the activation holders; and a thumb on the activation button at the base of an aerosolization and delivery device (D10A or D10B). It can be seen from FIGS. 34B, and 34D, 34D1 and 34D2 show that the nose pieces of the device (D16) lie substantially in the same plane in this embodiment; in other embodiments, they could lie in different planes.

FIG. 34C is a cross-section through the device, along the line of A-A in FIG. 34B. In FIG. 34C, one aerosolization and delivery device (D10A) has not yet been activated, while the other (D10B) has been activated (large upward arrow). In the non-activated delivery device (D10A), the air chamber gate (D12A) is in the distal position, with the distal end of the air chamber gate (D12A) blocking passage of gas into the mixing chamber (D4A). In the activated delivery device (D10B), the air chamber gate (D12B) has moved proximally (large downward arrows), leaving a gap between the distal end of the air chamber gate (D12B) and the mixing chamber (D4B) which allows passage of gas (small upward arrows) into the mixing chamber (D4B) from whence gas can pass through the nose piece and exit the device.

FIG. 34A-E shows a front view (FIG. 34A), a side view (FIG. 34B), a front view (FIG. 34C), a cross-section view of embodiment with a single nose piece (FIG. 34D1), an enlarged top view (34D2), a top view (FIG. 34E) and a perspective view.

The device (D16) comprises two independent aerosolization and delivery devices (D10A and D10B), and a single nosepiece, with both aerosolization and delivery devices (D10A and D10B) in fluid communication with the single nosepiece. Each aerosolization and delivery device (D10A and D10B) comprises a single dose of a drug, which can comprise a single substance or a plurality of substance, stored as a mixture or stored in independent compartments, as disclosed above. The device also comprises activation holders; the aerosolization and delivery devices (D10A and D10B) will be activated one at a time, as disclosed above, with fingers on the activation holders; and a thumb on the activation button at the base of an aerosolization and delivery device (D10A or D10B).

FIG. 34C is a cross-section through the device, along the line of A-A in FIG. 34B. As shown in FIG. 34C, the single nosepiece comprises two mixing chambers (D4A and D4B), two sets of air passages (D6A and D6B) and two aerosol exits (D7A and D7B) allowing the aerosol to exit from the device. Therefore, although there is only one nose piece, substance from one of the delivery devices (D10A or D410B) will not come into contact, within the device, with substance from the other delivery device.

In FIG. 34C, one aerosolization and delivery device (D10A) has not yet been activated, while the other (D10B) has been activated (large upward arrow). In the non-activated delivery device (D10A), the air chamber gate (D12A) is in the distal position, with the distal end of the air chamber gate (D12A) blocking passage of gas into the mixing chamber (D4A). In the activated delivery device (D10B), the air chamber gate (D12B) has moved proximally (large downward arrows), leaving a gap between the distal end of the air chamber gate (D12B) and the mixing chamber (D4B) which allows passage of gas (small upward arrows) into the mixing chamber (D4B) from whence gas can pass through the nose piece and exit the device.

Figure 2:
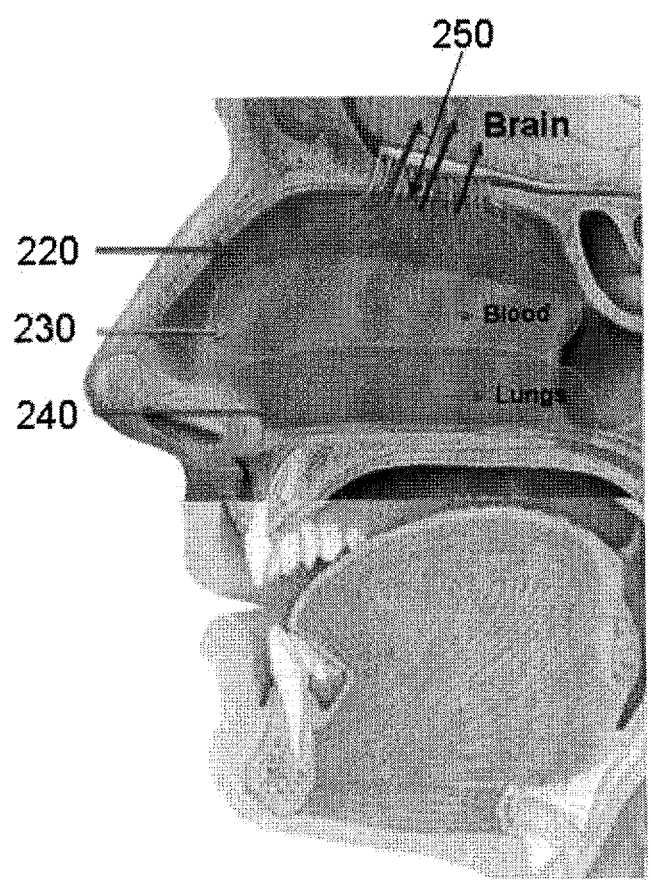
Figure 3:
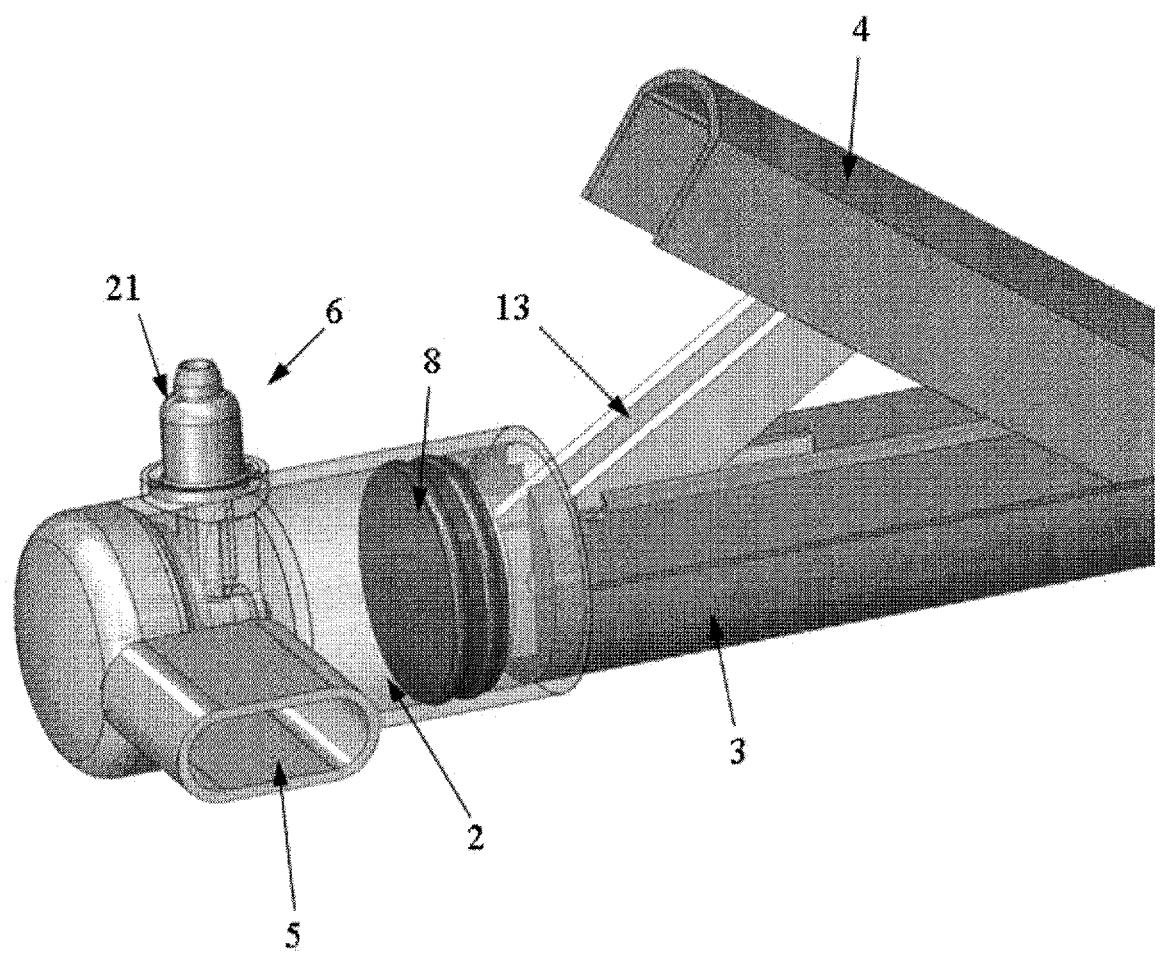

FIG. 34D2 shows a top view of the device. In the enlarged view (FIG. 34D1), the two independent exits (D7A and D7B) can be clearly seen. It should be noted that the embodiments of the device are not limited to the exemplary embodiments shown above.

In embodiments where delivery is to a nostril, delivery of the substance can be improved by inducing sniffing in the user.

Sniffing (short, sharp breaths through the nose, for example, when smelling something) is highly correlated with soft palate (Velum) position. Sniffs are rapidly modulated in an odorant-dependent fashion by a dedicated olfactomotor system, and affect the position of the soft palate at the posterior end of the nasal cavity. When sniffing through the nose, the palate is in its upper position to cause separation between the nasal cavity and the oral cavity.

In addition to conscious control, sniffing may be reflexively elicited by chemicals, functioning as either irritants or odors in the nose. Overall sniff duration and pattern can be modulated in real time to optimize olfactory perception. When the olfactory system encounters a concentrated odorant, sniff vigor is reduced and sniff time is reduced; when it encounters a diluted odorant, sniff vigor is increased and duration lengthened. Odorant pleasantness also affects sniffing; sniff vigor and duration increase when smelling a pleasant odor and decrease when smelling an unpleasant odor.

In preferred embodiments, the device disclosed herein can release odorant into the nasal cavity of the user in order to reflexively elicit sniffing. The odorant can be a single odorant or a mixture of odorants and can comprise compounds from different chemical families, for non-limiting example:

Esters: Geranyl Acetate, Ethyl Acetate, Benzyl Acetate, Octyl Acetate.

Linear Terpens: Geraniol, Citral, Citronella, Nerolidol.

Cyclic Terpens: Terpineol, Thujone.

Aromatic: Eugenol, Vanillin, Anisole, Thymol.

Amines: Indole.

Also aromatic compounds of alcohols, aldehydes, esters, ketones, lactones, and thiols.

In preferred embodiments, the substance is contained within a capsule. The capsule can have a single compartment or it can be multi-compartment. The capsule can contain a broad range of drugs and materials. The aromatic compound can be stored in the nozzle, or the nozzle or a portion thereof can be impregnated with aromatic compound, so as to trigger the closing of the velum when the nozzle tip is being placed in the nasal cavity. The delivery can be for local effect, to the systemic circulation, to the central nerve system (CNS), to the brain, preferably via the olfactory epithelium, to the spinal cord and associated nerves, and any combination thereof.

As described hereinabove, the drugs and materials to be delivered can be, but are not limited to, pharmaceuticals, natural compounds, biologics, hormones, peptides, proteins, viruses, cells, stem cells and any combination thereof.

The stored substance or substances can be stored as a liquid, an aerosol, a powder, a slurry, a suspension, or a gel, if thin enough. The substance or substances can be stored either with or without a carrier; the carrier can be a liquid, a gas or a powder.

The substance as delivered can comprise a powder, a mixture of liquid and powder, a mixture of gas and powder, a mixture of powders, a liquid, a mixture of liquid and gas, a mixture of liquids, a gas, or a mixture of gases.

The stored substance or substances can be packaged to minimize degradation, for example, by packaging it in vacuum or under an inert atmosphere. Preferably, capsules are single-use so that a single, controllable dose can be delivered with each use of the device. Capsules can be placed in the container of the device, or the container can comprise the capsule.

Use of an inert gas for the carrier for delivery of the medication obviates the possibility of interactions between the user and the delivery carrier; allergies to carriers, especially in medications used for chronic illnesses, are a growing problem. Furthermore, the delivery carrier is in contact with the medicament for no more than a few seconds and more commonly for no more than a few milliseconds, thereby minimizing degradation of the medicament due to interactions with the delivery carrier.

Examples of drugs and materials deliverable using the device are given hereinbelow. All examples listed below are exemplary and are not limiting.

Deliverable drugs and materials include: treatments for allergic rhinitis; treatments for osteoporosis; vaccinations and immunizations; sexual dysfunction drugs; treatments for B12 deficiency; smoking cessation; treatment of gynecological problems; treatment of other women's health issues; general anesthetics; local anesthetics; opioid analgesics; agonist-antagonists and antagonists; antitussives; drugs used in the treatment of motor disorders; antiepileptics; drugs used in affective disorders; antipsychotics (neuroleptics); sedative-hypnotics, anxiolytics, and centrally acting muscle relaxants; treatments for anxiety disorders; skeletal muscle relaxants; treatments for Parkinson's disease; treatments for Alzheimer's disease; treatment for pain and anti-migraine treatment.

Medicaments for treatment of allergic rhinitis include: steroids, including corticosteroids, Flonase, Patanase, Beconase, Antihistamine, Astelin, Otrivin™, Livostin, Theramax, Avamys, Lufeel, Sinofresh, Nasonex, Nasocort and Veramyst.

Medicaments for treatment of osteoporosis include: Miacalcin, Fortical and Stadol.

Medicaments for vaccinations and immunizations include: LAVIN, and influenza vaccines including FluMist.

Medicaments for smoking cessation include: NasalFent.

Other medicaments which can be delivered include: calcitonin and parathyroid hormone.

Neurotransmitters and neuromodulators that can be delivered include: acetylcholine (ACH), Anticholinergic drugs, adenosine triphosphate (ATP), aspartate (Asp), beta-amyloid, beta-endorphin, bradykinin, dopamine (DA), L-DOPA, Carbidopa, epinephrine, dynorphins, endomorphins, enkephalins, 5-hydroxytryptamine (5-HT), Sumatriptan, Imitrex, Migranal, Zolmitriptan, Zomig, Gamma-aminobutyric acid (GABA), glutamate (glu), glycine, histamine, leptin, nerve growth factor and other growth factors), norepinephrine, nitric oxide, and Substance P.

General anesthetics which can be delivered include: alfentanil, desflurane, enflurane, etomidate, fentanyl, halothane, isoflurane, ketamine, methohexital, methoxyflurane, midazolam, lorazepam, diazepam morphine, nitrous oxide ($N_2O$), propofol, sevoflurane, Sufentanil, Sublimase, and thiopental.

Local anesthetics which can be delivered include: benzocaine, bupivacaine, cocaine, lidocaine, prilocaine, procaine, ropivacaine, and tetracaine.

Opioid analgesics, agonist-antagonists, and antitussives which can be delivered include: agonists, codeine, diphenoxylate, fentanyl, heroin and other opioids, hydrocodone, 1-alpha-acetyl-methadol, levomethadyl acetate, loperamide, meperidine, methadone, morphine, oxycodone, d-propoxyphene, combinations of opioids plus acetaminophen and asa, and tramadol.

Agonist/antagonists and antagonists which can be delivered include: buprenorphine, butorphanol, nalbuphine, nalorphine, naloxone, naltrexone, nalmefene, pentazocine, codeine, dextromethorphan, and hydrocodone.

Drugs used in the treatment of Parkinson's disease and motor disorders which can be delivered include: amantadine, apomorphin, baclofen, benzodiazepines, benztropine, bromocriptine, carbidopa, cyclobenzaprine, dantrolene, dopamine, entacapone, haloperidol, L-DOPA, pergolide, pramiprexole, ropinerole, selegiline (deprenyl), trihexyphenidyl, rasagiline, azilect, selegiline, ladostigil, rotigotine, neupro, mono amine oxidase inhibitor, and COMT inhibitor.

Antiepileptics which can be delivered include: acetazolamide, carbamazepine, clonazepam, diazepam, ethosuximide, felbamate, gabapentin, Lamotrigine, lorazepam, phenobarbital, phenytoin, primidone, tiagabine, topiramate, valproic acid, Vigabatrin and Midazolam.

Drugs used in affective disorders which can be delivered include: antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate and valproic acid.

Antipsychotics (neuroleptics) which can be delivered include: chlorpromazine (CPZ), clozapine, fluphenazine, haloperidol, olanzapine, quetiapine, risperidone, sertindole, thioridazine, thiothixene and ziprasidone.

Sedative-hypnotics, anxiolytics, and centrally acting muscle relaxants which can be delivered include: alprazolam, chloral hydrate, diphenhydramine, flumazenil, flurazepam, hydroxyzine, lorazepam, oxazepam, phenobarbital, temazepam, triazolam, zaleplon and zolpidem.

Anxiety disorders and skeletal muscle relaxants which can be delivered include: alprazolam, chlorazepate, chlordiazepoxide, diazepam, flumazenil (antagonist), lorazepam, and oxazepam.

Treatments for Alzheimer's disease which can be delivered include: donepezil, galantamine, rivastigmine, Tacrine, Detemir, Novolin, Humulin, Insulin, insulin like hormone, an insulin analog such as NPH Insulin, Lispro, Aspart, Detemir Insulin, Glulisin, Glargin Insulin, Insulin degludec, BDNF, GDNF, MIBG, anti-cancer agents, anti-cancer drugs, dopamine agonist and dopamine antagonist.

Other drugs which can be delivered include: amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, Pentobarbital, neuroprotective compounds, neuroprotective peptides, neuroprotective factors, davunetide, antischizophrenic drugs, anti-depression drugs, comtan, Entacapone, anti ADHD agents, anti ADHD drugs such as Methylphenidrate (ritalin), and anti-autism and anti-autism symptoms drugs.

Other materials that can be delivered include: both purified natural and synthetic biologics, peptides, proteins, antibodies, cells including stem-cells, parts of cells, nanoparticles and microparticles. The nanoparticles and microparticles can comprise drugs; they can be carriers for drugs, cells or parts of cells; and any combination thereof.

In preferred embodiments, the substance comprises permeation enhancers to improve penetration of the active components of the substance through the mucosal membranes.

In some formulations, the formulation can comprise polymeric microparticles comprising at least one active agent and a permeation enhancer, where the active agent is selected from a group consisting of a peptide, a protein, an antibody, nucleic acid, small molecules, cells and any combination thereof.

A great number of penetration enhancers are known in the literature.

One such penetration enhancer is Hyaluronic acid (also referred to as HA or hyaluronan), which is a polysaccharide that occurs naturally in the body. Due to its exceptional water-binding, visco-elastic and biological properties, HA can improve the attributes, such as, but not limited to, the absorption characteristics, of existing formulations and can also add new attributes to existing formulations. Inclusion of HA can be advantageous when developing new formulations.

When used for drug delivery and targeting, HA can provide clear advantages over traditional polymeric substances such as synthetic polymers such as, but not limited to, poly(ethylene glycol), poly(lactic acid), poly(glycolic acid), poly Acrylic Acid and Poly-(N-isopropylacrylamide), or other biopolymers such as chitosan and alginate.

HA's benefits in the drug delivery area include, but are not limited to:
Flexibility when designing controlled drug release profiles;
More stable drug formulations;
Effective drug targeting via accumulation at the targeted site and receptor-mediated uptake;
Enhancement of bioavailability and biocompatibility of drugs; and
Reduction of drug cytotoxicity in healthy tissues polymeric microspheres polymeric controlled release preparation a mucoadhesive agent.

Other penetration enhancers include, but are not limited to the following:

A group containing: a fatty acid, a medium chain glyceride, surfactant, steroidal detergent, an acyl carnitine, Lauroyl-DL-carnitine, an alkanoyl choline, an N-acetylated amino acid, esters, salts, bile salts, sodium salts, nitrogen-containing rings, and derivatives. The enhancer can be an anionic, cationic, zwitterionic, nonionic or combination of both. Anionic can be but not limit to: sodium lauryl sulfate, sodium decyl sulfate, sodium octyl sulfate, N-lauryl sarcosinate, sodium carparate. Cationic can be but not limit to: Cetyltrimethyl ammonium bromide, decyltrimethyl ammonium bromide, benzyldimethyl dodecyl ammonium chloride, myristyltimethyl ammonio chloride, deodecyl pridinium chloride. Zwitterionic can be but not limit to: decyldimethyl ammonio propane sulfonate, palmityldimethyl ammonio propane sulfonate. Fatty acid including but not limit to: butyric, caproic, caprylic, pelargonic, capric, lauric, myristic, palmitic, stearic, arachidic, oleic, linoleic, linolinic acid, their salts, derivatives and any combinations or glyceride, monoglyceride, a diglyceride, or triglyceride of those fatty acids. Bile acids or salts, including conjugated or un conjugated bile acids, such as but not limited to: cholate, deoxycholate, tauro-cholate, glycocholate, taurodexycholate, ursodeoxycholate, tauroursodeoxycholate, chenodeoxycholate and their derivatives and salts and combinations. Permeation enhancer as comprises a metal chelator, such as EDTA, EGTA, a surfactant, such as sodium dodecyl sulfate, polyethylene ethers or esters, polyethylene glycol-12 lauryl ether, salicylate polysorbate 80, nonylphenoxypolyoxyethylene, dioctyl sodium sulfosuccinate, saponin, palmitoyl carnitine, lauroyl-1-carnitine, dodecyl maltoside, acyl carnitines, alkanoyl cjolline and combinations. Other include but not limited, 3-nitrobenzoate, zoonula occulden toxin, fatty acid ester of lactic acid salts, glycyrrhizic acid salt, hydroxyl beta-cyclodextrin, N-acetylated amino acids such as sodium N-[8-(2-hydroxybenzoyl)amino]caprylate and chitosan, salts and derivatives and any combinations.

Other enhancers include: formulations of water in oil, formulations of oil in water; emulsions, double emulsions, micro-emulsions, nano-emulsions, water in oil emulsions, oil in water emulsions; steroidal detergent, and an acylse; to allow better absorption in the mucosal tissue, better permeation and absorption in the target cells, better stability of the encapsulated drug/active ingredient.

Some embodiments comprise, either alone or in combination with a penetration enhancer, a mucoadhesive agent such as, but not limited to, bioadhesive proteins, carbohydrates and mucoadhesive polymers In the capsule of the present invention, the device comprises at least one compartment, and preferably a plurality of compartments, each containing a flowable substance. The delivery device is designed to rupture the compartments such that the flowable substances are mixed with a carrier, preferably air, and delivered to a predetermined deposition site, typically, but not exclusively, in the nasal passages.

Medicaments may be supplied as liquids, as powders, or as aerosols. In the preferred embodiment, the medicament is supplied in a single-dose capsule. In other embodiments, the medicament is supplied in a multi-dose capsule means, the multi-dose capsule configured to provide a single dose per activation.

In preferred embodiments, the flowable-substance capsule has a plurality of compartments. A compartment can contain at least one medicament, at least one medicament precursor, carrier gas, compressed gas, and any combination thereof.

The different compartments can contain different medicaments, with the plurality of medicaments delivered to the nostril or other delivery site in a single dose. In this manner, a plurality of medicaments may be supplied to the nostril in a single injection, with interactions occurring between the medicaments at most during the short time between activation of the device and the delivery of the substances and their deposition at the target site.

In some embodiments, interactions between components are unwanted. In such embodiments, a sequential release will utilize the short time period between release of the components and their absorption in the body to prevent such unwanted interactions and/or reactions.

In other embodiments, mixing and/or reactions are desired. In such embodiments, the reactions can occur all at once, by rupturing all of the compartments at the same time and mixing/interacting the components, either in the aerosol or in at least one mixing chamber. In other embodiments, a component can be added by needle insertion at a desired time before use, either into an empty compartment or into an occupied compartment (so that a desired reaction can occur). In other embodiments, the compartment walls rupture in a predetermined order, so that mixing/interaction occurs in stages, in a predetermined order. Mixing/interaction can occur in a compartment or compartments, in a mixing chamber, in the air passages of the device, in the aerosol, in the nasal (or other) passages of the body, and any combination thereof.

As a non-limiting example, a medicament can comprise four components, stored in four compartments of a capsule. Prior to activation, a fifth component is injected into compartment 1. After a predetermined time, the device is activated and the walls between compartment 1 and compartment 2 are broken, allowing mixing of 5/1 and 2. This followed by rupture of the walls surrounding component 3, which then mixes with 5/1/2 and reacts with 2. The last walls to rupture are those surrounding compartment 4; material 4 remains in a separate part of the aerosol and deposits on the nasal passages after deposition of 5/1/2/3.

In another example, precursor A mixes with precursor B to form intermediate C, and, subsequently, intermediate C mixes with precursor D to form final product E.

Mixing or reactions or release of components from different compartments can occur simultaneously, in different linked compartments, or they can occur sequentially, as in the example above. Any combination of sequential and simultaneous reactions and/or mixing and/or release can be used. Components can arrive at the deposition site simultaneously, either mixed or unmixed, sequentially, and any combination thereof.

It should be noted that there can be a predetermined delay of some fractions of a second between rupturing of walls of different compartments, in order to, for non-limiting example, allow complete mixing of one set of components or allow a reaction between one set of components to go to completion before the next mixing/reaction starts or the delivery starts.

In some embodiments, the device or, preferably, the capsule, comprises a mixing mechanism or mixing chamber, so that, as described above, components of the composition can mix and/or react during the activation process, enabling components to be stored separately and/or to be stored as stable precursors, but to deliver a predetermined treatment comprising at least one medicament to a predetermined delivery site.

In preferred embodiments of the device, the mixture of aerosol and pre-aerosolized mist is formed within the nozzle, with the hole at the lateral end of the nozzle having little effect on either the shape of the dispersion plume or the velocity of the aerosol.

Figures 35, 36:
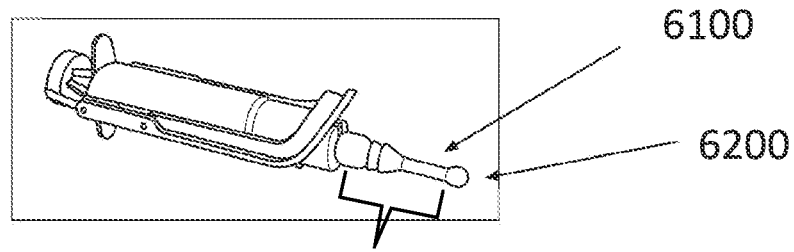

An experimental setup to demonstrate the location of formation of the mist is shown in FIG. 35, and the results of tests for three different operating conditions (1, 2 and 3) are shown in Table 1 and FIG. 36.

TABLE 1

Location of Aerosol Formation

| Test | Air Volume (ml) | Pressure (bar) | Orifice Diameter (mm) | Aerosol produced Before Exit from Device? |
|---|---|---|---|---|
| 1 | 19 | 6 | 0.8 | Yes |
| 2 | 8 | 4 | 0.8 | Yes |
| 3 | 8 | 6 | 0.8 | Yes |

FIG. 35 shows an embodiment of the device, with the nozzle (6100) and the nozzle tip (6200) on the right, with the bracket indicating the region shown enlarged (6190) in FIG. 36.

Representation before activation is shown in the center of FIG. 36, and representation during activation is shown on the right. Before activation, the nozzle is clear; there is no aerosol therein. After activation, the nozzle appears opaque due to the aerosol and/or pre-aerosolized mist therein. If no aerosol or pre-aerosolized mist had been formed, the liquid would exit as a thin stream, which would appear in the image as a streak down the center of the nozzle.

Droplet Distribution for Travel Down a Tube

In all known other mechanisms of creating aerosols, an orifice is placed at the end of a nozzle and the inner diameter of the device's nozzle and, especially, its orifice, is the main parameter that influences aerosol formation and the aerosol's characteristics. In contrast, in the present invention, no orifice is needed. More than that, putting a conventional orifice at the end of the nozzle will actually limit the forces reaching the liquid or powder being dispensed, and thus will-reduce the ability to create the desired fine aerosol at the target site. Thus, the large diameter tubing that can be used in the present invention, about an order of magnitude larger than the diameter of commonly-used tubes and orifices, results in the desired fine aerosol, carried efficiently into the nasal cavity with droplet median diameters (DV50) on the order of 1-100 micrometer.

In the present invention, the aerosol is created as a result of the air volume-pressure parameters of the device and is influenced by the nasal cavity resistance rather than primarily by the orifice diameter.

In order to model nasal friction and air resistance and as a model for aerosol formation in the nasal cavity, a 36 cm long glass tube with an inner diameter of 2 cm, filled with oil up to 22 cm of its length, was used.

Theoretical analysis has indicated that 5 cm of tube is equivalent to about 0.1-0.5 cm of the nasal passages; therefore the 22 cm. tube would approximately simulate the full depth of a nasal passage.

The test material was 200 microliter of Methylene Blue liquid solution.

The liquid solution was discharged from a device into the base of the tube and pictures and videos were taken in order to be able to follow the process of aerosol formation. The length of the deposition region, the aerosol distribution and the diameter of the aerosol droplets were determined as a function of time.

FIGS. 37A-D show the effect of orifice size on droplet size (FIGS. 37B, 37D) and droplet distribution (FIGS. 37A, 37C) in a conventional device.

The Methylene blue solution was injected into the tube using a syringe. FIGS. 37A-B show droplet distribution and size for a larger needle (21 G; approx. 0.5 mm) and FIGS. 37C-D show droplet distribution and size for a smaller needle (25 G; approx. 0.2 mm). The larger diameter needle (FIGS. 37A-B) creates larger droplets than the smaller diameter needle (FIGS. 37C-D).

In contrast, FIGS. 38A1-D and 39A-D show that the opposite is true if the technique of the present invention is used, where the aerosol is created by means of a pressurized gas.

In reference to FIGS. 38A1-D show the effect of orifice size on droplet size (FIGS. 38B, 38D) and droplet distribution (FIGS. 38A1, 38A2, 38C) in a device of the present invention. FIG. 38A1 shows the distribution in the lower part of the tube, while FIG. 38A2 shows the distribution in the upper part of the tube.

In FIGS. 38A1-D, the device of the present invention is charged to 7 barg pressure and 20 ml of Methylene Blue solution is discharged through an orifice into the base of the tube. FIGS. 38A1-B show droplet distribution and size for a larger needle (21 G; approx. 0.5 mm) and FIGS. 38C-D show droplet distribution and size for a smaller needle (25 G; approx. 0.2 mm). In this case, the larger nozzle (FIGS. 38A1-B) has smaller diameter droplets, a more homogeneous aerosol and a distribution that extends much further up the tube than the smaller diameter nozzle (FIGS. 38C, 38D).

In reference to FIGS. 39A-D show the effect of orifice size on droplet size (FIGS. 39B, 39D) and droplet distribution (FIGS. 39A, 39C) in a device of the present invention.

Figure 39A:
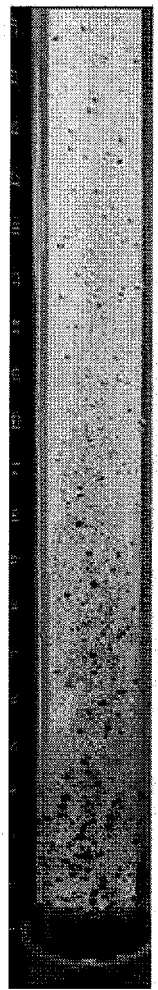
Figure 39B:
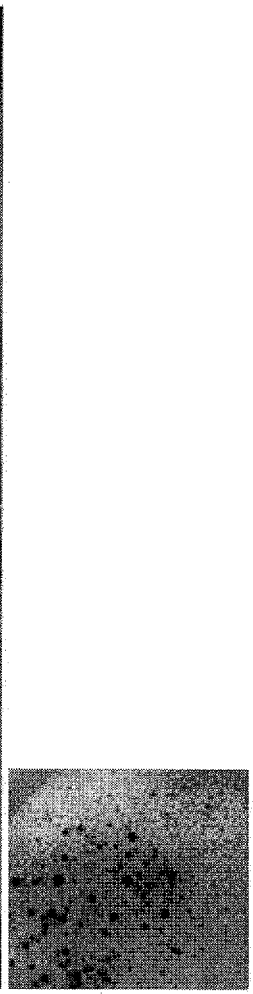
Figure 39C:
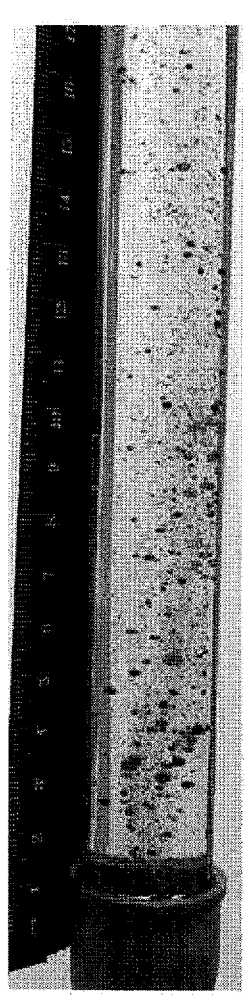
Figure 39D:
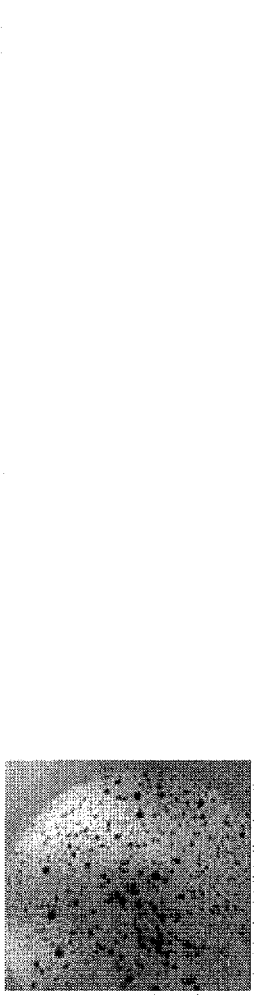

In FIGS. 39A-D, the device of the present invention is charged to 4 barg pressure and 18 ml of Methylene Blue solution is discharged through an orifice into the base of the tube. FIGS. 39A-B show droplet distribution and size for a larger needle (21 G; approx. 0.5 mm) and FIGS. 39C-D show droplet distribution and size for a smaller needle (25 G; approx. 0.2 mm). In this case, the larger nozzle (FIGS. 39A, 39B) has smaller diameter droplets and a more homogeneous aerosol than the smaller diameter nozzle (FIGS. 39C, 39D).

A comparison of FIGS. 38A1-D and 39A-D show that the higher volume-higher pressure combination (20 ml, 7 barg) has smaller diameter droplets with a greater homogeneity and a distribution that extends much further up the tube than the lower volume-lower pressure combination (18 cc, 4 barg).

Figures 41A, 41B, 41C:
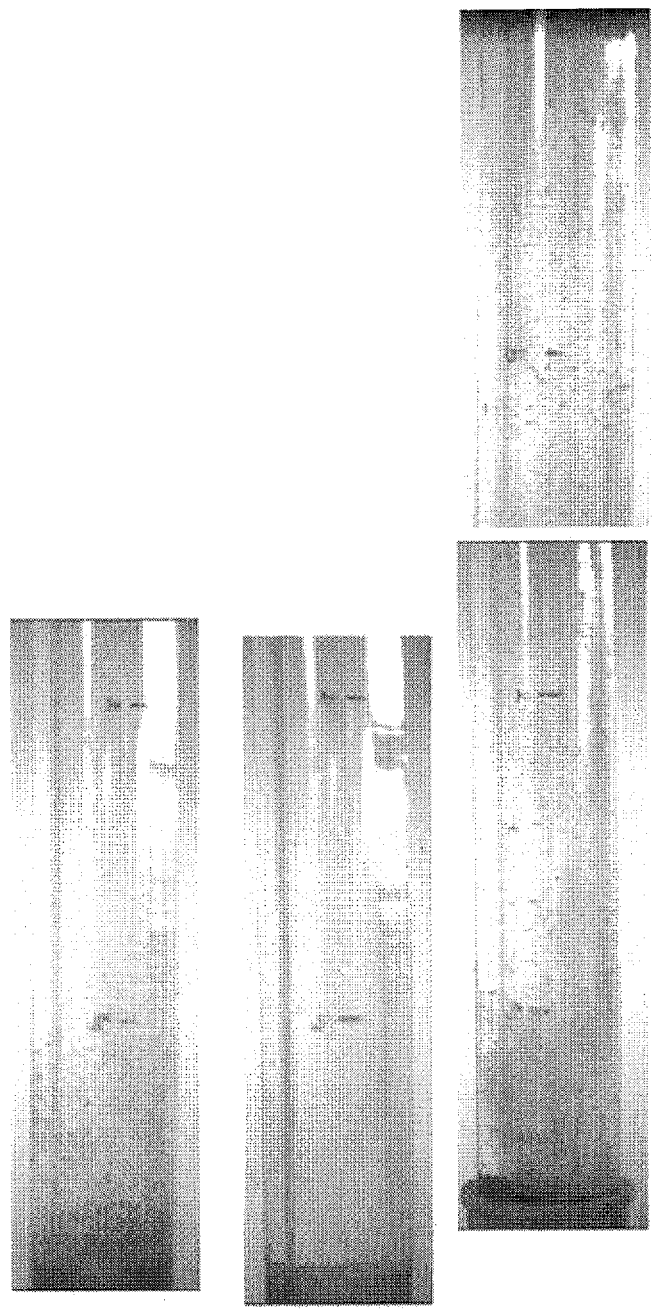

In FIGS. 40A-C and 41A-C, a comparison is made between 2 commercial, prior art devices and the present invention device. In all cases, 0.1 ml of aqueous solution was tested. In FIGS. 40A and C and 41A and C, the liquid was Methylene Blue in aqueous solution; in FIGS. 40B and 41B, saline solution alone was used. The liquid was discharged from the device into the base of a tube filled with oil. In FIGS. 40A and 41A, the Otrivin™ device was use, in FIGS. 40B and 41B, the Otrimer™ device was used, and in FIGS. 40C and 4C, the present invention technology was used. For both the Otrivin™ (FIG. 40A) and the Otrimer™ (FIG. 40B) devices, the height reached by the solution at the time of application is less than 10 cm and the liquid forms a distinct bolus near the bottom of the tube. In contrast, with the device demonstrates the present invention (FIG. 40C), the liquid appears in the tube as small droplets, with some of the droplets reaching a height in the tube of 20 cm.

Two minutes later, (FIGS. 41A-C), the liquid from the Otrivin™ device has reached a height of about 5 cm (FIG. 41A), while the liquid in from the Otrimer™ device has fallen to the base of the tube; it is barely visible at the bottom of the tube in FIG. 41B. In contrast, the droplets are fairly stable in the tube in the present invention technique (FIG. 41C); there is a fairly even distribution of droplets until a height of about 12 cm is reached, and some of the droplets have reached a height of nearly 20 cm.

Figures 42A, 42B, 42C, 42D, 42E:
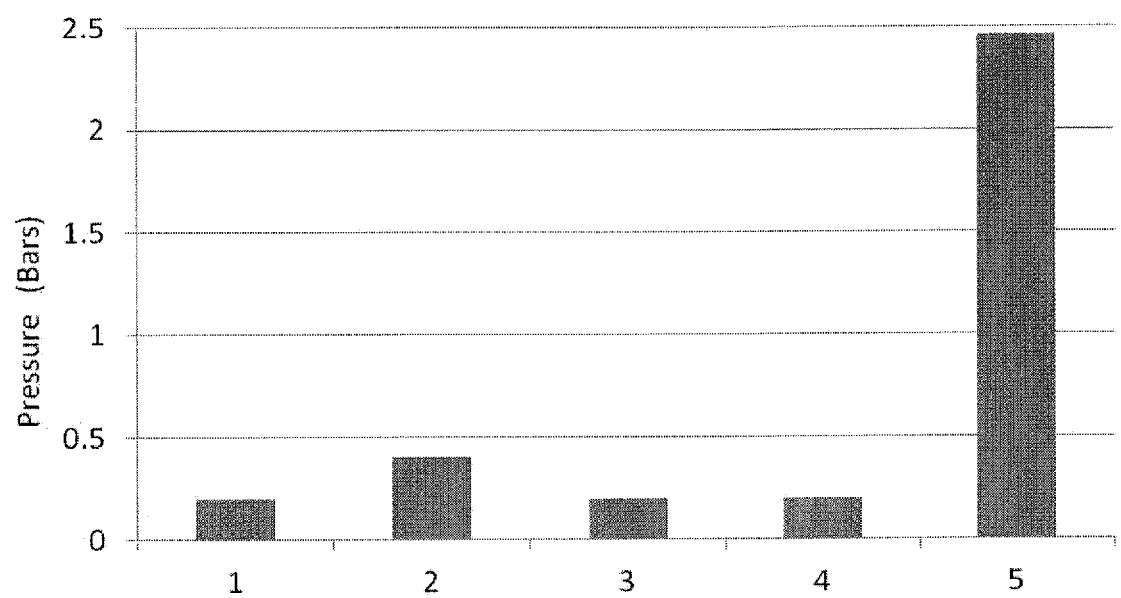

In reference to FIGS. 42A-E, nasal applicators were connected to a ~7 ml volume closed tubing, with a connection to a pressure sensor. The ~7 ml volume represents the approximate volume of the nasal cavity. The devices were discharged into the closed tubing and the maximum pressure developed in the tubing was measures. The pressure in the tubing for the four commercial devices, the Otrivin™ device (FIG. 42A), the Marimer device (FIG. 42B), the Rhinox device (FIG. 42C), and the Alrin™ device (FIG. 42D) were less than 1 barg. In contrast, the pressure in the tubing from the present invention technology (FIG. 42E), was almost 2.5 barg, more, than 2½ times as much as the closest commercial device, the Marimer device (FIG. 42B).

In reference to FIGS. 43A-C, Methylene Blue in aqueous solution was delivered through a nostril of a human nasal cast model (FIG. 43A) filled with oil to mimic the nasal cavity's inner pressure and conditions. The dashed circles (10200) show the exit from the top of the nasal cast; material that reaches the exit would reach the olfactory epithelium in the nose. FIGS. 43B and C show nasal cast models after application of the Otrivin™ device (FIG. 43B) and the present invention technology based device (FIG. 43C) to a nostril of the nasal cast. As can be seen from FIG. 43B, no material would reach the olfactory epithelium with the Otrivin® device—no material has reached the exit from the nasal cast. In contrast, droplets of material (dotted circle, 10210) have exited the nasal cast, showing that, unlike the commercial devices, the material discharged from the present invention technology based device is capable of reaching the olfactory epithelium.

Plume Angle

In contrast to prior-art nasal delivery devices and technologies, the devices of the present invention can produce a fine aerosol in the nasal cavity or other desired body orifice at the target area and at the location of the target tissue instead of immediately after exit from the device. Utilizing the pressure as a driving force and the air as a carrier allows the material to be released from the nozzle as a combination of material in a pre-aerosolized state and an aerosol. The properties of the resultant aerosol are typically dependent on the properties of the device and of the medium into which the aerosol is discharged. The properties of the device which affect the aerosol characteristics are the delivery speed, the volume of the delivery gas, and the characteristics of the delivery orifice.

In some embodiments, the aerosol properties are fairly independent of the delivered substance, in other embodiments, the pressure, volume, orifice characteristics and delivered substance properties can be co-optimized.

In prior-art devices the aerosol is produced at the exit to the device. Typically, the aerosol comprises a wide dispersion of particle sizes, a wide "fan" of aerosol and a low driving force. Therefore, the large droplets typically deposit very close to the exit from the device; smaller droplets tend to quickly contact the walls of the passage, so that deposition is typically predominantly close to the exit from the device, with little of the substance reaching desired sites deeper in the orifice, such as the turbinates of the nose.

In contrast, in the present device, the aerosol and pre-aerosolized mixture of gas and substance exits the device with a significant driving force, when the preaerosolized fluid hits the walls of the nasal passages, it "explodes" into a fine aerosol that is capable of being driven by the pressure deep into the nasal passages to deposit in the desired region.

In reference to FIGS. 45A-C, a schematic is shown of a nozzle and the aerosol it releases. The orifice emits an aerosol which forms a conical plume (1) with a distribution of particles (2) in it.

The plume angle is the total angle subtended by the plume, as shown by the angle $\alpha$ in FIGS. 45A-C and by the angle $\theta$ subtended between the lines, as shown in FIG. 44A.

In FIG. 45A-C, the plume angle $\theta$ is compared for 2 commercial nasal delivery devices (FIGS. 45A-B) and the SipNose device (FIG. 45C). Aerosol was measured at room temperature. The widths of the plumes were measured at the same distance (3 cm) from the discharge site in each device.

The SipNose device has a much narrower plume than the two commercial devices. The plume angles for the commercial devices, the AIrin™ from Teva (FIG. 45A) had a plume angle of 35°, the LMA MAD Nasal™ (FIG. 45B) had a plume angle of 27°, while the plume angle for the SipNose device (FIG. 45C) had a plume angle of only 8.7°.

All the above parameters allow the aerosol to better deposit in the area of interest such as the area of the olfactory epithelium in the nasal cavity; and to be better absorbed by the target tissue such as the brain.

Plume Intensity

FIGS. 46A-B compares the amount of material reaching the upper layers of the nasal model for one of the prior-art devices (commercial 2—LMA MAD Nasal™) and the device of the present invention (SipNose). In each case, 100 μl of liquid aerosol was discharged into a human nasal model (a nasal cast). The upper layer of the nasal cast was removed in order to observe the amount and characteristics of the aerosol that reaches the area of the upper portion of the nasal cavity. It is clear that there is a better distribution of the substance in the area of interest, the uppermost portions of the nasal cavities when the present invention technology is in use (FIG. 21B).

TABLE 2

Plume Characteristics for the SipNose device

| Pressure (Bar) | Gas Volume $V_{gas}$ (ml) | Substance Volume $V_{sub}$ (ul) | Angle (°) | Height at 3 cm (mm) | Height at 6 cm (mm) | Velocity (m/s) |
|---|---|---|---|---|---|---|
| 2 | 8 | 500 | 15 | 10 | 16 | 23 |
| 6 | 8 | 500 | 20 | 12 | 18 | 15.8 |
| 6 | 19 | 100 | 15 | 10 | 21 | |
| 6 | 19 | 500 | 20 | 11 | 18 | |
| 2 | 5 | 100 | 9 | 10 | 12 | |
| 2 | 10 | 100 | 15 | 8 | 15 | |
| 2 | 5 | 500 | 17 | 18 | 20 | |
| 2 | 10 | 500 | 16 | 11 | 17 | 11.9 |
| 6 | 12 | 100 | 12 | 9 | 18 | |
| 6 | 6 | 500 | 12 | 5 | 6 | |
| 6 | 12 | 500 | 16 | 8 | 13 | |

TABLE 3

Plume Characteristics for the commercial devices

| Device | Pressure (Bar) | Gas Volume $V_{gas}$ (ml) | Substance Volume $V_{sub}$ (ul) | Angle (°) | Height at 3 cm (mm) | Height at 6 cm (mm) | Velocity (m/s) |
|---|---|---|---|---|---|---|---|
| MAD Nasal ™; | — | 6 | 100 | 35 | 18 | 30 | 2.3 |
| Wolfe Tory | — | 18 | 100 | 55 | 30 | 40 | |
| | — | 0 | 500 | 55 | 38 | 55 | |
| | — | 3 | 500 | 35 | 25 | 30 | |
| | — | 6 | 500 | 35 | 21 | 35 | 2.3 |
| | — | 18 | 500 | 33 | 20 | 29 | |
| Simply Saline Nasal Mist; Church & Dwight Co., Inc. | 7 | — | 500 | 45 | 37 | 53 | |
| Otrimer; Novartis | 7 | — | 500 | 35 | 20 | 33 | |
| Alrin, Teva | — | 0 | 100 | 35 | 26 | 33 | 3.3 |

FIG. 47 shows an experimental setup for determining coverage of a spray plume. A device (3510) is at the left, and a screen for measuring coverage is at the right (3520). The distance between device and screen is about 25 cm.

FIGS. 48A-J show examples of spray coverage for different devices. FIGS. 48A-D show coverage and droplet distribution for the SipNose device for different device parameters, while FIGS. 48E-J show, coverage and droplet distribution for a number of different commercial devices.

In all cases, the SipNose device produces a spray pattern covering a well-defined area of the screen. A large number of particles reach the screen and, in the coverage area, this is significantly more than for any of the commercial devices.

Commercial devices F and J are the best of the prior-art devices, with a reasonable amount of the aerosol reaching the screen, but the distribution is very much wider than for the SipNose device, covering virtually the entire screen. Commercial devices H and I are the worst of the prior-art devices, with very little of the aerosol even reaching as far as the screen.

Tables 2 and 3 show plume characteristics for the SipNose device for different operating parameters and an orifice size of 0.8 mm (Table 11) and for four commercial devices (Table 12).

Significant differences were seen between the properties of the plumes between the SipNose device and the commercial devices; small, if any, overlap was seen between the plume angles, the plume heights or the plume velocities. For the SipNose devices, the range of plume angles was 5° to 25°, the range of plume heights 3 cm from the device was 1 to 20 mm, the range of plume heights 6 cm from the device was 5 mm to 25 mm and the range of plume velocities was 5 m/s to 50 m/s. For the commercial devices, the plume angles were over 33°, the plume heights 3 cm from the device were over 18 mm, the plume heights 6 cm from the device were over 29 mm and the plume velocities were less than 5 m/s.

An example of the droplet size distribution is given in FIG. 49, which shows a plot of the number of particles vs. particle size, with the X axis (particle size) being logarithmic. The distribution is asymmetrical, having a long "tail" on the large-diameter side. The largest droplets are on the order of 900 m, with the smallest particles being on the order of a 2-5 μm. The DV50 diameter is about 75 μm.

Tables 4 and 5 show droplet size distributions averaged over 10 repeats for 100 ul and 400 ul saline in two SipNose devices (23-11 for 100 ul and 23-12 for 400 ul) for parameters 6 barg pressure, 19 ml of gas, and 0.8 mm orifice diameter. In all cases shown, low variability was seen for the 10 repeats of the measurements.

TABLE 4

Device 23-11

| Device Version | D v (0, 0.5) (μm) | Obscuration (%) |
|---|---|---|
| 23-11 | 73.0 | 1.3 |
| 23-11 | 70.6 | 1.5 |
| 23-11 | 78.8 | 0.9 |
| 23-11 | 86.6 | 1.2 |
| 23-11 | 74.2 | 1.3 |
| 23-11 | 88.7 | 1.0 |
| 23-11 | 64.9 | 1.2 |
| 23-11 | 86.7 | 1.3 |
| 23-11 | 55.3 | 1.2 |
| 23-11 | 58.3 | 1.1 |
| Mean | 73.7 ± 11.8 | |

TABLE 5

Device 23-12

| Device Version | D v (0, 0.5) (μm) | Obscuration (%) |
|---|---|---|
| 23-12 | 68.7 | 3.8 |
| 23-12 | 83.5 | 2.4 |
| 23-12 | 81.7 | 4.8 |
| 23-12 | 71.4 | 22.9* |
| 23-12 | 92.1 | 3.3 |
| 23-12 | 83.8 | 4.3 |
| 23-12 | 83.3 | 5.3 |
| 23-12 | 100.6 | 3.4 |
| 23-12 | 100.8 | 2.8 |
| 23-12 | 92.3 | 6.4 |
| 23-12 | 108.6 | 3.4 |
| Mean | 88.3 ± 12.9 | |

*anomalous value

Table 6 shows an example of the reproducibility for the SipNose device. The measurements were done by weighing, and part of the variability shown probably depends on the measurement technique.

TABLE 6

Reproducibility for a SipNose device

| | Amount loaded (gm) | Residual amount (gm) | Released (%) | Residual volume (%) |
|---|---|---|---|---|
| 1 | 0.3996 | 0.0584 | 85.4 | 14.6 |
| 2 | 0.4058 | 0.0414 | 89.8 | 10.2 |
| 3 | 0.3915 | 0.0054 | 98.6 | 1.4 |
| 4 | 0.4143 | 0.0063 | 98.5 | 1.5 |
| 5 | 0.3772 | 0.0069 | 98.2 | 1.8 |
| 6 | 0.3902 | 0.0509 | 87.0 | 13.0 |
| 7 | 0.4010 | 0.0626 | 84.4 | 15.6 |
| 8 | 0.3853 | 0.0490 | 87.3 | 12.7 |
| 9 | 0.4302 | 0.0511 | 88.1 | 11.9 |
| 10 | 0.4052 | 0.0482 | 88.1 | 11.9 |
| Average | 0.4000 | 0.0380 | 90.5 | 9.5 |
| Std. Dev. | 0.0152 | 0.0227 | 5.6 | 5.6 |

SipNose aerosol droplets have a mean diameter in the typical range of other nasal delivery devices, and even smaller.

Although the droplets have a small diameter, the width of the aerosol plume is very narrow, and this allows the aerosol to be better distributed in the inner part of the nasal cavity, without depositing at the front of a cavity such as the nasal cavity.

The SipNose device shows high consistency

Penetration Through Fabric

For a distance between nozzle and target of 30 cm, dispensing 100 μl a liquid in a carrier volume, the penetration of the aerosol through 4 mm of a fabric medium was compared for different operating conditions for the SipNose device and three commercial devices, the Alrin, the MAD Nasal from Wolfe Tory and the Otrivin devices. In all cases, the aerosol from the SipNose device penetrated the 4 mm of fabric (FIGS. 50A-E and Table 7).

TABLE 7

| Spread on absorbing surface | | | | | | | |
|---|---|---|---|---|---|---|---|
| | | | Spread | | | | |
| | | Carrier | Diameter | | Area | | |
| | Pressure (barg) | Volume (ml) | Inner (cm) | Outer (cm) | Inner ($cm^2$) | Outer ($cm^2$) | Penetration? |
| SipNose | | | | | | | |
| 1 | 5.6 | 18 | 2.5 | 6 | 4.9 | 28.3 | YES |
| 2 | 4 | 8 | 2 | 6.5 | 3.1 | 33.2 | YES |
| 3 | 6 | 8 | 3 | 5 | 7.1 | 19.6 | YES |
| Commercial | | | | | | | |
| Alrin ™ nasal pump | — | — | — | 15 | — | 177 | NO |
| MAD Nasal | — | — | 8 | 12 | 50.2 | 113 | NO |
| Otrivin ™ nasal pump | — | — | — | 23 | — | 415 | NO |

FIGS. 50A-C shows that, for the three typical operating conditions, significant amounts of the material penetrate through the 4 mm of fabric, consistent with what was seen for the nasal cast example (FIG. 43).

FIGS. 50D-E also show the inner area (dashed circle) delineating the area of heavier deposition and the outer area (solid circle) delineating the area of lighter deposition. For the two commercial devices, the MAD Nasal from Wolfe Tory (FIG. 25D) and the Alrin (FIG. 25E), deposition is light across the entire area, and the edges of the deposition region are not well defined.

The invention claimed is:

1. A device for delivering a predetermined volume $V_{sub}$ [ml] of at least one substance, within at least one body cavity of a subject, said device comprising:
  a) at least one predefined delivery end structured to contain said predetermined volume $V_{sub}$ [ml] of said at least one substance, said at least one delivery end being configured for placement in proximity to said at least one body cavity and said at least one delivery end comprising at least one orifice of diameter D [mm];
  b) a fluid-tight chamber configured to contain a predetermined volume, $V_{gas}$ [ml], of pressurized gas at a predetermined pressure, $P_{gas}$ [barg], said fluid-tight chamber being in fluid communication with said at least one delivery end upon activation of the device, said fluid-tight chamber comprising at least one seal adapted to seal said predetermined volume $V_{gas}$ of said pressurized gas to prevent leakage of said pressurized gas from said fluid-tight chamber;
  c) at least one valve mechanically connectable to said chamber, having at least two configurations:
    (i) an active configuration in which said at least one valve enables delivery of predetermined volume $V_{sub}$ [ml] of said at least one substance from said at least one delivery end to said at least one body cavity via said at least one delivery end; and
    (ii) an inactive configuration, in which said at least one valve prevents delivery of said predetermined volume $V_{sub}$ [ml] of said at least one substance from said at least one delivery end to said at least one body cavity;
  wherein said at least one valve is reconfigurable from said inactive configuration to said active configuration, and vice versa, within a predetermined period of time, dT, in response to activation of said at least one valve;
  wherein said pressurized gas, responsive to said at least one valve being reconfigured from said inactive configuration to said active configuration, is caused to exit said fluid-tight chamber and enter said at least one delivery end and to entrain said at least one substance and deliver said at least one substance via said at least one orifice in said at least one delivery end within said at least one body cavity in the form of an aerosol;
  wherein said device is configured to deliver said predetermined volume $V_{sub}$ [ml] of said at least one substance and said predetermined volume $V_{gas}$ of said pressurized gas through said at least one orifice of diameter D [mm] to said at least one body cavity;
    wherein said at least one delivery end is configured to accommodate said predetermined volume $V_{sub}$ [ml] of said at least one substance and said predetermined volume $V_{gas}$ of said pressurized gas after said at least one valve is reconfigured to said active configuration and said predetermined volume $V_{gas}$ of said pressurized gas exits said chamber and enter said at least one delivery end; and
  wherein said at least one valve comprises a plunger accommodated within said fluid-tight chamber, said plunger being interconnected with said at least one seal, wherein said at least one valve is reconfigured from said inactive configuration to said active configuration by linearly moving said plunger such that a seal of said chamber formed by said at least one seal is removed to allow said $V_{gas}$ [ml] of said pressurized gas to enter said at least one delivery end and entrain said predetermined volume $V_{sub}$ [ml] of said at least one substance to be delivered to said at least one body cavity.

2. The device of claim 1, wherein at least one of the following is satisfied:
  a) said device is configured for a plurality of deliveries of said predetermined volume $V_{sub}$, said predetermined volume $V_{sub}$ being controllably alterable;
  b) said at least one body cavity is a nasal cavity, the mouth, the throat, an ear, the vagina, the rectum, the urethra, and any combination thereof;
  c) viscosity η of said at least one substance is in a range of about $1\times10^{-3}$ poise to about 1 poise;
  d) a median particle size distribution, DV50, of a diameter of particles of said at least one substance, after exit from said device, is less than about 100 μm;
  e) a particle diameter larger than 90% of particles of said at least one substance, DV90, is less than about 1000 μm;
  f) a full width of a plume of aerosol comprising said at least one substance and said gas subtends an angle θ of less than about 25°;
  g) particles in said plume have velocities in a range of about 5 m/s to 50 m/s;
  h) said pressurized gas comprises air, nitrogen, oxygen, carbon dioxide, helium, neon, xenon and any combination thereof;
  i) during dispensing of said at least one substance, a mixture of said predetermined volume $V_{gas}$ [ml] of said pressurized gas with said predetermined volume $V_{sub}$ [ml] of said at least one substance entrained within it forms a plume of aerosol; said aerosol having a predetermined distribution, said distribution being either homogeneous or heterogeneous, said heterogeneous distribution is selected from a group consisting of: an arbitrary distribution, a distribution in which the density of said at least one substance within said mixture follows a predetermined pattern, and any combination thereof; characteristics of said aerosol selected from a group consisting of: particle size, particle shape, particle distribution, and any combination thereof, are determinable from characteristics of said device selected from a group consisting of: said predetermined volume of said pressurized gas, said predetermined volume of said at least one substance, said predetermined pressure of said pressurized gas, said predetermined orifice size, and any combination thereof;
  j) said at least one substance is selected from a group consisting of a gas, a liquid, a powder, an aerosol, a slurry, a gel, a suspension and any combination thereof;
  k) said at least one substance is stored under either an inert atmosphere or under vacuum to prevent reactions during storage;
  l) a dose-response curve is substantially linear for brain concentration of said at least one substance when administered nasally via said device; and
  m) a dose-response curve for brain concentration having a fit selected from a group consisting of logarithmic, parabolic, exponential, sigmoid, power-low, and any combination thereof; of said at least one substance when administered nasally via said device.

3. The device of claim 1, wherein said at least one delivery end has a main longitudinal axis, said at least one delivery end comprises a number n of compartments, said at least one delivery end configured to contain said predetermined volume $V_{sub}$ [ml] of said at least one substance, said volume $V_{sub}$ [ml] of said at least one substance containable in at least one of said n compartments; at least one of the following being satisfied:
   a) the number n of said compartments is an integer greater than or equal to 1; at least one said compartment has cross-section with shape selected from a group consisting of: wedge shaped, circular, oval, elliptical, polygonal, annular, and any combination thereof;
   b) for said number n of compartments being an integer greater than 1, at least two said compartments have different volumes;
   c) for said number n of compartments being an integer greater than 1, at least two said compartments have the same volume;
   d) for said number n of compartments being an integer greater than 1, at least two said compartments have different cross-sectional areas;
   e) for said number n of compartments being an integer greater than 1, at least two said compartments have the same cross-sectional area;
   f) for said number n of compartments being an integer greater than 1, at least two said compartments contain different substances;
   g) for said number n of compartments being an integer greater than 1, at least two said compartments contain the same substance;
   h) for said number n of compartments being an integer greater than 1, at least two said compartments are disposed coaxially around said main longitudinal axis of said at least one delivery end;
   i) for said number n of compartments being an integer greater than 1, at least two said compartments are disposed sequentially along said main longitudinal axis of said at least one delivery end;
   j) for said number n of compartments greater than 1, a plurality of said one or more substances mix during dispensing of said plurality of substances; and
   k) for said number n of compartments greater than 1, said plurality of substances react during said dispensing.

4. The device of claim 1, wherein said at least one delivery end comprises an injection port fluidly connectable to an exterior of said device, said injection port configured such that said at least one substance is insertable into a dispensing chamber of said at least one delivery end via said injection port.

5. The device of claim 4, wherein said device comprises a port cover configured to provide an openable and closable air-tight closure for said injection port, said port cover slidable along said device, rotatable around said device, rotatable around a hinge on the exterior of said device or any combination thereof.

6. The device of claim 1, wherein said at least one delivery end comprises at least one separator configured to subdivide each said at least one delivery end into at least two compartments.

7. The device of claim 1, further comprising at least one separator selected from a group consisting of at least two balls, at least one plunger, at least one thin sheet, at least one frangible membrane, at least one duckbill valve, at least one bendable membrane, at least one temperature dependent membrane, at least one pressure dependent membrane, and any combination thereof.

8. The device of claim 1, wherein said at least one orifice is disposed in at least one position selected from a group consisting of (a) along a circumference of longitudinal axis of said device so as to deliver said predetermined volume $V_{sub}$ [ml] of said at least one substance to the sides of said at least one body cavity; (b) at a distal-most end of said device; and any combination thereof.

9. The device of claim 1, additionally comprising at least one expandable portion, configured to inflate before activation of said device.

10. The device of claim 1, additionally comprising at least one piercing needle configured to pierce said at least one delivery end.

11. The device of claim 10, wherein said at least one valve is at least one drug container plunger, such that when said at least one valve is configured to said active configuration, said predetermined volume $V_{gas}$ [ml] of said pressurized gas enters from said fluid tight chamber into said at least one delivery end to entrain said at least one substance and deliver said at least one substance via said at least one orifice in said at least one delivery end within said at least one body cavity.

12. The device of claim 1, additionally comprising at least one adjustable dose mechanism.

13. The device of claim 12, wherein said at least one adjustable dose mechanism comprises (a) at least one second drug container enclosing a predetermined volume $V_{dose}$ of at least one selected from the group consisting of said at least one substance, at least one secondary substance, and any combination thereof; and (b) at least one loading needle configured to load from said at least one second drug container, said volume $V_{sub}$ of at least one selected from a group consisting of said at least one substance, at least one secondary substance, and any combination thereof to said at least one delivery end, wherein when said at least one valve is configured from said inactive configuration to said active configuration, said predetermined volume $V_{gas}$ [ml] of said pressurized gas enters from said fluid-tight chamber into said at least one delivery end to entrain said predetermined volume $V_{sub}$ [ml] and deliver the same via said at least one orifice in said at least one delivery end within said at least one body cavity.

14. The device of claim 1, wherein said at least one delivery end additionally comprises at least one additional seal, adapted for sealing at least a portion of the at least one delivery end and preventing leakage therefrom.

15. The device of claim 14, wherein said at least one additional seal is adapted, prior to said at least one valve being reconfigured to said active configuration, to perform at least one step selected from a group consisting of: (i) separating said at least one delivery end and said chamber; (ii) sealing said at least one delivery end and preventing leakage of said predetermined volume $V_{sub}$ [ml] of said at least one substance out of said at least one delivery end, such that when said at least one valve is reconfigured to said active configuration, said sealing of said at least one additional seal is removed and said at least one substance mixes with said predetermined volume $V_{gas}$ of said pressurized gas within said at least one delivery end; and (iii) any combination thereof.

16. The device of claim 14, wherein said at least one additional seal is selected from a group consisting of at least one O-ring, at least one membrane, duckbill valve, at least one ball and any combination thereof.

17. The device of claim 1, wherein said at least one seal separates said at least one delivery end and said fluid-tight chamber.

18. The device of claim 1, wherein at least one of the following is held true:
(a) a release time, $dT_{release}$, of said $V_{sub}$ [ml or mg] of said at least one substance and said $V_{gas}$ [ml] of said pressurized gas is less than or equal to 500 milliseconds;
(b) $P_{gas}$ is in a range of about 1-10 barg;
(c) $V_{gas}$ is in a range of about 1-21 ml;
(d) $V_{sub}$ is in a range of about 0.01-7 ml; and
(e) dT is less than or equal to about 500 milliseconds;
(f) D is in a range of 0.2-6 mm;
(g) a pressure velocity $dP_{gas}/dT$ or $dP_{gas}/dT_{release}$ is greater than about 0.001 barg/ms;
(h) a volume rate $dV_{sub}/dT$ or $dV_{sub}/dT_{release}$ is greater than about 0.0001 ml/ms;
(i) a volume rate $dV_{gas}/dT$ or $dV_{gas}/dT_{release}$ is greater than about 0.001 ml/ms; or
(j) any combination thereof.

19. The device of claim 1, wherein said at least one seal separates said at least one delivery end and said fluid-tight chamber and adapted to seal at least one selected from a group consisting of said at least one delivery end, said fluid-tight chamber and any combination thereof.

20. The device of claim 1, wherein said at least one seal comprises an O-ring.

21. The device of claim 1, further comprising a mixing mechanism for creating a mixture of the predetermined volume $V_{gas}$ of said pressurized gas and the predetermined volume $V_{sub}$ of said at least one substance after said at least one valve is reconfigured to said active configuration.

22. The device of claim 21, wherein the mixing mechanism comprises at least one mixing element, the at least one mixing element comprising at least one mixing ball.

23. A device for delivering a predetermined amount $M_{sub}$ [mg] of at least one substance within at least one body cavity of a subject, said device comprising:
a) at least one predefined delivery end sized and shaped for containing said predetermined amount $M_{sub}$ [mg] of said at least one substance, said at least one delivery end configured for placement in proximity to said at least one body cavity and comprising at least one orifice of diameter D [mm];
b) a fluid-tight chamber configured to contain a predetermined volume $V_{gas}$ [ml] of pressurized gas at a predetermined pressure, $P_{gas}$ [barg], wherein said fluid-tight chamber is in fluid communication with said at least one delivery end upon activation of the device, wherein said fluid-tight chamber comprises at least one seal adapted to seal said predetermined volume $V_{gas}$ of said pressurized gas and prevent leakage of said pressurized gas from said fluid-tight chamber;
c) at least one valve mechanically connectable to said chamber, having at least two configurations:
(i) an active configuration in which said at least one valve enables delivery of predetermined amount $M_{sub}$ [mg] of said at least one substance from said at least one delivery end to said at least one body cavity via said at least one delivery end; and
(ii) an inactive configuration, in which said at least one valve prevents delivery of said predetermined amount $M_{sub}$ [mg] of said at least one substance from said at least one delivery end to said at least one body cavity;

wherein said at least one valve is reconfigurable from said inactive configuration to said active configuration, and vice versa, within a predetermined period of time, dT, in response to activation of said at least one valve;
wherein said pressurized gas, responsive to said at least one valve being reconfigured from said inactive configuration to said active configuration, is caused to exit said fluid-tight chamber and enter said at least one delivery end and to entrain said at least one substance and deliver said at least one substance via said at least one orifice in said at least one delivery end within said at least one body cavity in the form of an aerosol, such that a release time, $dT_{release}$, of said $M_{sub}$ [mg] of said at least one substance and said $V_{gas}$ [ml] of said pressurized gas is less than 500 milliseconds;
wherein said device is configured to deliver said predetermined amount $M_{sub}$ [mg] of said at least one substance and said predetermined volume $V_{gas}$ of said pressurized gas through said at least one orifice of diameter D [mm] to said at least one body cavity;
wherein said at least one delivery end is configured to accommodate a predetermined volume $V_{sub}$ [mg] of said at least one substance and said predetermined volume $V_{gas}$ of said pressurized gas after said at least one valve is reconfigured to said active configuration and said predetermined volume $V_{gas}$ of said pressurized gas exists said chamber and enters said at least one delivery end; and
wherein said at least one valve comprises a plunger accommodated within said fluid-tight chamber, said plunger interconnected with said at least one seal, wherein when said at least one valve is reconfigured from said inactive configuration to said active configuration by linearly moving said plunger, such that a seal of said chamber formed by said at least one seal is removed to allow said $V_{gas}$ [ml] of said pressurized gas to enter said at least one delivery end and entrain said at least one $M_{sub}$ substance to be delivered to said at least one body cavity.

24. The device of claim 23, wherein at least one of the following is satisfied:
a) said device is configured for a plurality of deliveries of said predetermined amount $M_{sub}$, said predetermined amount $M_{sub}$ being controllably alterable;
b) said at least on body cavity is a nasal cavity, the mouth, the throat, an ear, the vagina, the rectum, the urethra, and any combination thereof;
c) viscosity η of said at least one substance is in a range of about $1 \times 10^{-3}$ poise to about 1 poise;
d) a median particle size distribution, DV50, of a diameter of particles of said at least one substance, after exit from said device, is less than about 100 μm;
e) a particle diameter larger than 90% of particles of said at least one substance, DV90, is less than about 1000 μm;
f) a full width of a plume of aerosol comprising said at least one substance and said gas subtends an angle θ of about 25°;
g) particles in said plume have velocities in a range of about 5 m/s to 50 m/s;
h) said pressurized gas comprises air, nitrogen, oxygen, carbon dioxide, helium, neon, xenon and any combination thereof
i) during dispensing of said at least one substance, a mixture of said predetermined volume $V_{gas}$ [ml] of said pressurized gas with said predetermined amount $M_{sub}$ [mg] of said at least one substance entrained within it forms a plume of aerosol, said aerosol having a predetermined distribution, said distribution being either homogeneous or heterogeneous, said heterogeneous distribution is selected from a group consisting of: an arbitrary distribution, a distribution in which the density of said at least one substance within said mixture follows a predetermined pattern, and any combination thereof; characteristics of said aerosol selected from a group consisting of: particle size, particle shape, particle distribution, and any combination thereof, are determinable from characteristics of said device selected from a group consisting of: said predetermined volume of said pressurized gas, said predetermined amount of said at least one substance, said predetermined pressure of said pressurized gas, said predetermined orifice size, and any combination thereof;

j) said at least one substance is selected from a group consisting of a gas, a liquid, a powder, an aerosol, a slurry, a gel, a suspension and any combination thereof;

k) said at least one substance is stored under either an inert atmosphere or under vacuum to prevent reactions during storage; and l) a dose-response curve is substantially linear for brain concentration of said at least one substance when administered nasally via said device;

m) a dose-response curve for brain concentration having a fit selected from a group consisting of logarithmic, parabolic, exponential, sigmoid, power-low, and any combination thereof; of said at least one substance when administered nasally via said device.

25. The device of claim 23, wherein said at least one delivery end has a main longitudinal axis, said at least one delivery end comprising a number n of compartments, said at least one delivery end configured to contain said predetermined amount $M_{sub}$ [mg] of said at least one substance, said mass $M_{sub}$ [mg] of said at least one substance containable in at least one of said n compartments; at least one of the following being satisfied:

a) the number n of said compartments is an integer greater than or equal to 1; at least one said compartment has cross-section with shape selected from a group consisting of: wedge shaped, circular, oval, elliptical, polygonal, annular, and any combination thereof;

b) for said number n of compartments being an integer greater than 1, at least two said compartments have different volumes;

c) for said number n of compartments being an integer greater than 1, at least two said compartments have the same volume;

d) for said number n of compartments being an integer greater than 1, at least two said compartments have different cross-sectional areas;

e) for said number n of compartments being an integer greater than 1, at least two said compartments have the same cross-sectional area;

f) for said number n of compartments being an integer greater than 1, at least two said compartments contain different substances;

g) for said number n of compartments being an integer greater than 1, at least two said compartments contain the same substance;

h) for said number n of compartments being an integer greater than 1, at least two said compartments are disposed coaxially around said main longitudinal axis of said at least one capsule delivery end;

i) for said number n of compartments being an integer greater than 1, at least two said compartments are disposed sequentially along said main longitudinal axis of said at least one capsule delivery end;

j) for said number n of compartments greater than 1, a plurality of said one or more substances mix during dispensing of said plurality of substances; and k) for said number n of compartments greater than 1, said plurality of substances react during said dispensing.

26. The device of claim 23, wherein said at least one delivery end comprises an injection port fluidly connectable to an exterior of said device, said injection port configured such that said at least one substance is insertable into a dispensing chamber of said at least one delivery end via said port.

27. The device of claim 26, wherein said device comprises a port cover configured to provide an openable and closable air-tight closure for said port, said port cover slidable along said device, rotatable around said device, rotatable around a hinge on the exterior of said device or any combination thereof.

28. The device of claim 23, wherein said at least one delivery end comprises at least one separator configured to subdivide each said at least one delivery end into at least two compartments.

29. The device of claim 28, wherein said at least one separator is selected from a group consisting of at least two balls, at least one plunger, at least one thin sheet, at least one frangible membrane, at least one duckbill valve, at least one bendable membrane, at least one temperature dependent membrane, at least one pressure dependent membrane, and any combination thereof.

30. The device of claim 23, wherein said at least one orifice is disposed in at least one position selected from a group consisting of (a) along a circumference of longitudinal axis of said device so as to deliver said predetermined volume $V_{sub}$ [ml] of said at least one substance to the sides of said at least one body cavity; (b) at a distal-most end of said device; and any combination thereof.

31. The device of claim 23, additionally comprising at least one expandable portion, configured to inflate before activation of said device.

32. The device of claim 23, additionally comprising at least one piercing needle configured to pierce said at least one delivery end.

33. The device of claim 32, wherein said at least one valve is at least one drug container plunger, such that when said at least one valve is configured to said active configuration, said predetermined volume $V_{gas}$ [ml] of said pressurized gas enters from said fluid tight chamber into said at least one delivery end to entrain said at least one substance and deliver said at least one substance via said at least one orifice in said at least one delivery end within said at least one body cavity.

34. The device of claim 23, additionally comprising at least one an adjustable dose mechanism.

35. The device of claim 34, wherein said adjustable dose mechanism comprising (a) at least one second drug container enclosing a predetermined amount $M_{dose}$ of at least one selected from a group consisting of said at least one substance, at least one secondary substance, and any combination thereof; and (b) at least one loading needle configured to load from said at least one second drug container, wherein said predetermined amount $M_{sub}$ of at least one selected from a group consisting of said at least one substance, at least one secondary substance, and any combination thereof to said at least one delivery end, wherein when said at least one valve is configured from said inactive configuration to said active configuration, said predetermined volume $V_{gas}$ [ml] of said pressurized gas enters from said fluid-tight chamber into said at least one delivery end to entrain said predetermined amount $M_{sub}$ and deliver the same via said at least one orifice in said at least one delivery end within said at least one body cavity.

36. The device of claim 23, wherein said at least one delivery end additionally comprises at least one additional seal, adapted for sealing at least a portion of the at least one delivery end and preventing leakage therefrom.

37. The device of claim 36, wherein said at least one additional seal is adapted, prior to said at least one valve being reconfigured to said active configuration, to perform at least one step selected from a group consisting of: (i) separating said at least one delivery end and said chamber; (ii) sealing said at least one delivery end and preventing leakage of said predetermined volume $V_{sub}$ [ml] of said at least one substance out of said at least one delivery end, such that when said at least one valve is reconfigured to said active configuration, said additional seal is removed and said at least one substance mixes with said predetermined volume $V_{gas}$ of said pressurized gas within said at least one delivery end; and (iii) any combination thereof.

38. The device of claim 36, wherein said at least one additional seal is selected from a group consisting of at least one O-ring, at least one membrane, duckbill valve, at least one ball and any combination thereof.

39. The device of claim 23, wherein said at least one seal separates said at least one delivery end and said fluid-tight chamber and is adapted to seal at least one selected from a group consisting of said at least one delivery end, said fluid-tight chamber and any combination thereof.

40. The device of claim 23, wherein said at least one seal comprises an O-ring.

41. The device of claim 23, wherein at least one of the following is held true:
    i) $P_{gas}$ is in the range of about 1-10 barg;
    ii) $V_{gas}$ is in the range of about 1-12 ml;
    iii) $M_{sub}$ is in the range of about 1-1000 mg;
    iv) dT is less than or equal to about 500 milliseconds;
    v) $dT_{release}$ is less than or equal to about 500 milliseconds;
    vi) D is in the range of 0.2-6 mm;
    vii) a pressure rate is greater than about 0.001 barg/ms;
    viii) an amount rate $dM_{sub}/dT$ or $dM_{sub}/dT_{release}$ is greater than about 0.0001 mg/ms;
    ix) a volume rate $dV_{gas}/dT$ or $dV_{gas}/dT_{release}$ is greater than about 0.001 ml/ms.

42. The device of claim 23, further comprising a mixing mechanism for creating a mixture of the predetermined volume $V_{gas}$ of said pressurized gas and the predetermined amount $M_{sub}$ of said at least one substance after said at least one valve is reconfigured to said active configuration.

43. The device of claim 42, wherein the mixing mechanism comprises at least one mixing element, the at least one mixing element comprising at least one mixing ball.

44. A method of delivering a predetermined volume $V_{sub}$ [ml] of at least one substance within at least one body cavity of a subject, comprising:
    a) providing a device comprising:
       i) at least one predefined delivery end sized and shaped for containing said predetermined volume $V_{sub}$ [ml] of said at least one substance, said at least one delivery end comprising at least one orifice of diameter D [mm];
       ii) a fluid-tight chamber configured to contain a predetermined volume $V_{gas}$ [ml] of pressurized gas at a predetermined pressure, $P_{gas}$ [barg], wherein said fluid-tight chamber is in fluid communication with said at least one delivery end upon activation of the device, wherein said fluid-tight chamber comprises at least one seal adapted to seal said predetermined volume $V_{gas}$ of said pressurized gas and prevent leakage of said pressurized gas from said fluid-tight chamber;
       iii. at least one valve mechanically connected to said chamber, having at least two configurations:
           (i) an active configuration in which said at least one valve enables delivery of said predetermined volume $V_{sub}$ [ml] of said at least one substance from said at least one delivery end to said at least one body cavity via said at least one delivery end; and
           (ii) an inactive configuration, in which said at least one valve prevents delivery of said predetermined volume $V_{sub}$ [ml] of said at least one substance from said at least one delivery end to said at least one body cavity;
       wherein said at least one valve is reconfigurable from said inactive configuration to said active configuration, and vice versa, within a predetermined period of time, dT, in response to activation of said at least one valve, and wherein said pressurized gas, responsive to said at least one valve is reconfigured from said inactive configuration to said active configuration, is caused to exit said fluid-tight chamber and enter said at least one delivery end and to entrain said at least one substance and deliver said at least one substance via said at least one orifice in said at least one delivery end within said at least one body cavity in the form of an aerosol;
       wherein said at least one delivery end is configured to accommodate said predetermined volume $V_{sub}$ [ml] of said at least one substance and said predetermined volume $V_{gas}$ of said pressurized gas after said at least one valve is reconfigured to said active configuration and said predetermined volume $V_{gas}$ of said pressurized gas exits said chamber and enters said at least one delivery end;
       wherein said at least one valve comprises a plunger accommodated within said fluid-tight chamber, said plunger being interconnected with said at least one seal, and wherein when said at least one valve is reconfigured from said inactive configuration to said active configuration by linearly moving said plunger, such that a seal of said chamber formed by said at least one seal is removed to allow said $V_{gas}$ [ml] of said pressurized gas to enter said at least one delivery end and entrain an amount $M_{sub}$ of at least one substance to be delivered to said at least one body cavity;
    b) placing said at least one delivery end in proximity to said at least one body cavity;
    c) linearly moving said plunger thereby removing the seal of said chamber, which is provided by said at least one seal, and reconfiguring said at least one valve from said inactive configuration to said active configuration thereby removing said at least one seal and enabling said predetermined volume $V_{gas}$ of said pressurized gas to exit said fluid-tight chamber and entraining said at least one substance in said predetermined volume $V_{gas}$ of said pressurized gas; thereby mixing said predetermined volume $V_{sub}$ [ml] of said at least one substance and said predetermined volume $V_{gas}$ of said pressurized gas; and
    d) delivering said predetermined volume $V_{sub}$ [ml] of said at least one substance and said predetermined volume $V_{gas}$ of said pressurized gas through said at least one orifice of diameter D [mm] in a pressure rate of $dP_{gas}/dT$.

45. The method of claim 44, additionally comprising at least one of the following steps:
   a) generating a plurality of deliveries of said predetermined volume $V_{sub}$, and controllably altering said predetermined volume $V_{sub}$;
   b) selecting said at least on body cavity from a group consisting of a nasal cavity, the mouth, the throat, an ear, the vagina, the rectum, the urethra, and any combination thereof;
   c) selecting viscosity η of said at least one substance to be in a range of about $1 \times 10^{-3}$ poise to about 1 poise;
   d) characterizing a plume of said aerosol by a plume angle θ, said plume angle θ subtending the full width of said plume, said plume angle θ subtending an angle of less than about 25°;
   e) characterizing velocities of particles in said plume as being in a range of about 5 m/s to 50 m/s;
   f) selecting said gas from a group consisting of: air, nitrogen, oxygen, carbon dioxide, helium, neon, xenon and any combination thereof;
   g) dispensing said at least one substance, and during said step of dispensing, forming a plume of aerosol with predetermined distribution from a mixture of said predetermined volume $V_{gas}$ [ml] of said pressurized gas and said predetermined volume $V_{sub}$ [ml] entrained within it; selecting said predetermined distribution from a group consisting of: a homogeneous distribution, a heterogeneous distribution; selecting said heterogeneous distribution from a group consisting of: an arbitrary distribution, a distribution in which the density of said at least one substance within said mixture follows a predetermined pattern, and any combination thereof; selecting characteristics of said aerosol from a group consisting of: particle size, particle shape, particle distribution, and any combination thereof, are determinable from characteristics of said device selected from a group consisting of: said predetermined volume of said pressurized gas, said predetermined volume of said at least one substance, said predetermined pressure of said pressurized gas, said predetermined orifice size, and any combination thereof;
   h) selecting said at least one substance from a group consisting of: a gas, a liquid, a powder, a slurry, a gel, a suspension, and any combination thereof;
   i) storing said at least one substance under either an inert atmosphere or under vacuum, thereby preventing reactions during storage; and
   j) characterizing a dose-response curve for brain concentration of said at least one substance to be of substantially linear form;
   k) wherein the dose-response curve for brain concentration has a fit selected from a group consisting of: logarithmic, parabolic, exponential, sigmoid, power-low, and any combination thereof; of said at least one substance when administered nasally via said device.

46. The method of claim 44, additionally comprising steps of providing said at least one delivery end having a main longitudinal axis, said at least one delivery end comprising a number n of compartments, configuring said at least one delivery end to contain said predetermined volume $V_{sub}$ [ml] of said at least one substance, containing said volume $V_{sub}$ [ml] of said at least one substance in at least one of said n compartments; additionally comprising at least one of the following steps:
   a) providing said at least one delivery end with n compartments; n is an integer greater than or equal to 1;
   b) selecting a cross-sectional shape of at least one of said n compartments from a group consisting of: wedge shaped, circular, oval, elliptical, polygonal, annular, and any combination thereof;
   c) for said number n of compartments being an integer greater than 1, providing at least two of said plurality of said compartments having different volumes;
   d) for said number n of compartments being an integer greater than 1, providing at least two said compartments having the same volume;
   e) for said number n of compartments being an integer greater than 1, providing at least two said compartments having different cross-sectional areas;
   f) for said number n of compartments being an integer greater than 1, providing at least two said compartments having the same cross-sectional area;
   g) for said number n of compartments being an integer greater than 1, providing at least two of said compartments containing different substances;
   h) for said number n of compartments being an integer greater than 1, providing at least two of said compartments containing the same substance;
   i) for said number n of compartments being an integer greater than 1, disposing said plurality of compartments coaxially around said main longitudinal axis of said at least one delivery end;
   j) for said number n of compartments being an integer greater than 1, disposing said plurality of compartments sequentially along said main longitudinal axis of said at least one delivery end;
   k) for said number n of compartments being an integer greater than 1, mixing a plurality of said one or more substances during dispensing of said plurality of substances; and
   l) for said number n of compartments being an integer greater than 1, reacting said plurality of substances during said dispensing.

47. The method of claim 44, additionally comprising inserting said predetermined volume $V_{sub}$ [ml] of said at least one substance into a dispensing chamber of said at least one delivery end via an injection port fluidly connectable to an exterior of said device.

48. The method of claim 47, additionally comprising providing a port cover configured to provide an openable and closable air-tight closure for said injection port, and of moving said port cover relative to said device in at least one motion selected from a group consisting of: sliding said port cover along said device, rotating said port cover around said device, rotating said port cover around a hinge on the exterior of said device and any combination thereof.

49. The method of claim 44, wherein:
   (a) a release time, $dT_{release}$, of said $V_{sub}$ [ml or mg] of said at least one substance and said $V_{gas}$ [ml] of said pressurized gas is less than or equal to 500 milliseconds;
   (b) $P_{gas}$ is in a range of about 1-10 barg;
   (c) $V_{gas}$ is in a range of about 1-21 ml;
   (d) $V_{sub}$ is in a range of about 0.01-7 ml;
   (e) dT is less than or equal to about 500 milliseconds;
   (f) D is in a range of 0.2-6 mm;
   (g) a pressure velocity $dP_{gas}/dT$ or $dP_{gas}/dT_{release}$ is greater than about 0.001 barg/ms;
   (h) a volume rate $dV_{sub}/dT$ or $dV_{sub}/dT_{release}$ is greater than about 0.0001 ml/ms;

(i) a volume rate $dV_{gas}/dT$ or $dV_{gas}/dT_{release}$ is greater than about 0.001 ml/ms; or (j) any combination thereof.

50. The method of claim 44, wherein said at least one seal separates said at least one delivery end and said fluid-tight chamber and adapted to seal at least one selected from a group consisting of said at least one delivery end, said fluid-tight chamber and any combination thereof.

51. The method of claim 44, wherein said at least one seal comprises an O-ring.

52. The method of claim 44, additionally providing said at least one delivery end with at least one additional seal, adapted for sealing at least a portion of the at least one delivery end and preventing leakage therefrom.

53. The method of claim 52, wherein said at least one additional seal is adapted, prior to said at least one valve being reconfigured to said active configuration, to perform at least one step selected from a group consisting of: (i) separating said at least one delivery end and said chamber; (ii) sealing at least one portion of said ended delivery end and preventing leakage of said predetermined volume $V_{sub}$ [ml] of said at least one substance out of said at least one delivery end, such that when said at least one valve is reconfigured to said active configuration, said at least one additional seal is removed and said at least one substance mixes with said predetermined volume $V_{gas}$ of said pressurized gas within said at least one delivery end; and (iii) any combination thereof.

54. The method of claim 52, wherein said at least one additional seal is selected from a group consisting of at least one O-ring, at least one membrane, duckbill valve, at least one ball and any combination thereof.

55. The method of claim 52, wherein said step (c) of linearly moving said plunger results in removing said at least one seal of said at least one delivery end.

56. The method of claim 44, wherein said at least one delivery end comprises at least one separator configured to subdivide each said at least one delivery end into at least two compartments.

57. The method of claim 56, wherein said at least one separator is selected from a group consisting of at least two balls, at least one plunger, at least one thin sheet, at least one frangible membrane, at least one duckbill valve, at least one bendable membrane, at least one temperature dependent membrane, at least one pressure dependent membrane, and any combination thereof.

58. The method of claim 44, wherein said at least one orifice is disposed in at least one position selected from a group consisting of (a) along a circumference of longitudinal axis of said device so as to deliver said predetermined volume $V_{sub}$ [ml] of said at least one substance to the sides of said at least one body cavity; (b) at a distal-most end of said device; and any combination thereof.

59. The method of claim 44, wherein said device further comprises at least one expandable portion, configured to inflate before activation of said device.

60. The method of claim 44, wherein said device further comprises at least one piercing needle configured to pierce said at least one delivery end.

61. The method of claim 44, wherein said device further comprises at least one an adjustable dose mechanism.

62. The method of claim 61, wherein said at least one adjustable dose mechanism comprises (a) at least one second drug container enclosing a predetermined volume $V_{dose}$ of at least one selected from a group consisting of said at least one substance, at least one secondary substance and any combination thereof; and (b) at least one loading needle configured to load from said at least one second drug container, said volume $V_{sub}$ of at least one selected from a group consisting of said at least one substance, at least one secondary substance and any combination thereof to said at least one delivery end, wherein when said at least one valve is configured from said inactive configuration to said active configuration, said predetermined volume $V_{gas}$ [ml] of said pressurized gas enters from said fluid-tight chamber into said at least one delivery end to entrain said predetermined volume $V_{sub}$ [ml] and deliver the same via said at least one orifice in said at least one delivery end within said at least one body cavity.

63. The method of claim 44, additionally comprising at least one step selected from a group consisting of:
   a) emplacing said at least one substance in said at least one predefined delivery end;
   b) setting said at least one valve in said inactive configuration; and
   c) pressurizing said fluid-tight chamber with said gas to said predetermined pressure.

64. The method of claim 44, wherein said device comprises a mixing mechanism for creating a mixture of the predetermined volume $V_{gas}$ of said pressurized gas and the predetermined volume $V_{sub}$ of said at least one substance after said at least one valve is reconfigured to said active configuration.

65. The method of claim 64, wherein the mixing mechanism comprises at least one mixing element, the at least one mixing element comprising at least one mixing ball.

66. A method of delivering a predetermined amount $M_{sub}$ [mg] of at least one substance within at least one body cavity of a subject, comprising:
   a) providing a device comprising:
      i) at least one predefined delivery end sized and shaped for containing said predetermined amount $M_{sub}$ [mg] of said at least one substance, wherein said at least one delivery end comprises at least one orifice of diameter D [mm];
      ii) a fluid-tight chamber configured to contain predetermined volume $V_{gas}$ [ml] of pressurized gas at a predetermined pressure, $P_{gas}$ [barg], wherein said fluid-tight chamber is in fluid communication with said at least one delivery end upon activation of the device, wherein said fluid-tight chamber comprises at least one seal adapted to seal said predetermined volume $V_{gas}$ of said pressurized gas and prevent leakage of said pressurized gas from said fluid-tight chamber;
      iii) at least one valve mechanically connected to said chamber, having at least two configurations:
         (i) an active configuration in which said at least one valve enables delivery of said predetermined amount $M_{sub}$ [mg] of said at least one substance from said at least one delivery end to said at least one body cavity via said at least one delivery end; and
         (ii) an inactive configuration, in which said at least one valve prevents delivery of said predetermined amount $M_{sub}$ [mg] of said at least one substance from said at least one capsule delivery end to said at least one body cavity;
      wherein said at least one valve is reconfigurable from said inactive configuration to said active configuration, and vice versa, within a predetermined period of time, dT, in response to activation of said at least one valve wherein said pressurized gas, responsive to said at least one valve being reconfigured from said inactive configuration to said active configuration, is caused to exit said fluid-tight chamber and enter said at least one delivery end and to entrain said at least one substance and deliver said at least one substance via said at least one orifice in said at least one delivery end within said at least one body cavity in the form of an aerosol, such that the release time, $dT_{release}$, of said $M_{sub}$ [mg] of said at least one substance and said $V_{gas}$ [ml] of said pressurized gas is less than 500 milliseconds;

wherein said at least one delivery end is configured to accommodate said predetermined amount $M_{sub}$ [mg] of said at least one substance and said predetermined volume $V_{gas}$ of said pressurized gas after said at least one valve is reconfigured to said active configuration and said predetermined volume $V_{gas}$ of said pressurized gas exits said chamber and enters said at least one delivery end;

wherein said at least one valve comprises a plunger accommodated within said fluid-tight chamber, said plunger being interconnected with said at least one seal, and wherein when said at least one valve is reconfigured from said inactive configuration to said active configuration by linearly moving said plunger, such that a seal of said chamber formed by the at least one seal is removed to allow said $V_{gas}$ [ml] of said pressurized gas to enter said at least one delivery end and entrain said at least one $M_{sub}$ substance to be delivered to said at least one body cavity;

b) placing said at least one delivery end in proximity to said at least one body cavity;

c) linearly moving said plunger thereby removing the seal of said chamber formed by said at least one seal, and reconfiguring said at least one valve from said inactive configuration to said active configuration thereby removing said at least one seal and enabling said predetermined volume $V_{gas}$ of said pressurized gas to exit said fluid-tight chamber and entraining and mixing said predetermined amount $M_{sub}$ [mg] of said at least one substance in said predetermined volume $V_{gas}$ of said pressurized gas; and d) delivering said predetermined amount $M_{sub}$ [mg] of said at least one substance and said predetermined volume $V_{gas}$ of said pressurized gas through said at least one orifice of diameter D [mm] in a pressure rate of $dP_{gas}/dT$.

67. The method of claim 66, additionally comprising at least one of the following:
a) generating a plurality of deliveries of said predetermined amount $M_{sub}$, and controllably altering said predetermined amount $M_{sub}$;
b) selecting said at least one body cavity from a group consisting of a nasal cavity, the mouth, the throat, an ear, the vagina, the rectum, the urethra, and any combination thereof;
c) selecting viscosity η of said at least one substance to be in a range of about $1 \times 10^{-3}$ poise to about 1 poise;
d) characterizing a plume of said aerosol by a plume angle θ, said plume angle θ subtending the full width of said plume, said plume angle θ subtending an angle of less than about 25°;
e) characterizing velocities of particles in said plume as being in a range of about 5 m/s to 50 m/s;
f) selecting said gas from a group consisting of: air, nitrogen, oxygen, carbon dioxide, helium, neon, xenon and any combination thereof;
g) dispensing said at least one substance, and during said step of dispensing, forming a plume of aerosol with predetermined distribution from a mixture of said predetermined volume $V_{gas}$ [ml] of said pressurized gas and said predetermined amount $M_{sub}$ [mg] entrained within it; selecting said predetermined distribution from a group consisting of: a homogeneous distribution, a heterogeneous distribution; selecting said heterogeneous distribution from a group consisting of: an arbitrary distribution, a distribution in which the density of said at least one substance within said mixture follows a predetermined pattern, and any combination thereof; selecting characteristics of said aerosol from a group consisting of: particle size, particle shape, particle distribution, and any combination thereof, are determinable from characteristics of said device selected from a group consisting of: said predetermined volume of said pressurized gas, said predetermined amount of said at least one substance, said predetermined pressure of said pressurized gas, said predetermined orifice size, and any combination thereof;
h) selecting said at least one substance from a group consisting of: a gas, a liquid, a powder, a slurry, a gel, a suspension, and any combination thereof;
i) storing said at least one substance under either an inert atmosphere or under vacuum, thereby preventing reactions during storage;
j) characterizing a dose-response curve for brain concentration of said at least one substance to be of substantially linear form;
k) wherein said dose-response curve for brain concentration has a fit selected from a group consisting of logarithmic, parabolic, exponential, sigmoid, power-low, and any combination thereof; of said at least one substance when administered nasally via said device.

68. The method of claim 66, additionally comprising at least one step selected from a group consisting of:
e) emplacing said at least one substance in said at least one predefined delivery end;
f) setting said at least one valve in said inactive configuration;
g) pressurizing said fluid-tight chamber with said gas to said predetermined pressure.

69. The method of claim 66, wherein said at least one seal separates said at least one delivery end and said fluid-tight chamber and adapted to seal at least one selected from a group consisting of said at least one delivery end, said fluid-tight chamber and any combination thereof.

70. The method of claim 66, wherein said at least one seal comprises an O-ring.

71. The method of claim 66, additionally providing said at least one delivery end with at least one additional seal, adapted for sealing at least a portion of the at least one delivery end and preventing leakage therefrom.

72. The method of claim 71, wherein said at least one additional seal is adapted, prior to said at least one valve being reconfigured to said active configuration, to perform at least one step selected from a group consisting of: (i) separating said at least one delivery end and said chamber; (ii) sealing at least one portion of said at least one delivery end and preventing leakage of said predetermined volume amount $M_{sub}$ [mg] of said at least one substance out of said delivery end, such that when said at least one valve is reconfigured to said active configuration, said additional seal is removed and said at least one substance mixes with said predetermined volume $V_{gas}$ of said pressurized gas within said at least one delivery end; and (iii) any combination thereof.

73. The method of claim 71, wherein said at least one additional seal is selected from a group consisting of at least one O-ring, at least one membrane, duckbill valve, at least one ball and any combination thereof.

74. The method of claim 71, wherein said step (c) of linearly moving said plunger results in removing said at least one seal of said at least one delivery end.

75. The method of claim 66, wherein said at least one delivery end comprises at least one separator configured to subdivide each said at least one delivery end into at least two compartments.

76. The method of claim 75, wherein said at least one separator is selected from a group consisting of at least two balls, at least one plunger, at least one thin sheet, at least one frangible membrane, at least one duckbill valve, at least one bendable membrane, at least one temperature dependent membrane, at least one pressure dependent membrane, and any combination thereof.

77. The method of claim 66, wherein said at least one orifice is disposed in at least one position selected from a group consisting of (a) along a circumference of longitudinal axis of said device so as to deliver said predetermined amount $M_{sub}$ [mg] of said at least one substance to the sides of said at least one body cavity; (b) at a distal-most end of said device; and any combination thereof.

78. The method of claim 66, wherein said device further comprises at least one expandable portion, configured to inflate before activation of said device.

79. The method of claim 66, wherein said device further comprises at least one piercing needle configured to pierce said at least one delivery end.

80. The method of claim 66, wherein said device further comprises at least one an adjustable dose mechanism.

81. The method of claim 80, wherein said at least one adjustable dose mechanism comprises (a) at least one second drug container enclosing a predetermined volume $M_{dose}$ of at least one selected from a group consisting of said at least one substance, at least one secondary substance and any combination thereof; and (b) at least one loading needle configured to load from said at least one second drug container, said amount $M_{sub}$ of at least one selected from a group consisting of said at least one substance, at least one secondary substance and any combination thereof to said at least one delivery end, wherein when said at least one valve is configured from said inactive configuration to said active configuration, said predetermined volume $V_{gas}$ [ml] of said pressurized gas enters from said fluid-tight chamber into said at least one delivery end to entrain said predetermined amount $M_{sub}$ [mg] of said at least one substance and deliver the same via said at least one orifice in said at least one delivery end within said at least one body cavity.

82. The method of claim 66, wherein at least one of the following is held true:
 i) $P_{gas}$ is in the range of about 1-10 barg;
 ii) $V_{gas}$ is in the range of about 1-12 ml;
 iii) $M_{sub}$ is in the range of about 1-1000 mg;
 iv) dT is less than or equal to about 500 milliseconds;
 v) $dT_{release}$ is less than or equal to about 500 milliseconds;
 vi) D is in the range of 0.2-6 mm;
 vii) a pressure rate is greater than about 0.001 barg/ms;
 viii) an amount rate $dM_{sub}/dT$ or $dM_{sub}/dT_{release}$ is greater than about 0.0001 mg/ms;
 ix) a volume rate $dV_{gas}/dT$ or $dV_{gas}/dT_{release}$ is greater than about 0.001 ml/ms.

83. The method of claim 66, wherein said device comprises a mixing mechanism for creating a mixture of the predetermined volume $V_{gas}$ of said pressurized gas and the predetermined amount $M_{sub}$ of said at least one substance after said at least one valve is reconfigured to said active configuration.

84. The method of claim 83, wherein the mixing mechanism comprises at least one mixing element, the at least one mixing element including at least one mixing ball.

* * * * *